United States Patent
Johnson et al.

(10) Patent No.: US 10,011,549 B2
(45) Date of Patent: Jul. 3, 2018

(54) ELECTROCHEMICALLY ACTIVE AGENTS FOR PH MODULATION IN BIOLOGICAL BUFFERS

(71) Applicant: Robert Bosch GmbH, Stuttgart (DE)

(72) Inventors: Christopher Johnson, Mountain View, CA (US); Sam Kavusi, Menlo Park, CA (US); Nadezda Fomina, Fremont, CA (US); Habib Ahmad, Sunnyvale, CA (US); Autumn Maruniak, Fremont, CA (US); Christoph Lang, Cupertino, CA (US); Ashwin Raghunathan, San Francisco, CA (US)

(73) Assignee: ROBERT BOSCH GMBH, Stuttgart (DE)

( * ) Notice: Subject to any disclaimer, the term of this patent is extended or adjusted under 35 U.S.C. 154(b) by 125 days.

(21) Appl. No.: 14/792,553

(22) Filed: Jul. 6, 2015

(65) Prior Publication Data

US 2017/0008825 A1 Jan. 12, 2017

(51) Int. Cl.
*G01N 27/327* (2006.01)
*C07C 49/84* (2006.01)
(Continued)

(52) U.S. Cl.
CPC .............. *C07C 49/84* (2013.01); *C07C 37/07* (2013.01); *C07C 39/10* (2013.01); *C07C 39/11* (2013.01);
(Continued)

(58) Field of Classification Search
CPC .................... G01N 27/327–27/3272; G01N 27/3275–27/3277
See application file for complete search history.

(56) References Cited

U.S. PATENT DOCUMENTS 5,171,689 A * 12/1992 Kawaguri .............. C12Q 1/001
204/403.1
6,618,934 B1 9/2003 Feldman et al.
(Continued)

FOREIGN PATENT DOCUMENTS

CN 1098502 2/1995
CN 102023181 4/2011
(Continued)

OTHER PUBLICATIONS

Borgmann et al., Amperometric Biosensors, Advances in Electrochemical Science and Engineering, 2011, pp. 1-84.
(Continued)

*Primary Examiner* — Alexander S Noguerola
(74) *Attorney, Agent, or Firm* — Gerard Messina

(57) ABSTRACT

Device and methods for use in a biosensor comprising a multisite array of test sites, the device and methods being useful for modulating the binding interactions between a (biomolecular) probe or detection agent and an analyte of interest by modulating the pH or ionic gradient near the electrodes in such biosensor. An electrochemically active agent that is suitable for use in biological buffers for changing the pH of the biological buffers. Method for changing the pH of biological buffers using the electrochemically active agents. The methods of modulating the binding interactions provided in a biosensor, analytic methods for more accurately controlling and measuring the pH or ionic gradient near the electrodes in such biosensor, and analytic methods for more accurately measuring an analyte of interest in a biological sample.

55 Claims, 55 Drawing Sheets

(51) Int. Cl.

| | | |
|---|---|---|
| *C12Q 1/00* | (2006.01) | |
| *G01N 33/543* | (2006.01) | |
| *C07C 37/07* | (2006.01) | |
| *C07C 39/10* | (2006.01) | |
| *C07C 41/24* | (2006.01) | |
| *C07C 41/30* | (2006.01) | |
| *C07C 43/178* | (2006.01) | |
| *C07C 43/205* | (2006.01) | |
| *C07C 45/42* | (2006.01) | |
| *C07C 49/82* | (2006.01) | |
| *G01N 27/30* | (2006.01) | |
| *C07C 39/11* | (2006.01) | |
| *C07C 43/225* | (2006.01) | |
| *C07C 43/23* | (2006.01) | |

(52) U.S. Cl.
CPC ............. *C07C 41/24* (2013.01); *C07C 41/30* (2013.01); *C07C 43/1783* (2013.01); *C07C 43/2055* (2013.01); *C07C 43/225* (2013.01); *C07C 43/23* (2013.01); *C07C 45/42* (2013.01); *C07C 49/82* (2013.01); *C12Q 1/004* (2013.01); *G01N 27/302* (2013.01); *G01N 27/327* (2013.01); *G01N 33/5438* (2013.01)

(56) References Cited

U.S. PATENT DOCUMENTS

| | | |
|---|---|---|
| 6,753,312 B2 | 6/2004 | Yatcilla et al. |
| 6,797,152 B2 | 9/2004 | Freund et al. |
| 6,887,714 B2 | 5/2005 | Fritsch et al. |
| 6,976,982 B2 | 12/2005 | Santini, Jr. et al. |
| 7,195,913 B2 | 3/2007 | Guire et al. |
| 7,785,785 B2 | 8/2010 | Pourmand et al. |
| 8,436,621 B2 | 5/2013 | Lee et al. |
| 8,552,730 B2 | 10/2013 | Chiao et al. |
| 8,648,016 B2 | 2/2014 | Kavusi et al. |
| 8,906,617 B2 | 12/2014 | Rothberg et al. |
| 8,932,868 B2 | 1/2015 | Van Grinsven et al. |
| 2003/0228523 A1 | 12/2003 | DeLongchamp et al. |
| 2008/0044911 A1 | 2/2008 | Bock et al. |
| 2008/0305486 A1 | 12/2008 | Tan et al. |
| 2009/0026082 A1 | 1/2009 | Rothberg et al. |
| 2009/0061524 A1 | 3/2009 | Rishpon et al. |
| 2009/0117551 A1 | 5/2009 | Miho et al. |
| 2010/0105035 A1 | 4/2010 | Hashsham et al. |
| 2010/0116691 A1 | 5/2010 | Papadimitrakopoulos et al. |
| 2010/0285601 A1 | 11/2010 | Kong et al. |
| 2011/0087315 A1 | 4/2011 | Richardson-Burns et al. |
| 2011/0091870 A1 | 4/2011 | Lang et al. |
| 2011/0278258 A1 | 11/2011 | Kavusi et al. |
| 2012/0085660 A1 | 4/2012 | Rothberg et al. |
| 2012/0115236 A1 | 5/2012 | Chen et al. |
| 2012/0152763 A1* | 6/2012 | Takahara ........... G01N 27/3272 205/777.5 |
| 2012/0164351 A1 | 6/2012 | Gindilis |
| 2012/0222958 A1 | 9/2012 | Pourmand et al. |
| 2013/0334467 A1 | 12/2013 | Zhou et al. |
| 2014/0008244 A1 | 1/2014 | Kavusi et al. |
| 2014/0274760 A1 | 9/2014 | Fomina et al. |
| 2014/0370636 A1 | 12/2014 | Dalton et al. |

FOREIGN PATENT DOCUMENTS

| | | | |
|---|---|---|---|
| JP | 2005506527 | 3/2005 | |
| JP | 2008241409 | 10/2008 | |
| JP | 2010035555 | 2/2010 | |
| JP | 2011135781 | 7/2011 | |
| WO | WO-2001011080 A1 | 2/2001 | |
| WO | WO 2007/004971 A1 * | 1/2007 | ............... C25B 1/30 |
| WO | WO-2011047020 A1 | 4/2011 | |
| WO | 2011143188 | 11/2011 | |
| WO | WO-2012076350 A1 | 6/2012 | |
| WO | WO-2012116385 A1 | 9/2012 | |
| WO | 2014008038 | 1/2014 | |

OTHER PUBLICATIONS

Turner, "Biosensors: Sense and Sensibility", Chem Soc Rev, 2013, 42(8), pp. 3125-3638.

Yotter et al., Sensor Technologies For Monitoring Activity in Single Cells—Part I: Optical Methods, IEEE Sensors Journal, 2004, 4(4), pp. 395-411.

Bocharova et al., "Reversible gating contorlled by enzymes at nanostructured interface", Chemical Communications—CHEMCOM., vol. 46, No. 12, Jan. 1, 2010, pp. 645-650.

Tam et al., "Biochemically Controlled Bioelectrocatalytic Interface", Journal of the American Chemical Society, vol. 130, No. 33, Aug. 1, 2008, pp. 10888-10889.

"Simazine" entry obtained from the EXTOXNET (Extension Toxicology Network) website http:pmep.cce.cornell.edu/profiles/extoxnet/pyrethrins-ziram/simazine-ext.html, published Sep. 1993, downloaded Nov. 7, 2014.

Amaro et al., "Metabolic Activation of PCBs to Quinones: Reactivity toward Nitrogen and Sulfur Nucleophiles and Influence of Superoxide Dismutase", American Chemical Society, 1996, vol. 9(3), pp. 623-629.

Anderson et al., A System for Multiplexed Direct Electrical Detection of DNA Synthesis, Sens Actuators B Chem., 2008, 129(1).

Artzy-Schnirman et al., "A Two-State Electronic Antigen and an Antibody Selected toDiscriminte Between These States", Nano Letters, 2008, vol., No. 10, pp. 3398-3403.

Bazin, Damien et al., "Electrodeposition of Polymer Nanodots with Controlled Density and Their Reversible Functionalization by Polyhistidine-Tag Proteins", Langmuir, vol. 28, No. 39, Oct. 2, 2012, pp. 13968-13975.

Bizzarri et al., Green Flourescent Protein Based pH Indicators for In Vivo Use: A Review, Anal. Bioanal. Chem., 2009, p. 393, pp. 1107-1122.

Cannan et al., "Three-dimensional imaging of proton gradients at microelectrode surfaces using confocal laser scanning microscopy", Electrochemistry Communications 4 (2002), pp. 886-892.

Chambers, J.Q., "Electrochemistry of quinones", The Chemistry of the Quinonoid Compounds, Chapter 12, , Pt. 2, pp. 719-757.

Chambers, J.Q., "Electrochemistry of quinones", The Chemistry of the Quinonoid Compounds, Chapter 14, Pt. 2, pp. 737-791.

Chang et al., "Glucose concentration determination based on silica sol-gel encapsulated glucose oxidase optical biosensor arrays", Talanta, Elsevier, Amsterdam, NL, vol. 83, No. 1, Nov. 15, 2010, pp. 61-65.

Choi, JW et al., "Charge trap in self-assembled monolayer of cytochrome b562-green fluorescent protein chimera", Current Applied Physics, North-Holland, Amsterdam, NL, vol. 6, No. 4, Jul. 1, 2006, pp. 760-765.

Crone et al., "GFP-Based Biosensors", Intech, Chapter 1, State of the Art in Biosensors—General Aspects, 2013, pp. 1-34.

Elsen et al., "Determination of the capacitance of solid-state potentiometric sensors: An electrochemical time-of-flight method method", Analytical Chemistry, vol. 78, No. 18, pp. 6356-6363 (2006).

Evans, D.H. Encyclopedia Electrochem. Elem., 1978, vol. 12, pp. 1-259.

Frasconi et al., "Electrochemically Stimulated pH Changes: A Route to Control Chemical Reactivity," J. Am. Chem. Soc. (2010) 132(6), pp. 2029-2036.

Gao et al., "A DNA biosensor based on a morpholino oligomer coated indium-tin oxide electrode and a cationic redox polymer", The Analyst, vol. 134, No. 5, Jan. 1, 2009, p. 952.

Ge et al., "pH-sensing properties of poly(aniline) ultrathin films self-assembled on indium-tin oxide", Analytical Chemistry, vol. 79(4), pp. 1401-1410 (2007).

Hodneland et al., "Biomolecular surfaces that release ligands under electrochemical control", J. Am. Chem Soc., pp. 4235-4236 (2000).

(56) References Cited

OTHER PUBLICATIONS

Hotta et al., "In situ monitoring of the H<+> concentration change near an electrode surface through electrolysis using slab optical waveguide pH sensor", Electrochemistry Communications, Elsevier, Amsterdam, NL, vol. 10, No. 9, Sep. 1, 2008, pp. 1351-1354.
International Search Report dated Jul. 29, 2014 of the corresponding International Application PCT/US2014/026250 filed Mar. 13, 2014.
International Search Report dated Sep. 17, 2013 of the corresponding International Application PCT/US2013/047563 filed Jun. 25, 2013.
Kirk-Othmer Encyclopedia of Chemical Technology, "Hydrogen-Ion Activity", Copyright John Wiley & Sons, Inc., pp. 1-15.
Kirk-Othmer Encyclopedia of Chemical Technology, "Quinones", Copyright John Wiley & Sons, Inc., pp. 1-35.
Korostynska, Olga et al., "Review on State-of-the-art in Polymer Based pH Sensors" Sensors, Jan. 1, 2007, pp. 3027-3042. Retrieved from the internet: URL: <http://www.ncbi.nlm.nih.gov/pmc/articles/PMC3841878/pdf/sensors-07-03027.pdf>.
Kozlovskaja et al., "Response of hydrogen peroxide, ascorbic acid, and paracetamol at a platinum electrode coated with microfilms of polyaniline", Microchimica Acta; An International Journal on Micro and Traceanalysis, Springer-Verlag, VI, vol. 166, No. 3-4, Jul. 28, 2009, pp. 229-234.
Liu et al., "pH-switchable bioelectroatalysis based on layer-by-layer films assembled with glucose oxidase and branched poly(ethyleneimine)", Sensors and Actuators B: Chemical: International Journal Devoted to Research and Development of Physical and Chemical Transducers, Elsevier S.A., Switzerland, vol. 156, No. 2, Feb. 7, 2011, pp. 645-650.
Loomis et al., "Plant Phenolic Compounds and the Isolation of Plant Enzymes", Phytochemistry, vol. 5, pp. 423-438, (1966).
Maurer, K. et al., "Electrochemically Generated Acid and Its Containment to 100 Micron Reaction Areas for the Production of DNA Microarrays", PLOS One 2006, Issue 1, e34, pp. 1-7.
Mu et al., "Catechol sensor using poly(aniline-co-o-aminophenol) as an electron transfer mediator", Biosensors and Bioelectronics, Elsevier BV, NL, vol. 21, No. 7, Jan. 15, 2006, pp. 1237-1243.
Oshige, Masahiko et al., "Immobilization of His-Tagged Proteins on Various Solid Surfaces Using NTA-Modified Chitosan", Open Journal of Polymer Chemistry, Feb. 1, 2013, pp. 3, 6-10.

Quan et al., "Voltammetry of Quinones in Unbuffered Aqueous Solution: reassessing the roles of proton transfer and hydrogen bonding in the aqueous electrochemistry of quinones", J. Am. Chem. Soc. 129(42), pp. 12847-12856 (2007).
Ribereau-Gayon et al., "The Microbiology of Wine and Vinifications", Handbook of Enology, vol. 1, 2nd ed. John Wiley Sons, Ltd. 2006, p. 234.
Slowinska et al., "An electrochemical time-of-flight technique with galvanostatic generation and potentiometric sensing", Journal of Electroanalytical Chemistry, vol. 554-555, pp. 61-69 (2003).
Steenken, S., "One-Electron-Reduction Potentials of Pyrimidine Bases, Nucleosides, and Nucleotides in Aqueous Solution. Consequences for DNA Redox Chemistry", J. Am. Chem. Soc., 1992, 114:4701-09.
Yin, Li-Te et al., "Study of indium tin oxide thin film for separative extended gate ISFET," Materials Chemistry and Physics, 70(1), pp. 12-16 (2001).
Yin.D.X, et al., "Tetracycline-Controlled Gene Expression System Achieves High-Level and Quantitative Control of Gene Expression", Analytical Biochemistry,1996, 235: pp. 195-201.
Zeravik et al., "A highly sensitive flow-through amperometric immunosensor based on the Peroxidase chip and enzyme-channeling principle", Biosensors and Bioelectronics, vol. 18 No. 11, Oct. 1, 2003, pp. 1321-1327.
Zhang, J., Protein-Protein Interactions in Salt Solutions, Intech, 2012, pp. 359-377.
Natalia V. Lebedeva et al., "Structural and pH Dependence of Excited State PCET Reactions involving Reductive Quenching of the MLCT Excited States of [Ru II (bpy) 2 (bpy)] 2+ of Hyrodquinones" Journal of Physical Chemistry, Apr. 21, 2011, 3346-3356, 115-15.
Walter Reppe et al., "Carbonylierung VI. Synthesen mit Metalcarbonylwasserstoffen" Justus Liebigs Annalen Der Chemie, Aug. 26, 1953, 133-161, 582-1.
Kimio Hamamura et al., "Synthesis of deuterium-labelled coenzyme Q10" Journal of Labelled Compounds and Radiopharmaceuticals, Sep. 1, 2002, 831-839, 45-10.
Mark D Canatelli et al., "Laccase-catalyzed [alpha]-arylation of benzoylacetonitrile with substituted hydroquinones" Chemical Engineering Research and Design, Part A, Institution of Chemical Engineers, Sep. 3, 2014, 128-134, 97.

* cited by examiner

ELECTROCHEMICALLY ACTIVE AGENTS FOR PH MODULATION IN BIOLOGICAL BUFFERS

FIELD OF THE INVENTION

The invention relates to a biosensor device for use in diagnostic methods for biomolecules. The invention also relates to a method and corresponding devices and systems for detecting the presence of bubbles in an aqueous solution; and glass slides for performing life science experiments, in which at least some of the processing of data measured at the slide is performed by a computer processor located on the slide or by a processor on a peripheral component connected to a body of, or wirelessly coupled to the slide. The invention also relates to the use of electrochemical reactions, in particular redox reactions, in a solution to modulate the pH of the solution using electric current. The invention also relates to biological buffers and in particular electrochemically active agents that are compatible for use in biological buffers and are usable to facilitate pH modulation in biological buffers. Moreover, the invention relates to a method for generating a pH concentration gradient near electrode surfaces for modulating biomolecular interactions in such biosensor, a method for using integrated electronic systems for improving the accuracy, precision, and reliability in controlling a pH gradient near electrode surfaces, methods for controlling the pH in order to modulate biomolecular interactions in such biosensor, a diagnostic method for biomolecules using a biosensor, and methods of improving such biosensor.

BACKGROUND INFORMATION

Recently there has been an increased interest in predictive, preventative, and particularly personalized medicine which requires diagnostic tests with higher fidelity, e.g., sensitivity and specificity. Multiplexed measurement platforms, e.g., protein arrays currently used in research, are among the promising diagnostics technologies for the near future. The samples in these tests can be human body fluids such as blood, serum, saliva, biological cells, urine, or other biomolecules but can also be consumables such as milk, baby food, or water. Within this field there is a growing need for low-cost, multiplexed tests for biomolecules such as nucleic acids, proteins, and also small molecules. Achieving the sensitivity and specificity needed in such tests is not without difficult challenges. Combining these tests with integrated electronics and using CMOS technology has provided solutions to some of the challenges.

The two main limitations in a detection assay include sensitivity and cross-reactivity. Both of these factors affect the minimum detectable concentration and therefore the diagnostic error rate. The sensitivity in such tests is generally limited by label detection accuracy, association factor of the probe-analyte pair (for example an antibody-antigen pair), and the effective density of probe molecule (for example probe antibody) on the surface (as shown in FIG. 1). Other molecules in the biological sample can also affect the minimum detectable concentration by binding to the probe molecule (for example the primary antibody), or by physisorption of the analyte to the surface at the test site (as shown in FIG. 2). The detection agent (for example a secondary antibody) may also physisorb to the surface causing an increase in the background signal (as shown in FIG. 2). Solving the cross-reactivity and background problem can take a significant amount of time in the assay development of a new test and increases the cost and complexity of the overall test. The assay is typically optimized by finding the best reagents and conditions and also by manufacturing the most specific probe molecule (for example antibody). This results in a long development time, the infeasibility of tests in some cases, and a higher manufacturing cost. For example a typical development of an ELISA assay requires several scientists working for more than a year finding the correct antibody as part of the assay development. Cross-reactivity of the proteins may be the source of the failure of such an effort.

A biosensor providing a multiple site testing platform was thought to provide a solution to some of the above described limitations in assay development. US Published Patent Applications US2011/0091870 and US2012/0115236 (the contents of which are incorporated herein by reference in their entirety) describe such biosensors having multiple sites that could be subjected to different reaction conditions to modulate the binding of the biomolecular analyte (for example proteins) to the probe molecule. For example, the signal detected in a biosensor having four sites also can have several components, e.g. four. These four terms may correspond to the concentration of the biomarker of interest, concentration of interfering analytes in the sample that bind non-specifically to primary antibody (probe molecule) sites and prevent the biomarker to bind, concentration of interfering analytes in the sample that form a sandwich and produce wrong signal, and finally the concentration of interfering analytes in the sample that physisorb to the surface and produce wrong signal. Each term is also proportional to a binding efficiency factor, $\alpha_{ij}$, which is a function of the molecule affinities and other assay conditions, e.g., mass transport. By controlling the condition at each site separately, different sites will have different efficiency factors.

Accurate and precise control of the assay conditions at different sites to generate large changes in the binding efficiency factors is important in the performance of such biosensor as a detection system for a biomolecular analyte of interest. In US2014/0008244 (the content of which is incorporated herein by reference in its entirety) such biosensors and such methods are described that can be readily integrated with a CMOS, electrode array, or TFT based setup to generate large change in binding efficiencies between test sites in a biosensor having an array of multiple test sites. In order to accurately measure the biomolecular analyte of interest the biosensor requires a high degree of reliability and reproducibility. Variations in the modulation of the local pH due to repeated use of the biosensor and variations between subsequent measurements may decrease the accuracy of the determination of the biomolecular analyte of interest by such biosensor. As such the modulation of the pH at each site of the multisite array of the biosensor needs to be accurately controlled and variations in such pH modulation need to be corrected. Therefore, there is a need for a biosensor in which the pH can be accurately, reliably, and reproducibly controlled at each of the multisite array test sites.

General methods for measuring and controlling pH are known in the art. (Durst et al., "Hydrogen-Ion Activity," Kirk-Othmer Encyclopedia of Chemical Technology, pp. 1-15 (2009)). Active pH control of a solution in contact with an electrode surface has potential applications in protein-protein interactions, isoelectric focusing, electrophoresis, combinatorial pH studies of chemical and biochemical processes, DNA denaturation and renaturation, controlling enzymatic processes, cell manipulations, as a means for accelerating or inhibiting chemical reactions with high spatial and temporal resolution, or in other processes involving pH as a variable. For example, US2014/0008244 describes a biosensor capable of modulating the pH or ionic concentration gradient near electrodes in the biosensor in order to modulate the binding interactions of biological samples of interest. In another example, US2014/0274760 (hereby incorporated by reference in its entirety) describes an improved biosensor with increased accuracy, reliability, and reproducibility.

Attempts to control solution properties through electrochemical agents attached to the surface have been described. Electrochemically triggered release of biotin from a modified gold electrode surface via reduction and subsequent lactonization of quinone tether was demonstrated (Hodneland et al., "Biomolecular surfaces that release ligands under electrochemical control," J. Am. Chem. Soc. 122, pp. 4235-36 (2000)). Electrochemical control of self-assembly and release of antibodies from the surface into solution was achieved by reduction and oxidation of n-decanethiol-benzoquinones (Artzy-Schnirman et al., "Artzy-Schnirman et al., Nano Lett. 2008, 8:3398-3403," Nano Lett. 8, pp. 3398-3403 (2008)). Release of protons from a 3D layer of electroactive material was demonstrated by Frasconi et al. using materials composed of gold nanoparticles and thioanilines (Frasconi et al., "Electrochemically Stimulated pH Changes: A Route To Control Chemical Reactivity," J. Am. Chem. Soc. 132(6), pp. 2029-36 (2010)). Electrochemical oxidation of thioaniline groups produced protons that diffused from electrode surface into the surrounding solution, thus altering its pH.

Electrochemical pH modulation in biological solutions presents a significant challenge due to complex nature of the system. The limitations include: presence of buffer components that restrict pH changes, limitations on co-solvents that can be used, presence of strong nucleophiles, such as amines and thiols, and presence of interfering electrochemically active components, such as DNA bases, ascorbic acid and glutathione.

Quinones are one of the most widely studied classes of electrochemically active molecules (See Thomas Finley, "Quinones," Kirk-Othmer Encyclopedia of Chemical Technology, 1-35 (2005), which is incorporated by reference in its entirety. See also, Chambers, J. Q. Chem. Quinonoid Compd. 1974, Pt. 2:737-91; Chambers, J. Q. Chem. Quinonoid Compd. 1988, 2:719-57; Evans, D. H. Encycl. Electrochem. Elem. 1978, 12: 1-259). Hydroquinone/benzoquinone transformation has been used as a model system to produce proton gradients at electrode surface (Cannan et al., Electrochem. Communications 2002, 4:886-92). A combination of para-hydroquinone and anthraquinone was used for generation of acidic pH in organic solution as a first step of DNA synthesis, and organic base was added to the solution in order to confine the acidic pH to electrode surface (Maurer, PLOS One 2006, 1:e34). However, those systems cannot be adopted for use in biological solutions due to reactivity of benzoquinone (the product of hydroquinone oxidation) towards nucleophiles that are often present in biological systems, such as peptides, proteins and glutathione (Amaro et al., Chem Res Toxicol 1996, 9(3):623-629); and further due to the insufficient solubility of unsubstituted anthraquinone in water.

Electrochemical time of flight measurements have demonstrated that $H^+$ ions generated on electrodes will diffuse out (Slowinska et al., "An electrochemical time-of-flight technique with galvanostatic generation and potentiometric sensing," J. Electroanal. Chem. Vol. 554-555, pp. 61-69 (2003); Eisen et al., "Determination of the capacitance of solid-state potentiometric sensors: An electrochemical time-of-flight method," Anal. Chem. 78(18), pp. 6356-63 (2006)). It has also been shown that the open circuit potential of an electrode surface is a function of the ionic concentration in a solution, including the H concentration in the solution, and therefore of the pH of the solution (Yin et al., "Study of indium tin oxide thin film for separative extended gate ISFET," Mat. Chem. Phys. 70(1), pp. 12-16 (2001)). Similarly, the redox reaction rates of electrochemical species are also pH dependent (Quan et al., "Voltammetry of quinones in unbuffered aqueous solution: reassessing the roles of proton transfer and hydrogen bonding in the aqueous electrochemistry of quinones," J. Am. Chem. Soc. 129(42), pp. 12847-56 (2007)). There has also been work done on improving the pH sensitivity of an electrode by incorporation of novel pH sensitive coatings to improve the accuracy of pH sensing (Ge et al., "pH-sensing properties of poly (aniline) ultrathin films self-assembled on indium-tin oxide," Anal. Chem. 79(4), pp. 1401-10 (2007)).

Many life science applications (proteomics, genomics, microfluidics, cell culture, etc.) use glass slides as a substrate for performing experiments. Examples of glass slides include protein microarrays, lysate arrays, DNA microarrays and cell culture platforms. One use of a protein microarray is to analyze biological substances (e.g., blood serum) from patients with a specific disease in comparison to corresponding substances from healthy or control subjects. The biological substances are applied to a microarray containing many (often thousands of) human proteins. Antibodies in diseased substances may react (bind) with certain antigens in the microarray, thereby identifying the antigens as disease-specific biomarkers. In addition to protein detection, other types of detection such as colorimetric, chemiluminescence and fluorescence detection are also possible with glass slides.

Often the experiments are performed under aqueous conditions, in which a substance-of-interest is combined with water or a water-containing liquid and placed onto a slide for analysis. In many cases the presence of bubbles (formed of air or other gases) disturbs the experiment, adversely affecting the results. One example of an adverse effect is when a bubble causes the test solution to dry out. This can create a false binding event where the substance-of-interest (e.g., a biomolecular analyte) fails to bind with a molecule with which the biomolecular analyte is supposed to interact. Another example is where the bubbles change the effective flow rate of the test solution and the flow rate is being measured as part of the experiment. Therefore, it is desirable to detect bubbles and to output an indication of their presence, so that experiment results can be interpreted correctly.

One way to detect bubbles is to manually check each slide under a microscope. However, microscopy is not always practical because the field of view is typically limited to a small area of the slide, so that checking the entire slide is time-consuming. Additionally, the use of light to illuminate the slide under the microscope can sometimes have a destructive effect on the substance-of-interest.

SUMMARY OF THE INVENTION

Herein are provided such methods that can be integrated with for example a CMOS, electrode array, or TFT based biosensor to generate large changes in binding efficiencies between test sites in the biosensor having an array of multiple test sites. In particular, the current application provides methods to modulate the pH or ionic concentration near electrode surfaces of such biosensors in order to modulate the biomolecular interactions between a probe biomolecule and a biomolecular analyte of interest.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes thereon;

b) adding an electrochemically active agent, an enzyme, an enzyme substrate, a buffer inhibitor, or a combination thereof to the aqueous solution; and c) reacting the electrochemically active agent, the enzyme, the enzyme substrate, or a combination thereof in the aqueous solution to produce $H^+$ ion or $OH^-$ ions, or increasing the diffusion of $H^+$ ions or $OH^-$ ions with the buffer inhibitor, or inhibiting the interaction between $H^+$ ions or $OH^-$ ions and buffering salts with the buffer inhibitor.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes;

b) adding an electrochemically active agent to the aqueous solution; and c) oxidizing or reducing the electrochemically active agent.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes and one or more immobilized enzymes thereon;

b) adding an enzyme substrate to the aqueous solution; and c) enzymatically oxidizing or reducing the enzyme substrate.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising an electromagnet in an aqueous solution and a biomolecular interface layer having one or more immobilized probes;

b) adding one or more enzymes immobilized onto magnetic micro- or nano-particles to the aqueous solution;

c) adding an enzyme substrate to the aqueous solution; and d) enzymatically oxidizing or reducing the enzyme substrate.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes;

b) adding an enzyme to the aqueous solution; and c) reacting the enzyme at the electrode surface.

According to example embodiments, there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes;

b) adding a buffer inhibitor to the aqueous solution; and c) inhibiting the diffusion of $H^+$ ions or $OH^-$ ions or the interaction between $H^+$ ions or $OH^-$ ions and buffering salts.

According to example embodiments, there is provided a biosensor for use in detecting a biomolecule analyte comprising a multisite array of test sites in which the conditions for interacting with the biomolecule analyte can be varied independently, each test site comprising:

a) a support in an aqueous environment;

b) one or more electrodes; and c) a biomolecular interface layer having one or more immobilized probes and one or more immobilized enzymes.

According to example embodiments, there is provided a method for detecting a biomolecule analyte in a biological sample, the method comprises:

a) providing a biosensor comprising a multisite array of test sites in which the conditions for interacting with a biomolecule analyte can be varied independently, each test site comprising a support in an aqueous solution comprising a water-miscible organic co-solvent, e.g., acetonitrile, dimethyl sulfoxide (DMSO), dimethyl formamide (DMF), and N,N-dimethyl acetamide (DMAc), to facilitate the dissolution of an electrochemical active agent, the support comprising one or more electrodes or an electromagnet, and a biomolecular interface layer having one or more immobilized probes thereon;

b) adding in each test site an electrochemically active agent, an enzyme, an enzyme substrate, a buffer inhibitor, or a combination thereof to the aqueous solution;

c) reacting the electrochemically active agent, the enzyme, the enzyme substrate, or a combination thereof in the aqueous solution to produce $H^+$ ion or $OH^-$ ions, or increasing the diffusion of $H^+$ ions or $OH^-$ ions with the buffer inhibitor, or the inhibiting the interaction between $H^+$ ions or $OH^-$ ions and buffering salts with the buffer inhibitor;

d) adding a biological sample to each test site; and e) detecting the biomolecule analyte in each test site, wherein the amounts added in step b) and the reaction in step c) are varied between test sites in a subset array of test sites in order to obtain sets of test sites in which the pH or ionic concentration near the electrode surfaces in the test sites varies.

Also provided are devices and methods for accurately, reliably and reproducibly controlling the pH that can be integrated with for example a CMOS, electrode array, or TFT based biosensor having an array of multiple test sites. In particular, the current application provides methods to reliably and reproducibly modulate the pH or ionic concentration near electrode surfaces of such biosensors in order to modulate the biomolecular interactions between a probe biomolecule and a biomolecular analyte of interest. The device described herein can be used in a biosensor in order to repeatedly determine a biomolecular analyte of interest in a sample while maintaining a high degree of accuracy of the biosensor.

According to example embodiments, there is provided a device for use in a biosensor having a multisite array of test sites, the device comprising:
 (a) a support substrate supporting one or more electrodes; and
 (b) a biomolecular interface layer having immobilized pH sensitive Fluorescent Protein and one or more immobilized probes thereon.

According to example embodiments, there is provided biosensor comprising the device comprising:
 (a) a support substrate supporting one or more electrodes; and
 (b) a biomolecular interface layer having immobilized pH sensitive Fluorescent Protein and one or more immobilized probes thereon.

According to example embodiments, there is provided a method of modulating the pH or ionic concentration in a biosensor, the method comprising:
 a) providing a biosensor comprising a multisite array of test sites in which the conditions for interacting with a biomolecule analyte can be varied independently, the biosensor having a device comprising a support substrate supporting one or more electrodes, and a biomolecular interface layer having immobilized pH sensitive Fluorescent Protein and one or more immobilized probes thereon; and
 b) reacting at the one or more electrodes an electrochemically active agent in an aqueous solution to produce $H^+$ ion or $OH^-$ ions.

According to example embodiments, there is provided a method for detecting a biomolecule analyte in a biological sample, the method comprising:
 a) providing a biosensor comprising a multisite array of test sites in which the conditions for interacting with a biomolecule analyte can be varied independently, the biosensor having a device comprising a support substrate supporting one or more electrodes and a biomolecular interface layer having immobilized pH sensitive Fluorescent Protein and one or more immobilized probes thereon, and at each test site having an aqueous solution comprising a dilute phosphate buffer and an electrochemically active agent;
 b) at each test site electrochemically reacting the electrochemically active agent in an aqueous solution to produce $H^+$ ion or $OH^-$ ions, thereby modulating and controlling the pH at each test site;
 c) adding a biological sample to each test site; and
 d) detecting the biomolecule analyte in each test site,
 wherein the amounts of electrochemically active agent and the electrochemical reaction are varied between test sites in a subset array of test sites in order to obtain sets of test sites in which the pH or ionic concentration near electrode surfaces in the test sites varies, and wherein the pH at each test site is determined by the fluorescence intensity of the pH sensitive Fluorescent Protein.

Also provided is a system and method for detecting bubbles in an aqueous solution. The solution is placed onto a measurement area of a slide, the measurement area containing a plurality of electrodes configured to measure capacitance. According to example embodiments, the slide is configured to support measurements of at least one additional type of data in connection with an experiment involving a substance-of-interest contained in the solution. This allows the slide to be used for conventional testing purposes in addition to bubble detection. According to an example embodiment, one or more electrodes are configured for dual functioning so that the one or more electrodes help facilitate both the conventional testing function and the bubble detection.

According to example embodiments, the slide includes a control unit that measures capacitance values associated with individual ones of the electrodes and/or pairs of the electrodes. The control unit captures the capacitance value(s) for subsequent processing and allows for capturing of bubble detection relevant data, obviating the need to manually check the slide for bubbles.

According to example embodiments, the system and method include analyzing measured capacitances to identify a location of a bubble in the solution. In an example, bubbles are detected based on comparing the value of the capacitances to a threshold value or to other measured capacitances. This allows the location of the bubbles to be determined without user input.

According to example embodiments, the system and method involve displaying bubble locations graphically, preferably as a three-dimensional graph. This allows a user to quickly determine where bubbles are located, without having to manually interpret the measured capacitance values. The user can then determine, based on the bubble indications, whether to keep or discard additional data that is being measured as part of the experiment. In an example, the additional data is automatically invalidated by a computer processor in response to bubble detection, to further reduce user burden.

According to example embodiments, the system and method involve using the slide to adjust the pH level of the solution using at least some of the same electrodes that are used for measuring capacitance in connection with bubble detection. This allows for more efficient usage of the electrodes and provides an additional level of functionality to the slide.

According to example embodiments, the system and method include using a computer processor to perform at least some of the processing required by the system and method, prior to outputting the data to an external computer. The processor is powered by a small power source, on or connectable to the slide. The processor, in combination with the power source, allows routine processing to be performed in a power efficient manner.

Also provided are electrochemically active compositions having quinone derivatives where the reactivity between a nucleophile and the quinone derivative is reduced as compared to the reactivity between the nucleophile and an unsubstituted quinone from which quinone derivative is derived, and the composition is configured such that the pH of the composition is electrochemically modulated via the quinone derivative. The composition can be added to a solution and is suitable for electrochemical pH modulation in biological buffers. The present invention also provides methods of making the quinone derivatives and/or compositions, and uses thereof.

According to example embodiments, electrochemically active compositions are provided as an aqueous solution and optionally further comprise one or more additive selected from the group consisting of: an aqueous buffer, an organic solvent, an electrolyte, a buffer salt, a bioreagent, a biomolecule, a surfactant, a preservative, a cryoprotectant, and combinations thereof. According to example embodiments, the composition comprises one or more nucleophiles and a quinone derivative. The pH of the composition is able to be electrochemically modulated through electrochemically induced redox reactions of the quinone derivatives in solution.

According to example embodiments, methods for modifying unsubstituted quinones to reduce their reactivity with nucleophiles comprise substituting one or more hydrogen of the unsubstituted quinone with a substituent (R-group) to provide a quinone derivative with a reduced reactivity with nucleophiles compared to the reactivity between the unsubstituted quinone and the nucleophile.

According to example embodiments, methods for increasing the water solubility of a quinone comprise substituting one or more R groups of the quinone with a polar group to provide a water soluble quinone derivative. The polar group has atoms containing lone pair electrons and is capable of forming hydrogen bonds with water.

According to example embodiments, methods for synthesizing substituted methyl quinone comprise the following reaction steps: (i) reacting a starting material with a hydrogen halide in the presence of acetic acid and an aldehyde; (ii) reacting a material produced by step (i) with a nucleophile of structure R—X, where X is either OH, NH$_2$, NHR, SH, O$^-$, or S$^-$ and R is a substituent, (iii) reacting a material produced by step (ii) with an oxidizing agent; and (iv) reacting a material produced by step (iii) with a reducing agent.

According to example embodiments, methods of modulating the pH of a solution comprise providing to the solution any one of the quinone derivatives described above, or a combination thereof; providing an electrical current to the solution resulting in an electrochemical reaction that reduces or oxidizes the quinone derivative; measuring the pH of the solution; and modifying the electric current to modulate the pH of the solution.

According to example embodiments, methods for adjusting an oxidation/reduction potential of a quinone comprise substituting one or more hydrogen with an electron withdrawing or electron donating group.

Also provided are integrated systems for using electronics to change the pH of a solution close to an electrode in a controlled fashion. Moreover, the present invention provides control methods for the integrated system that allow for generating precisely controlled changes in the pH of a solution close to an electrode.

According to example embodiments, methods for changing the pH of a solution by electronic control comprise applying an electric source to the solution using two or more electrodes to electrochemically generate and/or consume hydrogen ions in the solution. The generation and/or consumption of the hydrogen ions are achieved by an electrochemical reaction of one or more redox active species in the solution.

According to example embodiments, methods for controlling the pH of a solution using two or more electrodes comprise obtaining an open circuit potential (OCP) of the two or more electrodes in the solution, while no electric input is being applied between the two or more electrodes, selecting an amount of electric input based on the OCP, and providing the selected amount of electric input to the solution between the two or more electrodes to change the pH of the solution.

According to example embodiments, methods for monitoring the pH of a solution using a sense electrode, a reference electrode, and a working electrode comprise selecting a target open circuit potential (OCP) for the solution, characterizing an OCP of the solution between the reference electrode and the sense electrode while no electric input is being applied to the working electrode, and iteratively performing the following steps: selecting an amount of electric input to be applied to the working electrode in order to minimize a difference between the OCP of the solution and the target OCP; and applying the amount of electric input to the working electrode to adjust the OCP of the solution.

According to example embodiments, a device for controlling the pH of a solution comprises a controller, two or more electrodes, and a solution containing one or more redox active species. The device is configured to obtain the open circuit potential (OCP) between the two or more electrodes in the solution to generate a OCP data and send the OCP data to the controller, and the controller is configured to iteratively perform the following steps: select an amount of electric input based on a difference between a target OCP and the obtained OCP data, apply the amount of electric input to the solution.

The present invention provides an electrochemically active composition comprising a quinone derivative, wherein:

a reactivity between a nucleophile and the quinone derivative is reduced compared to a reactivity between the nucleophile and an unsubstituted quinone from which the quinone derivative is derived, and the composition is configured such that the pH of the composition is electrochemically modulated via the quinone derivative.

In some embodiments of the present invention, the quinone derivative is defined by a chemical formula selected from the group consisting of:

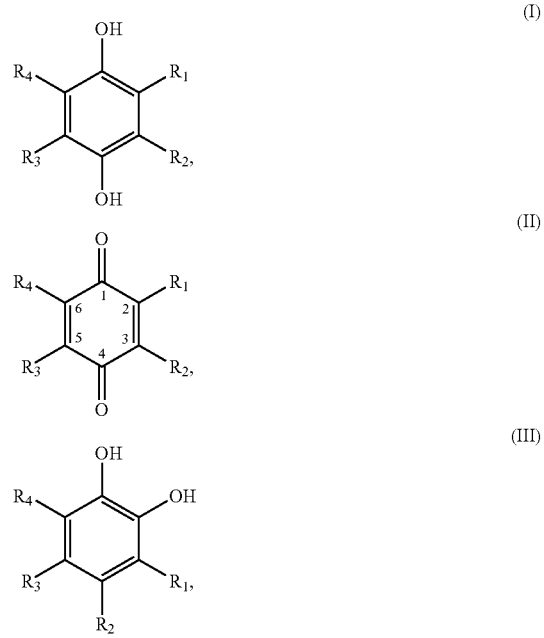

-continued (IV) 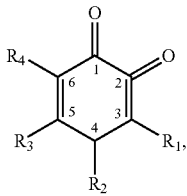

(V) 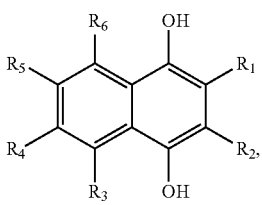

(VI) 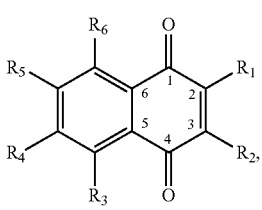

(VII) 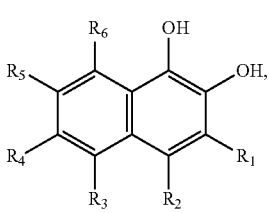

(VIII) 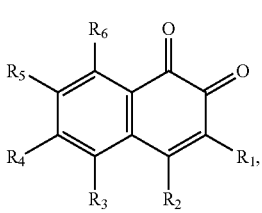

(IX) 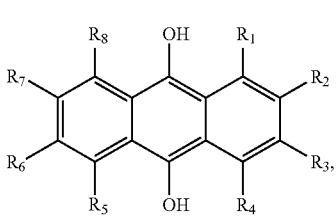

(X) 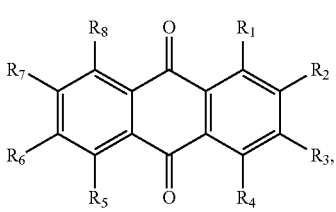

-continued

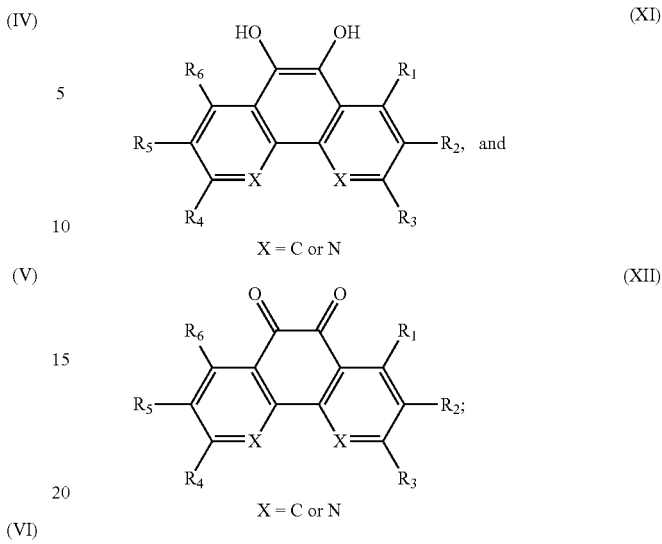

for chemical formulas I to XII, each R group is independently selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;

at least one of the R groups is not hydrogen;

M is any metal cation or $NH_4^+$;

n is an integer from 1 to $10^9$; and y is an integer from 1 to $10^9$.

In some embodiments of the present invention, all of the R groups of the quinone derivative are different from each other.

In some embodiments of the present invention, two or more of the R groups of the quinone derivative are the same.

In some embodiments of the present invention, the composition is an aqueous solution.

In some embodiments of the present invention, the composition further comprises an additive selected from the group consisting of: an aqueous buffer, an organic solvent, an electrolyte, a buffer salt, a bioreagent, a biomolecule, a surfactant, a preservative, a cryoprotectant, and combinations thereof.

In some embodiments of the present invention, the one or more nucleophiles are selected from the group consisting of: amines, thiols, amino acids, peptides, proteins, and combinations thereof.

In some embodiments of the present invention, the reactivity between the nucleophile and the quinone derivative is reduced compared to the reactivity between the nucleophile and the unsubstituted quinone from which the quinone derivative is derived due to:

(i) increased steric hindrance of a nucleophile binding site by one or more of the R groups;

(ii) elimination of the nucleophile binding site by covalent bonding between the nucleophile binding site and one of the R groups; or (iii) both (i) and (ii).

In some embodiments of the present invention, the quinone derivative has the chemical formula:

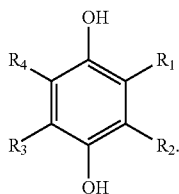

(I)

In some embodiments of the present invention, the quinone derivative has the chemical formula:

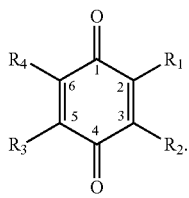

(II)

In some embodiments of the present invention, the quinone derivative has the chemical formula:

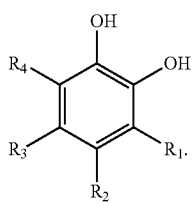

(III)

In some embodiments of the present invention, the quinone derivative has the chemical formula:

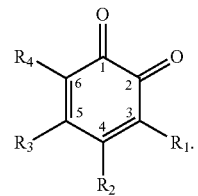

(IV)

In some embodiments of the present invention, the quinone derivative has the chemical formula:

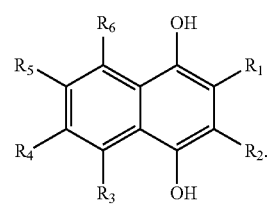

(V)

In some embodiments of the present invention, the quinone derivative has the chemical formula:

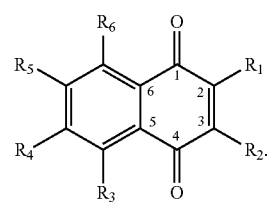

(VI)

In some embodiments of the present invention, the quinone derivative has the chemical formula:

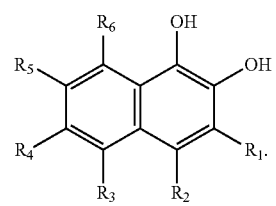

(VII)

In some embodiments of the present invention, the quinone derivative has the chemical formula:

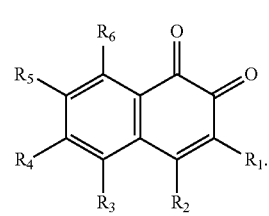

(VIII)

In some embodiments of the present invention, the quinone derivative has the chemical formula:

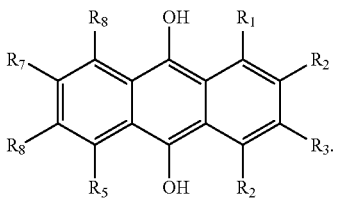

(IX)

In some embodiments of the present invention, the quinone derivative has the chemical formula:

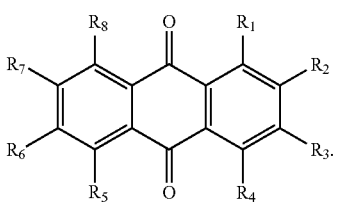

(X)

In some embodiments of the present invention, the quinone derivative has the chemical formula:

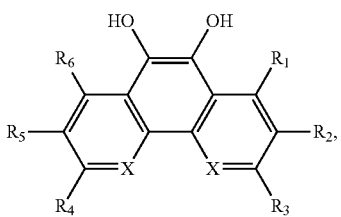

(XI)

In some embodiments of the present invention, the quinone derivative has the chemical formula:

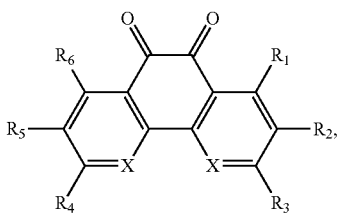

(XII)

wherein X is C or N.

The present invention provides a method comprising modifying a quinone having one or more R groups by substituting one or more of the R groups with a substituent to provide a quinone derivative, wherein:

the quinone derivative has a reduced reactivity with a nucleophile compared to a reactivity between the quinone and the nucleophile; and the substituent is independently selected from the group consisting of: H, $C_nH_{2n+1}$, Cl, F, I, Br, OM, $NO_2$, OH, $OC_nH_{2n}$, $OC_nH_{2n}$, $OC_nH_{2n}OH$, $O(C_nH_{2n}O)_yOH$, $O(C_nH_{2n}O)_y$ $OC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COCH_{2n+1}$, $NC_nH_{2n+1}COC_nH_{2n}OH$, $NC_nH_{2n+1}COCH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2l}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yOH$, $C_nH_{2n+1}O(C_nH_{2n}O)_yCOOH$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;

M is any metal cation or $NH_4$;

n is an integer from 1 to $10^9$; and y is an integer from 1 to $10^9$.

In some embodiments of the present invention, the reactivity between the quinone derivative and the nucleophile is less than the reactivity between the quinone and the nucleophile due to at least one of:

(i) elimination of a nucleophile binding site in the quinone derivative by covalent bonding between the substituent and the nucleophile binding site;

(ii) steric hindrance of the nucleophile binding site by the substituent; or (iii) both (i) and (ii).

In some embodiments of the present invention, the quinone derivative has a chemical formula:

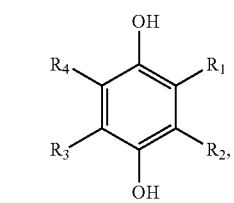

and at least one R group is not H.

In some embodiments of the present invention, the quinone derivative has a chemical formula:

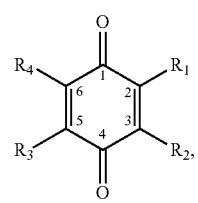

and at least one R group is not H.

1. In some embodiments of the present invention, the quinone derivative has a chemical formula:

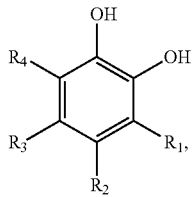

and at least one R group is not H.

In some embodiments of the present invention, the quinone derivative has a chemical formula:

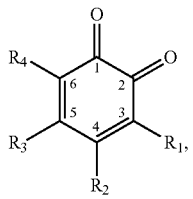

and at least one R group is not H.

In some embodiments of the present invention, the quinone derivative has a chemical formula:

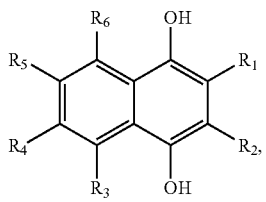

and at least one R group is not H.

In some embodiments of the present invention, the quinone derivative has a chemical formula:

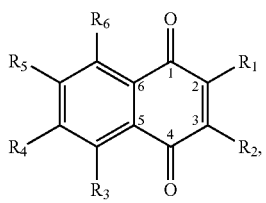

and at least one R group is not H.

In some embodiments of the present invention, the quinone derivative has a chemical formula:

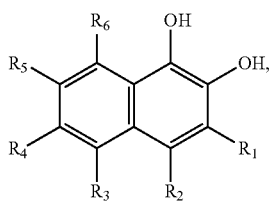

and at least one R group is not H.

In some embodiments of the present invention, the quinone derivative has a chemical formula:

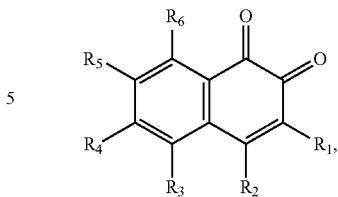

and at least one R group is not H.

In some embodiments of the present invention, the quinone derivative has a chemical formula:

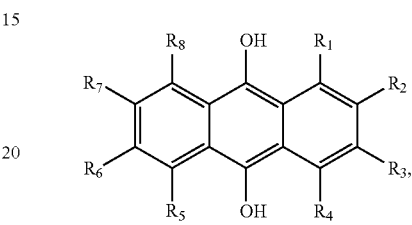

and at least one R group is not H.

In some embodiments of the present invention, the quinone derivative has a chemical formula:

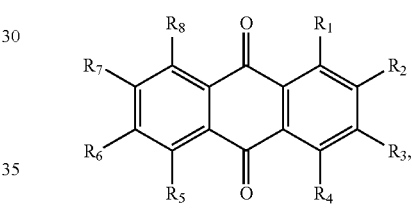

and at least one R group is not H.

In some embodiments of the present invention, the quinone derivative has a chemical formula:

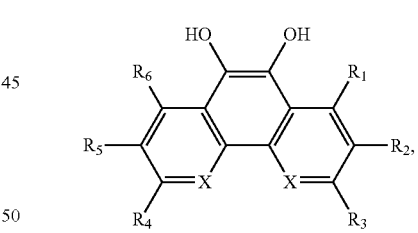

X is C or N, and at least one R group is not H.

In some embodiments of the present invention, the quinone derivative has a chemical formula:

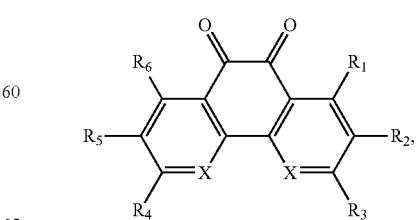

X is C or N, and at least one R group is not H.

In some embodiments of the present invention, the one or more R groups are substituted with a polar group.

In some embodiments of the present invention, the polar group has atoms containing lone pair electrons.

In some embodiments of the present invention, the polar group is capable of forming hydrogen bonds with water.

In some embodiments of the present invention, the polar group contains at least one of oxygen, nitrogen, and sulfur atoms.

In some embodiments of the present invention, the polar group is selected from the group consisting of: OH, $CH_2OH$, $OCH_3$, COOH, $SO_3H$, $NH_2$, $NH_3Cl$, ONa, a sugar, an amino acid, and a peptide.

The present invention provides a method of synthesizing substituted methyl quinone comprising:

(i) a halide substitution step of reacting a starting material with a hydrogen halide in the presence of acetic acid and an aldehyde;

(ii) reacting a material produced by step (i) with a nucleophile of structure R—X;

(iii) reacting a material produced by step (ii) with an oxidizing agent; and (iv) reacting a material produced by step (iii) with a reducing agent, wherein:

R is selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_y$COOH, $O(C_nH_{2n}O)_y$COOM, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_2O)_yOH$, $S(C_nH_{2n}O)_yOC_nH_{2n+1}$, $S(C_nH_{2n}O)_y$COOH, $S(C_nH_{2n}O)_y$COOM, $OC_nH_{2n}SH$, $O(C_nH_{2n}O)_y$SH, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})$ $C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_y$COOH, $C_nH_{2n+1}O(C_nH_{2n}O)_y$COOM, $C_nH_{2n+1}$COOH, $C_nH_{2n+1}$COOM, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_y$COOH, $C_nH_{2n+1}S(C_nH_{2n}O)_y$COOM, sugars, peptides, and amino acids;

M is any metal cation or $NH_4^+$;

n is an integer from 1 to $10^9$;

y is an integer from 1 to $10^9$; and

X is either OH, $NH_2$, NHR, SH, $O^-$, or $S^-$.

In some embodiments of the present invention, the starting material is dialkoxybenzene.

In some embodiments of the present invention, the result of the halide substitution step is an ortho-quinon, para-quinone, or a combination thereof.

In some embodiments of the present invention, a number of halide groups per molecule of the ortho-quinone or para-quinone is 1, 2, 3, or 4.

In some embodiments of the present invention, the starting material is dialkoxynaphthalene.

In some embodiments of the present invention, the result of the halide substitution step is an ortho-naphthoquinone, para-naphthoquinone, or a combination thereof.

In some embodiments of the present invention, a number of halide groups per molecule of the ortho-naphthoquinone or para-naphthoquinone is 1 or 2.

In some embodiments of the present invention, the hydrogen halide is selected from the group consisting of: HCl, HBr, HI, and combinations thereof.

In some embodiments of the present invention, the oxidizing agent is selected from the group consisting of: cerium ammonium nitrate, iodine, hydrogen peroxide, hypervalent iodine, iodobenzene diacetate, bromine compounds, and combinations thereof.

In some embodiments of the present invention, the reducing agent is selected from the group consisting of: sodium borohydrate, potassium borohydrate, sodium hydrosulfite, trichlorosilane, and combinations thereof.

The present invention provides, a method comprising:

a. providing a biosensor comprising a support in an solution, i. the support comprising one or more electrodes, and a biomolecule interface layer having one or more immobilized probes thereon;

ii. the solution comprising a quinone derivative;

b. adding a biomolecule analyte to the solution;

c. electrochemically reacting the quinone derivative using the one or more electrodes to produce an amount of $H^+$ ions and/or an amount of $OH^-$ ions, wherein the pH of the solution close to the one or more electrodes is controlled by the amount of $H^+$ ions and/or the amount of $OH^-$ ions produced;

d. collecting signals from the biosensor, e. wherein a reactivity between a nucleophile and the quinone derivative is reduced compared to a reactivity between the nucleophile and an unsubstituted quinone from which the quinone derivative is derived In some embodiments of the present invention, the quinone derivative is defined by a chemical formula selected from the group consisting of:

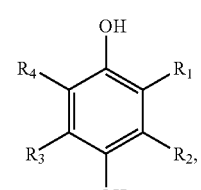

(I)

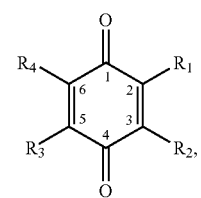

(II)

-continued

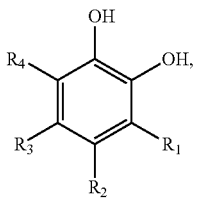
(III)

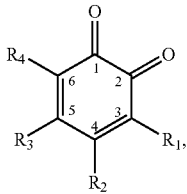
(IV)

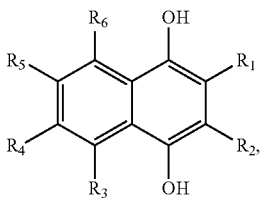
(V)

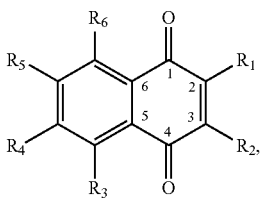
(VI)

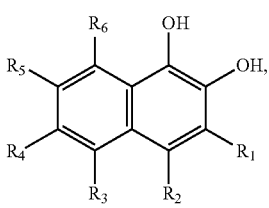
(VII)

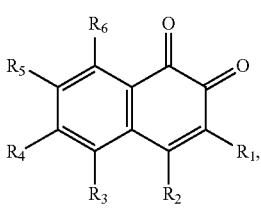
(VIII)

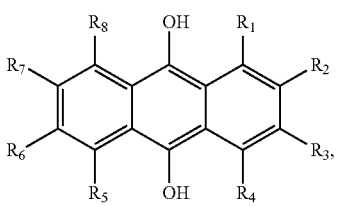
(IX)

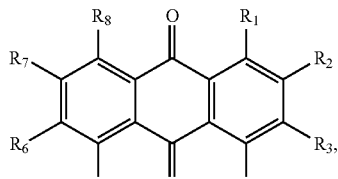
(X)

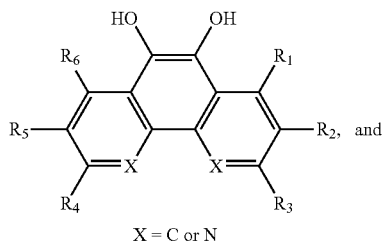
X = C or N
(XI)

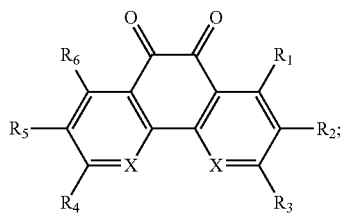
X = C or N
(XII)

for formulas I to XII, each R group is independently selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_2+1COC_nH_{2n}OH$, $NC_nH_{2n+1}COC_nH_{2n}NH_2$, $NC_nH_{2n+1}COC_nH_2SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;

at least one of the R groups is not hydrogen;

M is any metal cation or $NH_4^+$;

n is an integer from 1 to $10^9$; and y is an integer from 1 to $10^9$.

In some embodiments of the present invention, the pH of the solution before electrochemically reacting the quinone derivative using the one or more electrodes is 1 to 14.

In some embodiments of the present invention, the pH of the solution after electrochemically reacting the quinone derivative using the one or more electrodes is 1 to 14.

In some embodiments of the present invention, the solution contains one or more nucleophiles.

In some embodiments of the present invention, the one or more nucleophiles are selected from the group consisting of: amines, thiols, amino acids, peptides, proteins, and combinations thereof.

In some embodiments of the present invention, the solution contains a reduced quinone derivative and electrochemically reacting the quinone derivative results in an electrochemical oxidation reaction of the reduced quinone derivative to make the pH of the solution more acidic.

In some embodiments of the present invention, the concentration of the reduced quinone derivative is 0 to 1M.

In some embodiments of the present invention, the solution contains an oxidized quinone derivative and electrochemically reacting the quinone derivative results in an electrochemical reduction reaction of the oxidized quinone derivative to make the pH of the solution more basic.

In some embodiments of the present invention, the concentration of the oxidized quinone derivative is 0 to 1M.

In some embodiments of the present invention, the solution contains one or more buffer components provided in a concentration that is 0 to 1M.

In some embodiments of the present invention, the one or more buffer components are selected from the group consisting of: organic solvents, electrolytes, bioreagents, biomolecules, surfactants, and combinations thereof.

In some embodiments of the present invention, the method further comprises measuring the pH of the solution.

In some embodiments of the present invention, the pH is measured continuously.

In some embodiments of the present invention, the quinone derivative is electrochemically reacted by providing an amount of electric current.

In some embodiments of the present invention, the pH is measured before providing the amount of electric current.

In some embodiments of the present invention, the amount of electric current is selected based on the measured pH.

DETAILED DESCRIPTION

Figure 1:
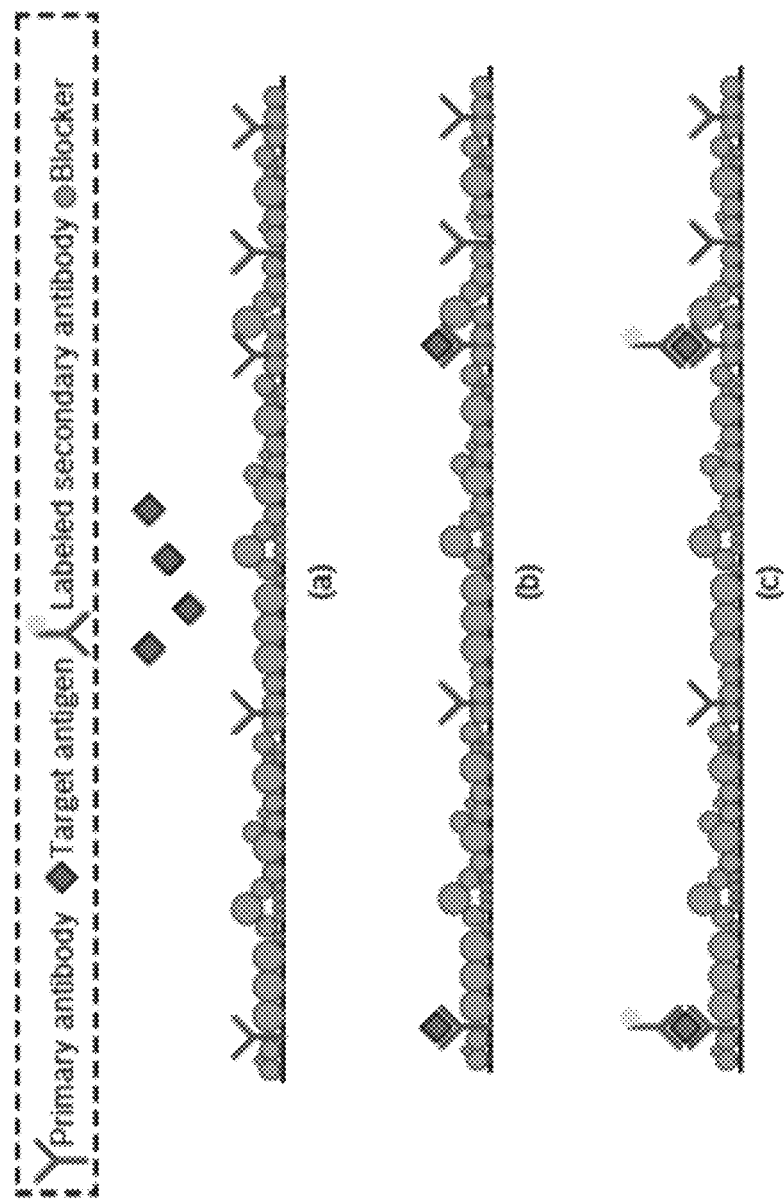
FIG. 1: Illustration of the steps of a typical and well known ELISA assay: a) Sample introduced to immobilized primary antibody on a blocked surface and incubated, b) Sample washed, and c) labeled secondary antibody is added. The number of labels is proportional to the concentration of target antigen.
Figure 2:
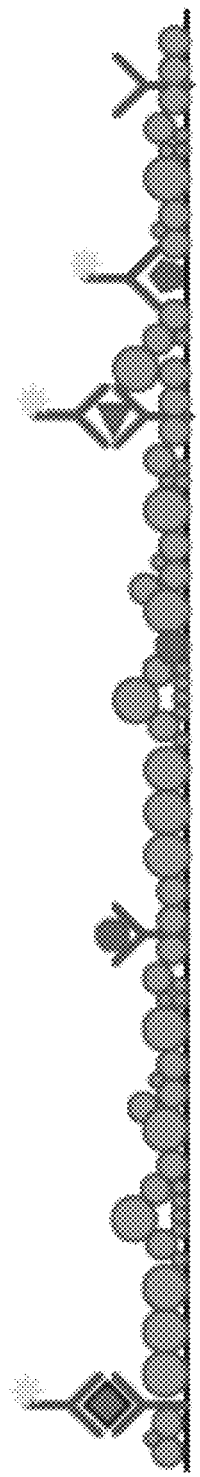
FIG. 2: Illustration of the undesired cross-reactivity. Molecules other than the antigen of interest (diamond) can bind to primary antibody or the surface and either create incorrect signal or prevent the antigen in forming a sandwich.

In order to vary the pH or ionic concentration gradient in a multisite array of test sites in a biosensor there is provided a method of modulating the pH or ionic concentration in a biosensor, the method comprising:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized probes thereon;

b) adding an electrochemically active agent, an enzyme, an enzyme substrate, a buffer inhibitor, or a combination thereof to the aqueous solution; and c) reacting the electrochemically active agent, the enzyme, the enzyme substrate, or a combination thereof in the aqueous solution to produce $H^+$ ion or $OH^-$ ions, or increasing the diffusion of $H^+$ ion or $OH^-$ ions with the buffering agent or inhibiting the interaction between $H^+$ ions or $OH^-$ ions and buffering salts with the buffer inhibitor.

In the above described method a local pH or ionic concentration gradient can be obtained in the various test sites in a multisite array biosensor. The variation of the local pH and/or ionic concentration gradient at the electrode, and in particular in the vicinity of the (biomolecular) probe in a biomolecular interface layer, over subsets of the multisite array of the biosensor, allows for modulating the binding efficiency of the (biomolecular) probe and an analyte to be tested from a biological sample. The analyte of interest, when bound to the (biomolecular) probe, can be then detected using a detection agent, such as for example a labeled secondary antibody. The modulation of binding efficiencies in a subset of a multisite array provides a method for the accurate determination of such analyte of interest.

The biosensor preferably comprises a multisite array of test sites as for example is described in US 2011/0091870. Such multisite array preferably includes a number of different subarrays/subsets of test sites. Each test sites represents a site for performing an analysis of a (biomolecular) analyte from a biological sample through the detection of the (biomolecular) analyte using a (biomolecular) probe. The analytical conditions in each test site in each of the subarrays/subsets may be varied to obtain a collection of varied signals that will result in multiple equations and multiple unknowns from which the concentration of the (biomolecular) analyte can be determined in order to obtain an accurate measurement of the (biomolecular) analyte.

The multiple unknowns in the obtained varied signals each includes a term that is proportional to a binding efficiency factor, $\alpha_{ij}$, and the concentrations of the various molecules in the biological sample binding that are detected at the test site. The multiple equations with multiple unknowns may be represented for example as follows, $$\begin{cases} S_1 = \alpha_{11} C_{an} - \alpha_{12} C_{j1} + \alpha_{13} C_{j2} + \alpha_{14} C_{j3} \\ S_2 = \alpha_{21} C_{an} - \alpha_{22} C_{j1} + \alpha_{23} C_{j2} + \alpha_{24} C_{j3} \\ S_3 = \alpha_{31} C_{an} - \alpha_{32} C_{j1} + \alpha_{33} C_{j2} + \alpha_{34} C_{j3} \\ S_4 = \alpha_{41} C_{an} - \alpha_{42} C_{j1} + \alpha_{43} C_{j2} + \alpha_{44} C_{j3} \end{cases} \Rightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal, from which collection of multiple equations the concentration of the targeted biomolecular analyte can be determined.

The number of subarrays/subsets, as well as the number of test sites within each subarray/subset may be varied, as needed to obtain such accurate measurement of the analyte. Some of these analytical conditions include parameters such as for example temperature, shear stress, and pressure. For example the temperature of the aqueous solution in which the biomolecular probe and analyte of interest in the biological sample interact can be varied using the electromagnetic heat at the test site. Another important condition for the interaction between the biomolecular probe and the analyte of interest is the pH or ionic concentration. The method described herein modulates this pH or ionic concentration in the local environment of the biomolecular probe in order to affect the binding efficiency in the vicinity of the biomolecular probe.

Figure 3:
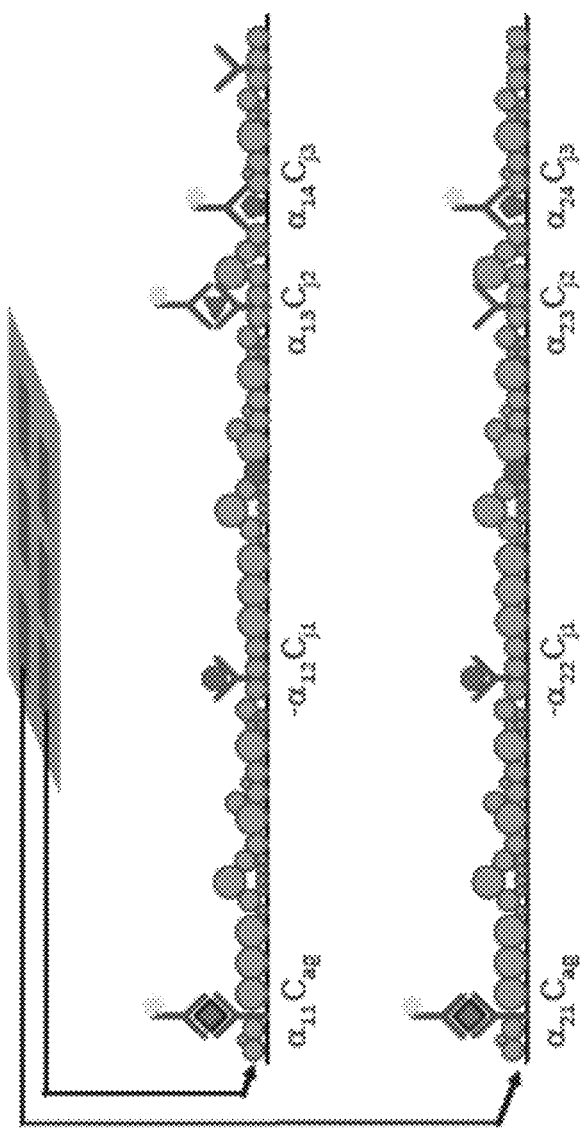
FIG. 3: Illustration of the multisite sensor and the components in the detected signal. The two schematics on the bottom correspond to two of the sites.
Figure 4:
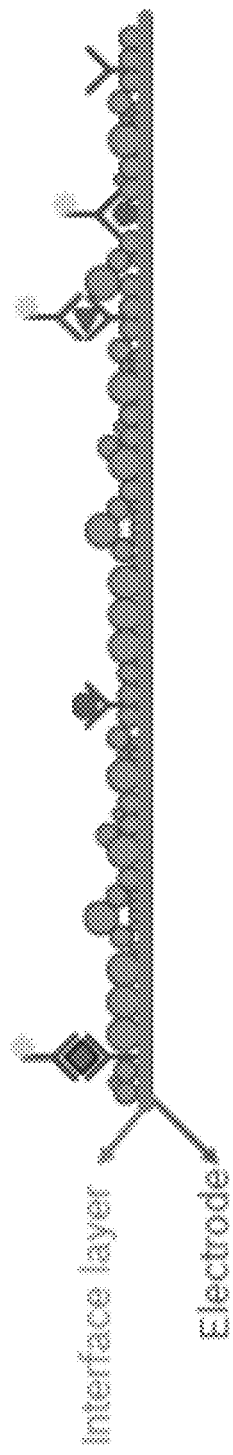
FIG. 4: Illustration of the composition of a sensor test site in a multisite sensor.

Each test site in the subarray/subset of the multiplesite array comprises a support onto which one or more electrodes are placed and onto which solid surface the biomolecular probe(s) are immobilized or bound (as shown in FIGS. 3 and 4). This immobilization of biomolecular probes to a solid surface or support assists in reducing the amount of probe needed for the analytical method and also localizes the detection area to make accurate measurements. The biomolecular probes are therefore attached to solid surfaces of the support and/or electrodes such as those of silicon, glass, metal and semiconductor materials (as shown in FIG. 4).

Figure 5:
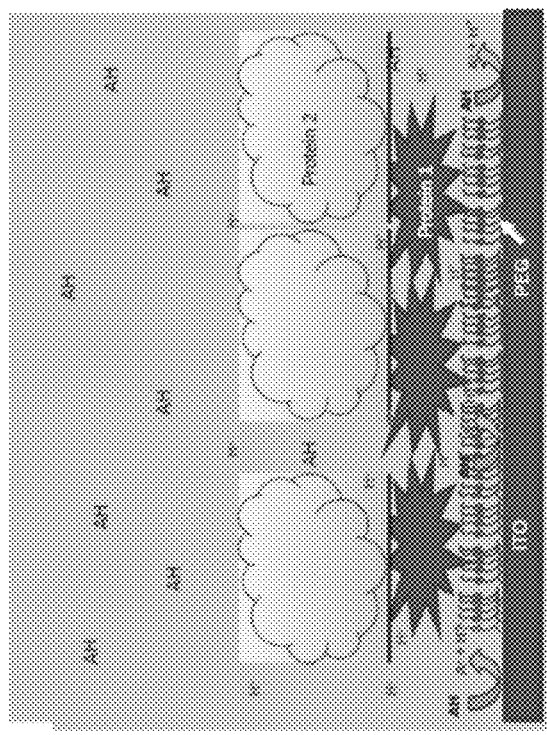
FIG. 5: Schematic of the pH change on an electrode surface using electrochemical method.

The biomolecular probe is attached or immobilized onto the support and/or electrode(s) within a biomolecular interface layer (as shown in FIG. 4). The biomolecular layer includes a layer of immobilized polymers, preferably a silane immobilized polyethylene glycol (PEG). Surface-immobilized polyethylene glycol (PEG) can be used to prevent non-specific adsorption of biomolecular analytes onto surfaces. At least a portion of the surface-immobilized PEG can comprise terminal functional groups such as N-hydroxysuccinimide (NHS) ester, maleimide, alkynes, azides, streptavidin or biotin that are capable of conjugating. The biomolecular probe may be immobilized by conjugating with the surface-immobilized PEG. It is important that the method used to change the pH does not impair the covalent binding of for example the PEG onto the surface of a solid support, or the linker that conjugated the biomolecular probe to the PEG (as shown in FIG. 5). The method of modulating the pH or ionic concentration as described herein can protect these surface chemistries, while affecting a pH/ionic concentration change in the environment of the biomolecular probe.

A suitable biomolecular probe can be a carbohydrate, a protein, a glycoprotein, a glycoconjugate, a nucleic acid, a cell, or a ligand for which the analyte of interest has a specific affinity. Such probe can for example be an antibody, an antibody fragment, a peptide, an oligonucleotide, a DNA oligonucleotide, a RNA oligonucleotide, a lipid, a lectin that binds with glycoproteins and glycolipids on the surface of a cell, a sugar, an agonist, or antagonist. In a specific example, the biomolecular probe is a protein antibody which interacts with an antigen that is present for example in a biological sample, the antigen being a biomolecular analyte of interest.

In the analytical method described herein the analyte of interest in a biological sample can be for example a protein, such as an antigen or enzyme or peptide, a whole cell, components of a cell membrane, a nucleic acid, such as DNA or RNA, or a DNA oligonucleotide, or a RNA oligonucleotide.

A biosensor comprising the device provided herein can be used in an analytical method for determining a biomolecular analyte of interest in a biological sample, which can be for example a protein, such as an antigen or enzyme or peptide, a whole cell, components of a cell membrane, a nucleic acid, such as DNA or RNA, or a DNA oligonucleotide, or a RNA oligonucleotide.

In such method a local pH or ionic concentration gradient can be obtained at various test sites in a multisite array biosensor. The variation of the local pH and/or ionic concentration gradient at the electrode, and in particular in the vicinity of the (biomolecular) probe in a biomolecular interface layer, over subsets of the multisite array of the biosensor, allows for modulating the binding efficiency of the (biomolecular) probe and an analyte to be tested from a biological sample. The analyte of interest, when bound to the (biomolecular) probe, can be then detected using a detection agent, such as for example a labeled secondary antibody. The modulation of binding efficiencies in a subset of a multisite array provides a method for the accurate determination of such analyte of interest.

The electrodes can be any electrode suitable in a biosensor for example indium tin oxide (ITO), gold, or silver electrodes. In a preferred embodiment the electrodes in the biosensor in the method described herein are indium tin oxide (ITO) electrodes.

This analytical method using a biosensor for detecting a biomolecule analyte in a biological sample according to one embodiment is a method which comprises the steps of:

a) providing a biosensor comprising a multisite array of test sites in which the conditions for interacting with a biomolecule analyte can be varied independently, each test site comprising a support in an aqueous solution, the support comprising one or more electrodes or an electromagnet, and a biomolecular interface layer having one or more immobilized detection agents thereon;

b) adding in each test site an electrochemically active agent, an enzyme, an enzyme substrate, a buffer inhibitor, or a combination thereof to the aqueous solution;

c) reacting the electrochemically active agent, the enzyme, the enzyme substrate, or combination thereof in the aqueous solution to produce $H^+$ ion or $OH^-$ ions, or increasing the diffusion of $H^+$ ions or $OH^-$ ions with the buffer inhibitor, or inhibiting the interaction between H' ions or $OH^-$ ions and buffering salts with the buffer inhibitor;

d) adding a biological sample to each test site; and e) detecting the biomolecule analyte in each test site, wherein the amounts added in step b) and the reaction in step c) are varied between test sites in a subset array of test sites in order to obtain sets of test sites in which the pH or ionic concentration near the electrode surfaces in the test sites varies. The aqueous solution comprises a water-miscible organic co-solvent, e.g., acetonitrile, dimethyl sulfoxide (DMSO), dimethyl formamide (DMF), and N,N-dimethyl acetamide (DMAc), to facilitate the dissolution of an electrochemical active agent. The amount of water-miscible organic solvent can range from 0.1 to 80% v/v, preferably from 0.1 to 10% v/v, most preferably from 1.0 to 5.0% v/v in respect to water in the aqueous solution. The analytical method hereby obtains in each subset of test sites a pH or ionic concentration gradient over the test sites in the subset in the vicinity of the biomolecular probe. The binding efficiencies of the analyte and any other molecule in the biological sample is thereby differently affected in each series of test sites in each subset.

In another embodiment there is provided an analytical method of using the device described herein in a biosensor to determine the presence and/or concentration of a biomolecular analyte of interest in a biological sample. This analytical method comprises a) providing a biosensor comprising a multisite array of test sites in which the conditions for interacting with a biomolecule analyte can be varied independently, the biosensor having a device comprising a support substrate supporting one or more electrodes and a biomolecular interface layer having immobilized pH sensitive Fluorescent Protein and one or more immobilized probes thereon, and at each test site having an aqueous solution comprising a dilute phosphate buffer and an electrochemically active agent;

b) at each test site electrochemically reacting the electrochemically active agent in an aqueous solution to produce $H^+$ ion or $OH^-$ ions, thereby modulating and controlling the pH at each test site;

c) adding a biological sample to each test site; and d) detecting the biomolecule analyte in each test site, wherein the amounts of electrochemically active agent and the electrochemical reaction are varied between test sites in a subset array of test sites in order to obtain sets of test sites in which the pH or ionic concentration near electrode surfaces in the test sites varies, and wherein the pH at each test site is determined by the fluorescence intensity of the pH sensitive Fluorescent Protein.

Figure 6:
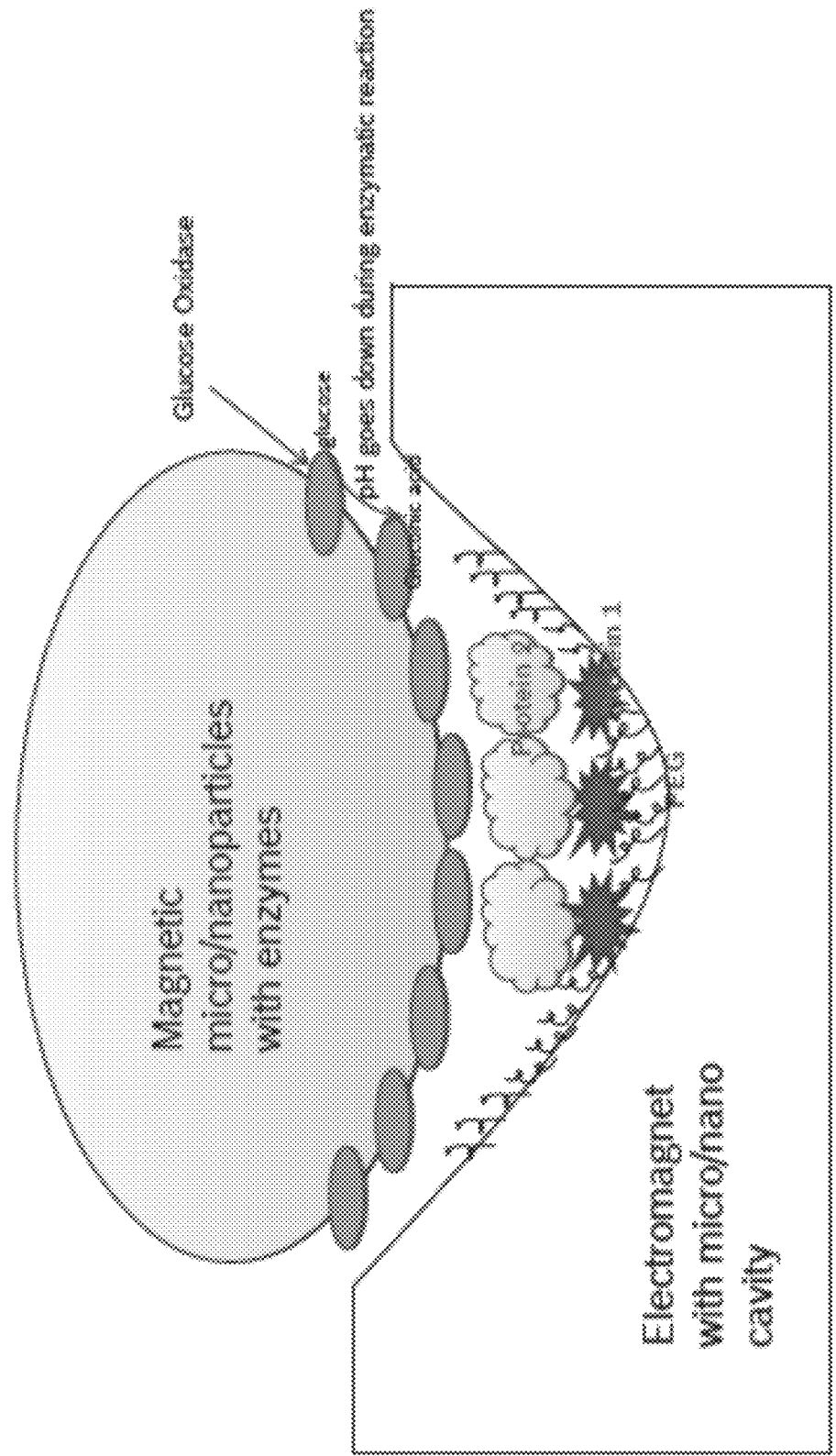
FIG. 6: Illustration of pH change by enzymatic reactions when they are brought close to the protein surface using magnetic micro/nanoparticles. The micro/nano cavity helps in localizing the pH change.

The biomolecular analyte can be detected using any suitable detection method. Known detection methods of such analyte include luminescence, fluorescence, colorimetric methods, electrochemical methods, impedance measurements, or magnetic induction measurements. In various of such methods the analyte binds to the immobilized biomolecular probe and a detection agent such as for example a secondary labeled probe that specifically binds to the analyte, bound to the immobilized probe, is introduced. This detection agent or secondary labeled probe gives rise to a detectable signal such as for example luminescence or fluorescence (as shown in FIGS. 5 and 6).

In such analytical method the pH of the solution surrounding the immobilize biomolecular probe has been known to influence the binding/activity between the probe and the analyte to a great extent. Concentration of other ions on surrounding proteins can also heavily influence the binding/activity. Herein are provided methods to modulate the pH and/or ionic concentration in the vicinity of the biomolecular probe immobilized close to a surface. The modulation of the pH near these solid surfaces also affect the non-specific interactions of the analyte to other molecules than the biomolecular probe and the interactions of other molecules in the solution of the biological sample with the biomolecular probe or analyte. The modulation of pH or ionic concentration however should not impair any of the surface chemistries, such as those that immobilize the biomolecular probe to its solid support in a test site of a multisite array in the biosensor. The method of modulating the pH or ionic concentration as described herein can protect these surface chemistries, while affecting a pH/ionic concentration change in the environment of the biomolecular probe.

Surface chemistry compatibility is an important consideration that should be noted when the methods described herein are practiced. pH change is caused by changes in hydrogen ion or hydroxyl ion concentrations. A variety of chemical reactions taken place at electrode-liquid, electrode-cross linker, cross linker-protein, and protein-protein interfaces as shown in FIG. 5 can also become a hindrance to pH changes happening near the solid surfaces to reach the proteins on top of them. They can simply act as diffusion barriers for the ions and hinder the pH changes around the biomolecular probes and analytes. These methods of modulating the pH or ionic concentration described herein helps in maximizing the changes in hydrogen or hydroxyl ion concentration so that they can overcome any diffusion barrier imposed by the surface chemistry.

Another important aspect is the buffering capacity of the solution in contact with the solid interface. The buffering effect can be large enough that the pH change at the interface would never reach the biomolecular probes that are immobilized away from it. The distance can vary based on the biomolecular interface layer deposited on top of the solid interface. Such biomolecular interface layer may have a thickness of 300 nm or less, preferable between 1-150 nm, even more preferably between 5-100 nm. As such the distance between the solid interface and the biomolecular probe within the biomolecular interface layer can range between 0.1-300 nm. Use of buffer inhibitors in the solution or on the surface that extend the pH change on the electrode interface to reach the interacting probe-analyte pair may contribute to modulating the pH or ionic concentration in the vicinity of the biomolecular probe.

Following are examples of methods for modulating the pH/ionic concentration at the solid-liquid interfaces. These include: 1) the electrochemical generation of ions at electrode surfaces by adding an electrochemically active species to the solution which generates ions of interest (e.g., $H^+$, $Mg^+$, $OH^-$) upon electrochemical oxidation/reduction; 2) bringing enzymes close to the site of interest, which release such ions of interest from an enzyme substrate that is reacted with the enzyme; 3) the introduction of buffer inhibitors, for example, by mixing polymers that selectively reduce the diffusion rate of ions in the solution (e.g., phosphate). U.S. Pat. No. 7,948,015 describes the use of such inhibitors for applications in which measuring small local pH changes is of interest (e.g., in DNA sequencing). However in the methods of locally modulating the pH similar inhibitors can be used in order to extend the local pH changes further away from the electrode-liquid interface; and 4) the redistribution of preexisting ions near the electrode surface due to electrostatic forces.

In one embodiment of a method for modulating the pH or ionic concentration in a biosensor as described herein an electrochemically active agent is added to the aqueous solution at a test site in a multisite array, wherein the test site has a biomolecular interface layer comprising a biomolecular probe or detection agent and oxidizing or reducing the electrochemically active agent. The electrochemically active agent may be added at a concentration of 1 nM to 100 mM, preferably at a concentration between 10 nM and 10 mM, more preferably at a concentration of 100 nM and 5 mM. The electrochemically active agent may be electro-oxidized or electro-reduced at an electrode potential in the range of −2V to +2V (vs. Ag/AgCl reference electrode). Preferably the electrode potential is in the range of −1V to +1V, even more preferably the electrode potential is in the range of −0.5V to +0.5V. The voltage required to drive the redox reaction can be used as a real time feedback method to monitor pH that is produced at the electrode surface.

The device provided herein and used in a biosensor comprises such array of multiple test sites in solution in order to modulate the pH at each test site and to determine the presence and concentration of a biomolecular analyte of interest in a biological sample. In such use the device is in contact with an aqueous solution comprising a phosphate buffer, preferably a diluted phosphate buffer which preferably has a concentration of 0.1 mM to 100 mM. In a preferred embodiment the pH of the diluted phosphate buffer is between 5 and 8, preferably between 7 and 8, and more preferably between 7 and 7.5.

Modulation of the pH or ionic concentration on a device in a biosensor described herein by electrochemical reaction at the one or more electrode may be carried out in a galvanostatic mode or potentiostatic mode. In addition, any type of electrical pulse may be applied on the electrodes of the device in the method for modulating the pH. Such pulse may be in the form of an annealing pulse and may vary by pulse frequency, pulse width, and pulse shape. In an annealing pulse a sufficient voltage is applied to change the pH to such that non-covently bound molecules from the biological sample are removed from the device in the biosensor. Such annealing pulse eliminates or reduces the need for washing the substrate following first contact with a sample in order to remove non-covalently bound material. Another advantage is that the annealing pulse may be more efficient to remove such non-covalently bound material from the device than a simple washing. A preferred pulse width for modulating the pH is in the range of 1 nanosecond to 60 minutes.

The aqueous solution may further comprise one or more additional electrolytes, such as for example sodium sulfate, or any other suitable strong electrolyte. Preferably, the additional electrolyte is selected from sodium sulfate, sodium or potassium chloride, sodium or potassium bromide, sodium or potassium iodide, sodium or potassium perchlorate, sodium or potassium nitrate, tetraalkylammonium bromide and tetraalkylammonium iodide. Buffer-inhibitors may also be used in the aqueous solution. Suitable buffer inhibitors may be selected from poly(allylamine hydrochloride), poly (diallyldimethyl ammonium chloride), poly(vinylpyrroldone), poly(ethyleneimine), poly(vinylamine), poly(4-vinylpyridine) and tris(2-carboxyethyl)phosphine hydrochloride. When used in a method to modulate the pH such as described in co-pending U.S. patent application Ser. No. 13/543,300 the aqueous solution preferably also comprises a water-miscible organic co-solvent selected from the groups consisting of acetonitrile, dimethyl sulfoxide (DMSO), dimethyl formamide (DMF), N,N-dimethyl acetamide (DMAc), and mixtures thereof.

Suitable electrochemically active agents include dopamine hydrochloride, ascorbic acid, phenol and derivatives, benzoquinones and derivatives, for example, 2,5-dihydroxy-1,4-benzoquinone, 2,3,5,6-tetrahydroxy-1,4-benzoquinone and 2,6-dichloroquinone-4-chloroimide; naphthoquinones and derivatives, for example, hydroxy-1,4-naphthoquinone, 5,8-dihydroxy-1,4-naphthoquinone, and potassium 1,4-naphthoquinone-2-sulfonate; and 9,10-anthraquinone and derivatives, for example, sodium anthraquinone-2-carboxylate, potassium 9,10-anthraquinone-2,6-disulfonate. Preferably the concentration of the electrochemically active agent in the aqueous solution is from 1 nM to 100 mM.

In another embodiment of a method for modulating the pH or ionic concentration in a biosensor, an enzyme is immobilized in a biomolecular interface layer also having one or more immobilized biomolecular probers. An enzyme substrate is then added to the aqueous solution at a test site in a multisite array, wherein the test site has the biomolecular interface layer and enzymatically oxidizing the enzyme substrate.

In another embodiment is provided a method of modulating the pH using the device in a biosensor. The method of modulating the pH or ionic concentration in a biosensor comprises:
  a) providing a biosensor including one or more devices as described herein comprising a multisite array of test sites in which the conditions for interacting with a biomolecule analyte can be varied independently; and
  b) reacting at the one or more electrodes an electrochemically active agent in an aqueous solution to produce H' ion or $OH^-$ ions.

In the method the concentration of the electrochemically active agent in the aqueous solution is preferably from 1 nM to 100 mM.

In another embodiment of a method for modulating the pH or ionic concentration, the method comprises:
  a) providing a biosensor comprising an electromagnet in an aqueous solution and a biomolecular interface layer having one or more immobilized detection agents;

b) adding one or more enzymes immobilized onto magnetic micro- or nano-particles to the aqueous solution;

c) adding an enzyme substrate to the aqueous solution; and d) enzymatically oxidizing the enzyme substrate.

Suitable enzymes for immobilization in the biomolecular interface layer or onto the magnetic micro- or nano-particles include for example oxidases, ureases, or dehydrogenases. Such immobilized oxidase is for example a glucose oxidase and the enzyme substrate is glucose. The amounts of immobilized enzyme and enzyme substrate added can be varied in the different test sites in each of the subsets of the multisite array so as to provide a pH or ionic concentration gradient in the such subset of the multisite array.

Alternatively the enzyme is not immobilized onto a solid surface such as in the above methods being immobilized into a biomolecular interface layer or onto a magnetic micro- or nano-particle but is added to the aqueous solution in the test sites of subsets of a multisite array. Through electrolysis the enzyme undergoes a redox reaction at the electrode surface and perturbs the local pH.

In each of these embodiments the pH or ionic concentration can be further modulated by adding a buffer inhibitor to the aqueous solution. Such addition of a buffer inhibitor either assists in diffusing the produced ions of interest to the location of the biomolecular probe or detection agent or inhibits the interaction of such produced ions with buffering salts. Alternatively, in the method of modulating the pH or ionic concentration in a biosensor as described herein, the buffer inhibitor is added to the aqueous solution of the test site of subsets of a multisite array in the absence of an electrochemical active agent or immobilized enzyme. In such embodiment the buffer inhibitor is added to the aqueous solution, and facilitates the diffusion of $H^+$ ions or $OH^-$ ions that are produced at the electrodes in the test site or inhibits the interaction between $H^+$ ions or $OH^-$ ions and buffering salts.

Suitable buffer inhibitors include soluble polymers selected from poly(allylamine hydrochloride), poly (diallyldimethyl ammonium chloride), poly(vinylpyrrolidone), poly(ethyleneimine), poly(vinylamine), poly(4-vinylpyridine) and tris(2-carboxyethyl)phosphine hydrochloride. The amounts of buffer inhibitor added can be varied in the different test sites in each of the subsets of the multisite array so as to provide a pH or ionic concentration gradient in the such subset of the multisite array.

When methods for modulating the pH in a biosensor having a multisite array of test sites are used in a biosensor the accuracy, reliability and reproducibility of the modulation of the pH at each test site is important. However the modulation of the pH at each test site may vary between subsequent uses. In order to accurately determine the amount of a biomolecular analyte of interest in a sample using the biosensor and method described above the pH at each test site needs to be accurately modulated or controlled. The device provided herein allows for accurate determination and control of the pH at each test site in such biosensor, the device comprising:

(a) a support substrate supporting one or more electrodes; and (b) a biomolecular interface layer having immobilized pH sensitive Fluorescent Protein and one or more immobilized probes thereon.

The support substrate in the device described herein is preferably a glass or plastic substrate but also be any other non-glass substrate.

Figure 10:
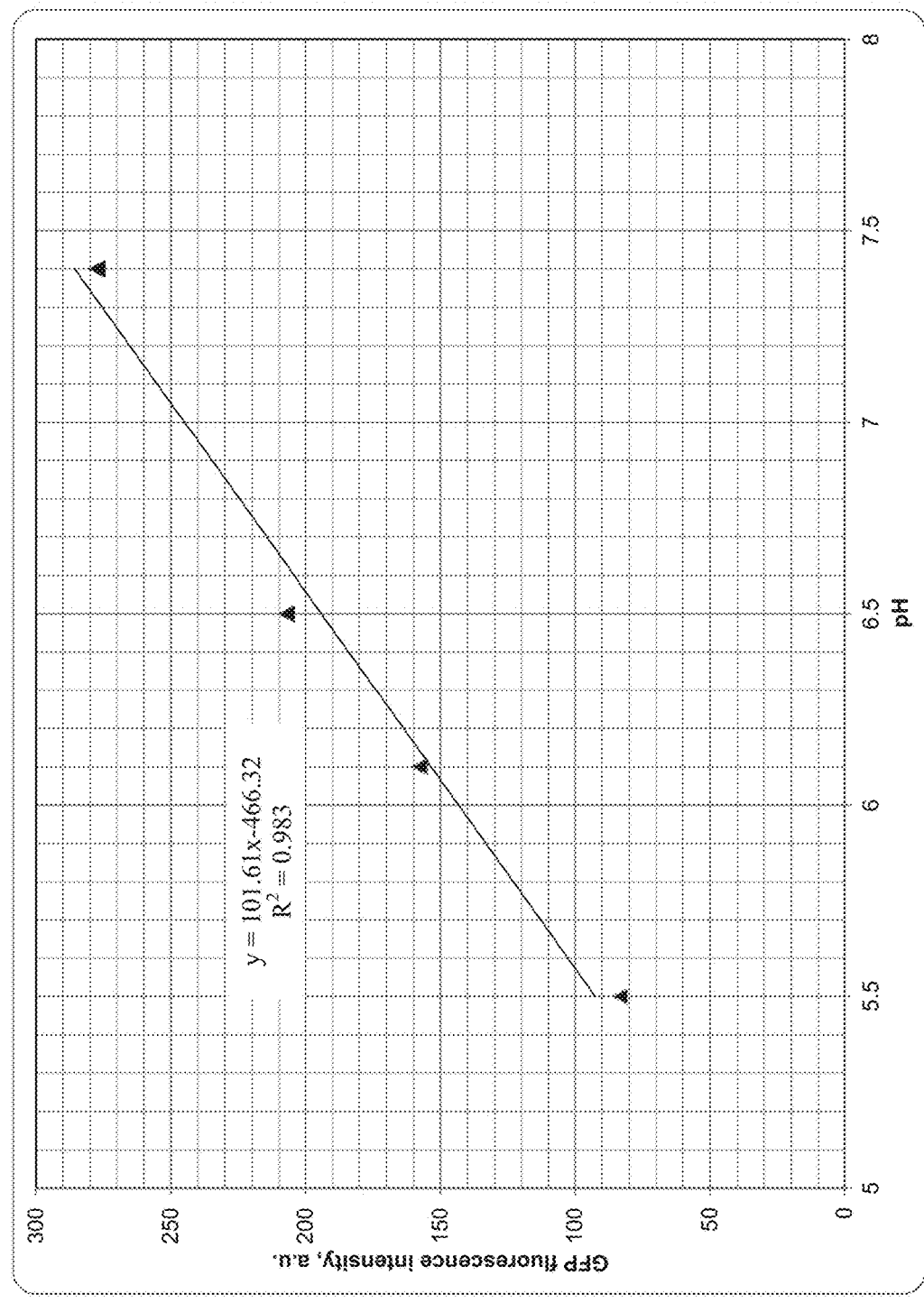
FIG. 10: shows the change in the fluorescence intensity of GFP covalently bound to the PEG-coated ITO in response to the change in solution pH. The solution pH was adjusted by adding HCl to a dilute phosphate buffer (pH 7.4).

The immobilized pH sensitive fluorescent protein allows for sensing the pH at an electrode once the electrode (working electrode) causes modulation of the pH at a particular test site such as a test site in a multisite array. The fluorescence intensity of the fluorescent protein changes due to modulation of the pH. The change in fluorescence intensity of the fluorescent protein is proportional to the change in the pH (there is a linear relationship between the pH and the fluorescence intensity). Therefore, as is also shown in FIG. 10, the pH value at each location at any time when the biosensor is in use can be readily obtained by correlating the fluorescence intensity of the fluorescent protein with the pH. An accurate calibration of the correlation between pH and fluorescence intensity may be carried out before or during use of the biosensor. When the calibration is carried out during use of the biosensor one or more test sites within a multisite array may be dedicated to calibration of the fluorescence intensity to pH correlation. When the pH is no longer modulated at such test site by the electrode (working electrode) the fluorescence intensity of the immobilized fluorescent protein reverts back to its intensity before a current was applied through the electrode.

Figure 12:
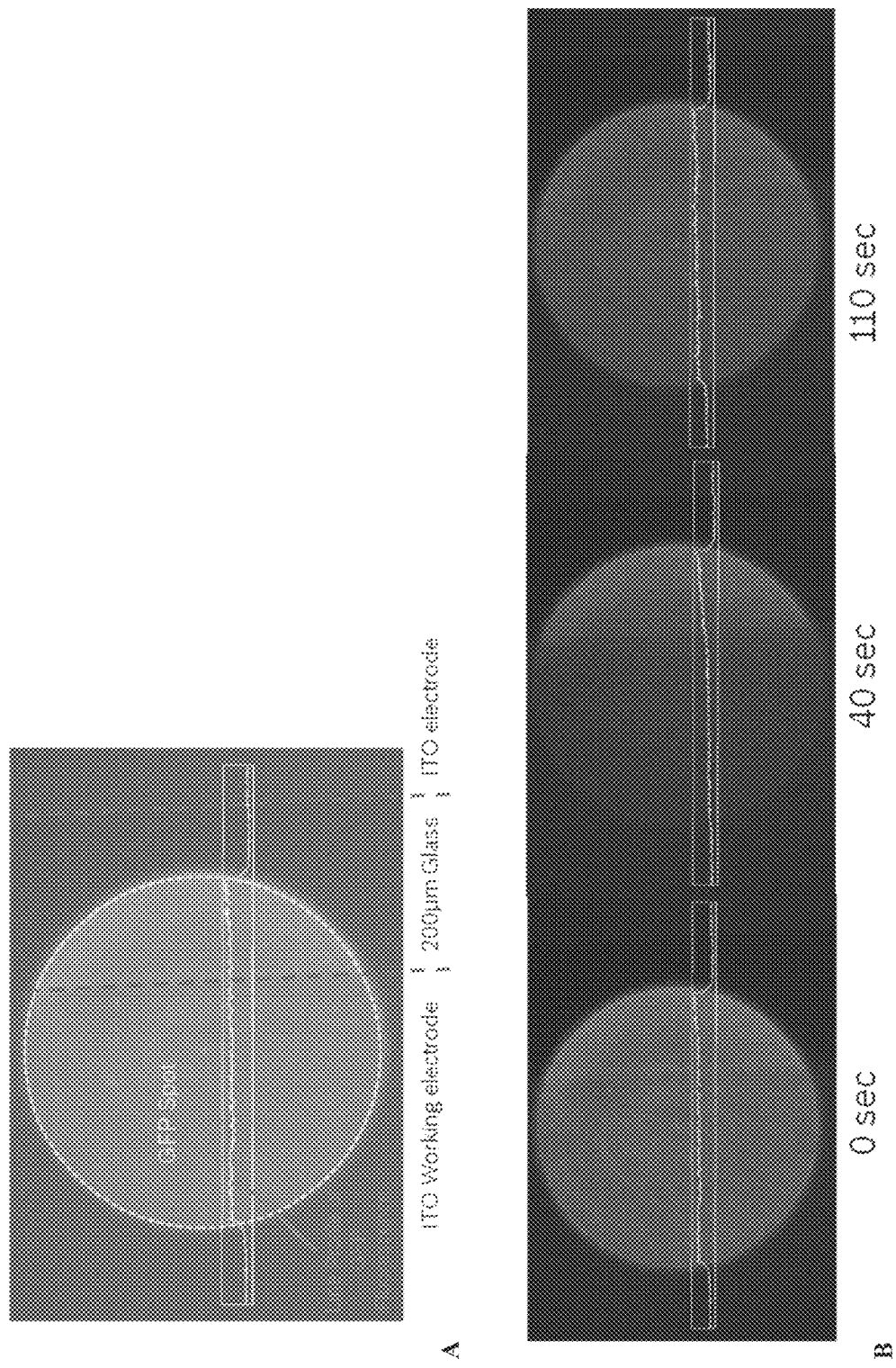
FIG. 12: illustrates the visual changes in the GFP spot before, during and after pH modulation experiment. A, the profile of fluorescence intensity across the spot is shown. B, the changes in the GFP spot fluorescence intensity are shown before (0 sec), during (40 sec), and after (110 sec) applying a current through an electrode.
Figure 13:
FIG. 13: shows a glass slide with an ASIC chip interfaced to transparent ITO electrodes.

Preferably, the immobilized fluorescent protein is selected from an immobilized green fluorescent protein, an immobilized yellow fluorescent protein, and an immobilized cyan fluorescent protein. More preferably, the immobilized fluorescent protein is immobilized Green Fluorescent Protein (GFP). In an alternative embodiment immobilized pH sensitive dyes may be used on the support substrate instead of an immobilized pH sensitive fluorescent protein. In another alternative embodiment immobilized pH sensitive binding proteins may be used on the substrate instead of an immobilized pH sensitive fluorescent protein. In a multisite array of test sites in a biosensor the immobilized fluorescent protein covers on the substrate an area that is also covered by an electrode and an area that is not covered with an electrode. The electrode covered by the immobilized fluorescent protein is either a working electrode or a counter electrode. Preferably, the immobilized fluorescent protein is applied onto the substrate as distinct spots, wherein each spot overlaps with only one test site and an area not covered by an electrode as shown in FIG. 12A. The presence of fluorescent protein on an area that is not covered by an electrode allows for the determination, within the biosensor, of fluorescence intensity when the pH is not modulated by the electrode. This fluorescence intensity can be used as a standard and control in determining whether, after ceasing modulation of the pH by an electrode the fluorescence intensity will revert back to its original intensity. Accordingly, in a method for detecting a biomolecular analyte in a biological using the device, the fluorescent protein not located on or near an electrode can be used as an internal reference for signal normalization.

The device includes one or more counter electrodes and one or more working electrodes. In the device one or more electrodes can be arranged in a multisite array, each site of the multisite array comprising a working electrode and/or counter electrode. The electrodes can be any electrode suitable in a biosensor for example indium tin oxide (ITO), gold, or silver electrodes. In a preferred embodiment the electrodes in the device are indium tin oxide (ITO) electrodes. In an alternative embodiment the working electrode is an indium tin oxide electrode and the counter electrode(s) is selected from an indium oxide electrode, a gold electrode, a platinum electrode, a silver electrode, and a carbon electrode.

The electrodes in the device may be used either for modulating the pH or as sensing electrodes or both. In the device or biosensor using the device, the one or more electrodes are connected to an electronic board via pogo-pins, a chip on foil via z-axis adhesive, or a chip on the substrate. The electronic board or chip are powered by a printed battery, a small battery bound to the substrate, a magnetically coupled power transfer using coils on the substrate, or a rf-coupled power transfer using coils on the substrate.

Figure 9:
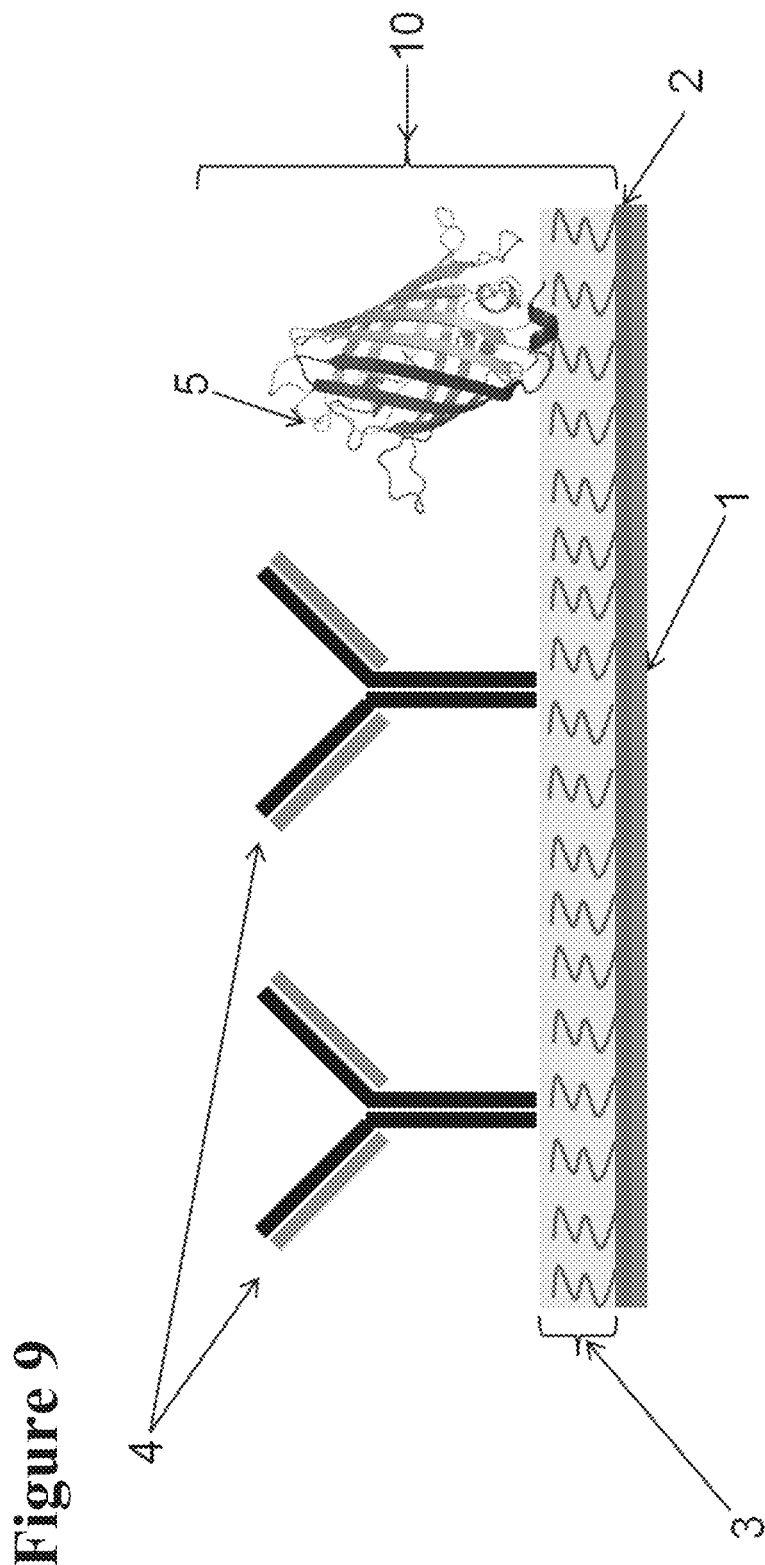
FIG. 9: Illustration of a substrate (glass or plastic) (1) with an array of electrodes (2) onto which a biomolecular interface layer (10) is applied which include fluorescence protein (such as Green Fluorescence Protein (GFP)) spots (5), and immobilized probes (4), immobilized using a polyethylene glycol (PEG) linker (3).

The following description is an illustration of a specific embodiment which may be modified within the scope of the description as would be understood from the prevailing knowledge. FIG. 9, shows a side view of a part of the device which includes a substrate (1) for example glass or plastic. One or more electrodes (2) are covered onto the substrate (1) which is also covered with a biomolecular interface layer (10). The biomolecular interface layer (10) comprises immobilized PEG (3), immobilized probe (4) and immobilized pH sensitive fluorescent protein in the form of Green Fluorescent Protein spots (5). The GFP spots (5) overlap with an electrode (2) and an area that is not covered by an electrode. The electrodes (2) and the GFP spots (5) are arranged in a multisite array so as to provide multiple test sites on the device.

The location of luminescence signals generated luminescent molecules can be controlled by directly controlling the location of the luminescent molecules themselves. This includes for example immobilizing the luminescent molecule. However, by incorporating the ability to control the pH of a solution near an electrode with pH sensitive luminescent molecules the location of luminescence signals generated by free floating luminescent molecules can also be controlled.

Example embodiments of the present invention relate to the detection of bubbles in glass slides, on which slides an aqueous solution is placed for analysis. However, the example embodiments may also be applied towards other applications in which it is desirable to detect the presence of bubbles. In particular, although the capacitance based detection techniques are described herein in connection with the capacitive properties of water, these techniques may also be applied to other liquids for which the capacitive properties are known.

Figure 14:
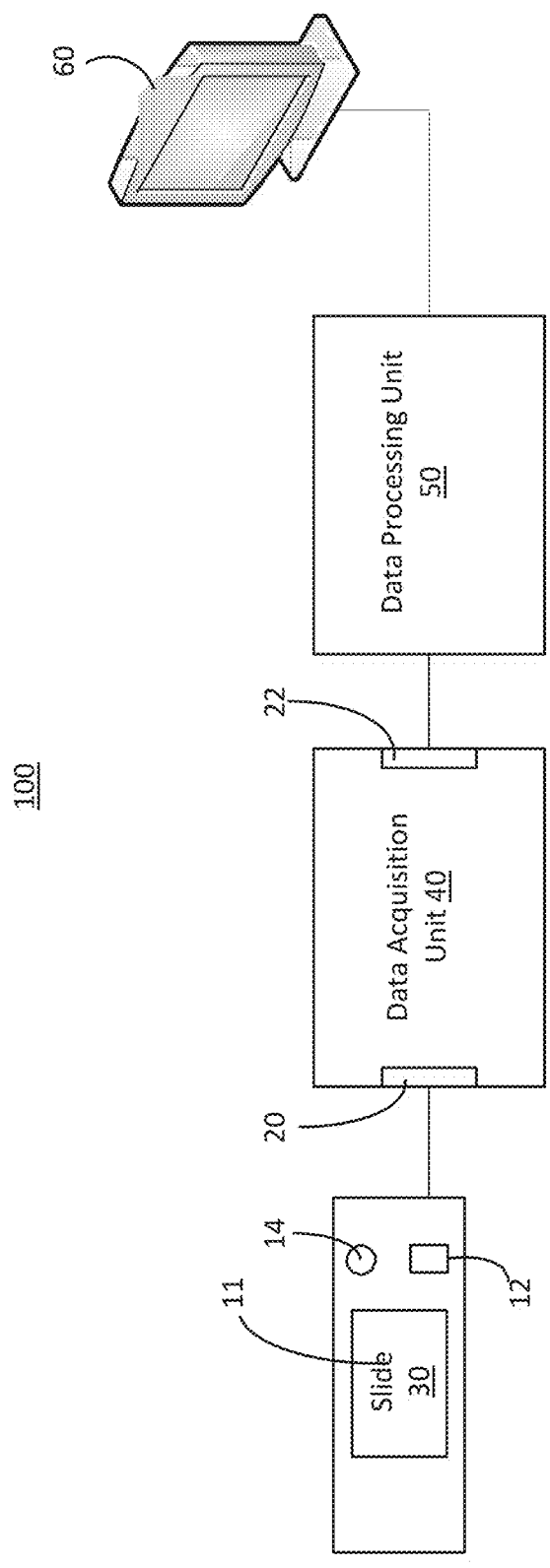
FIG. 14: is a block diagram of a system for bubble detection, according to an example embodiment of the present invention.

FIG. 14 shows an example system 100 for detecting bubbles according to an example embodiment of the present invention. In the example shown in FIG. 14, the system 100 includes a slide 30 that includes an area 10 in which a test solution containing a substance-of-interest is placed for analysis, a control unit 12 and a power source 14. The slide 30 can be formed of any electrically insulating material. For example, glass would typically be used for this purpose and to serve as a substrate, on top of which the area 10, control unit 12 and power source 14 are formed. The glass can be formed, for example, of silicon dioxide ($SiO_2$), possibly with additives. Alternatively, other types of silicate glasses may be used.

The area 10 includes an array of electrodes used for bubble detection. In an example embodiment, at least some of the electrodes in the area 10 are used for adjusting (also referred to herein as modulating) a pH level of the test solution. These pH modulating electrodes can be dedicated exclusively to adjusting the pH level or, alternatively, switched between pH modulating and bubble detecting modes of operation, as will subsequently be explained. (For example, U.S. patent application Ser. No. 13/543,300, mentioned earlier, describes the use of electrodes for pH modulation in a biosensor, which modulation can be performed using the electrodes discussed herein.)

Figure 15:
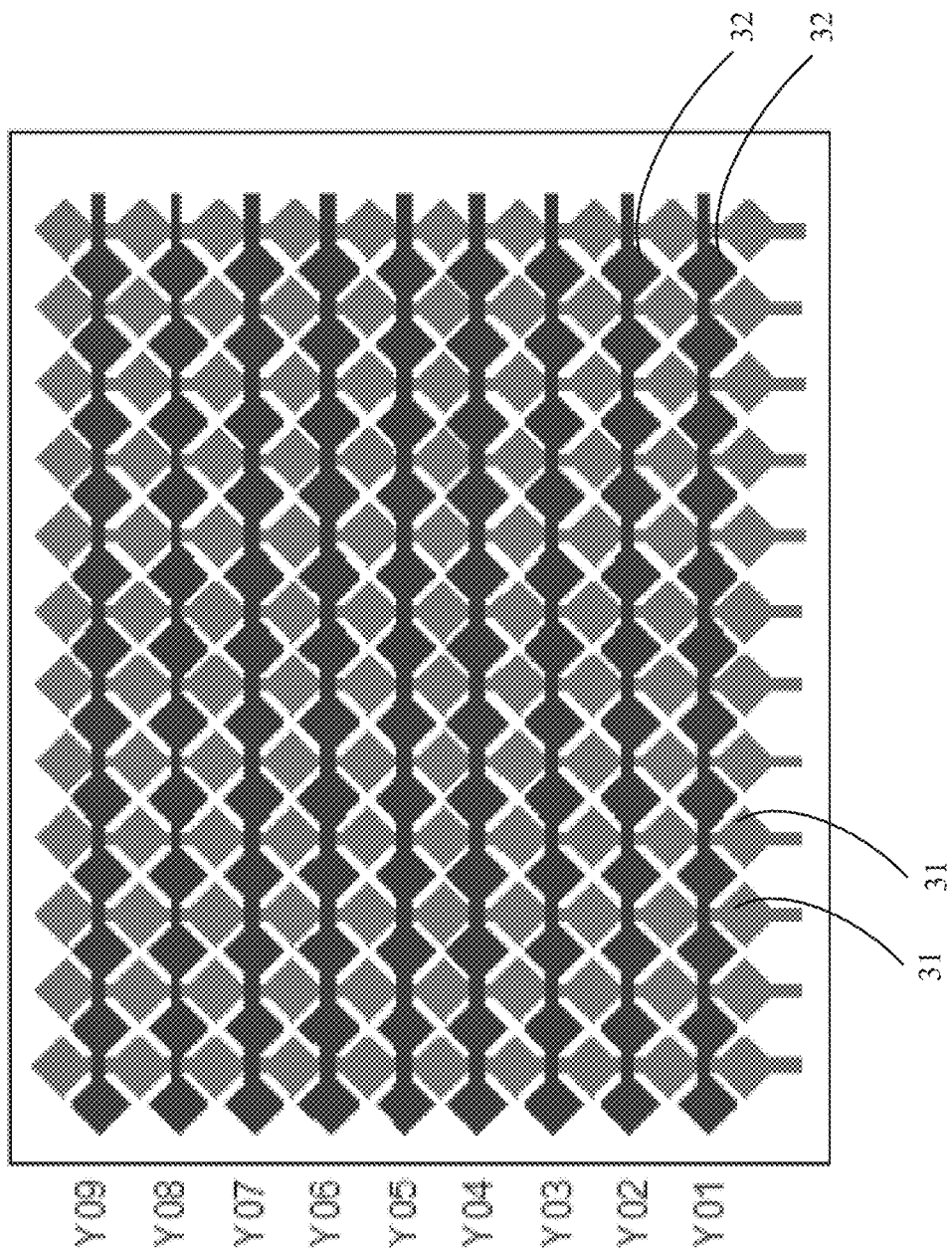
FIG. 15: is a top view of an example electrode array, according to an example embodiment of the present invention.
Figure 17:
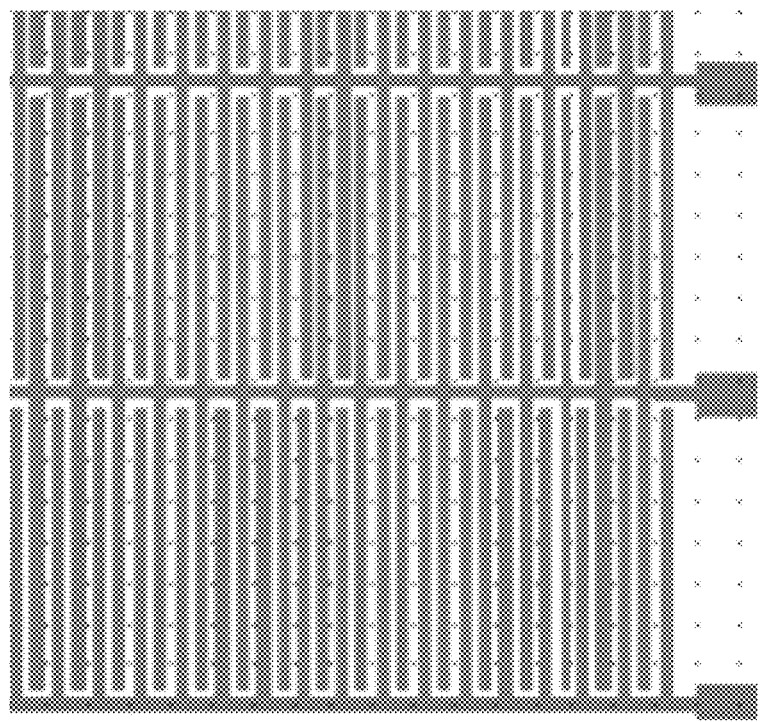
FIG. 16 and FIG. 17: show different electrode shapes, according to example embodiments of the present invention.
Figure 16:
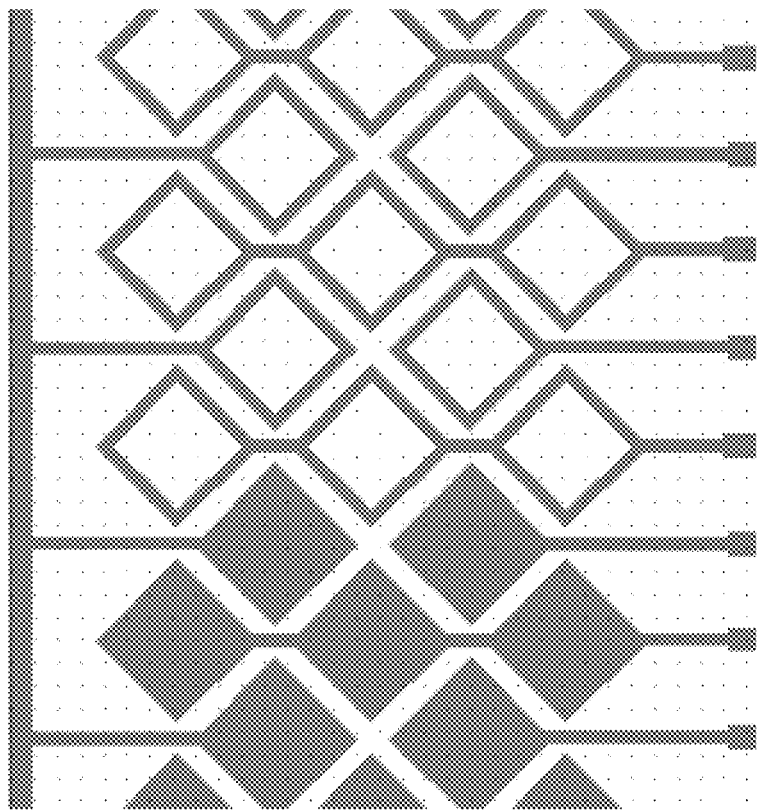

FIG. 15 shows a top view of an example electrode array, in which a set of column electrodes X01 to X12 are arranged at regularly spaced distances from each other. A set of row electrodes Y01 to Y09 are also arranged at regularly spaced distances and are separated from the column electrodes X01 to X12, e.g., by an intervening layer of glass. Each electrode includes one or more contact pads 31, 32 for use in bubble detection and/or pH modulation. The shape of the pads is variable and, in an example embodiment, is substantially square. FIG. 16 shows a close-up view of example square-shaped pads. FIG. 17 shows an alternative embodiment in which the pads form an interdigitated structure, and are therefore frame-shaped.

In the example illustrated in FIG. 14, the control unit 12 is electrically connected to the electrode array 10 and controls the array 10 to perform bubble detection and pH modulation. The control unit 12 can be, for example, a microprocessor or an application specific integrated circuit (ASIC). In an example embodiment, the control unit 12 is located on an electronic circuit board that is detachably connected to the slide 30, e.g., using pogo pins. The control unit 12 can be located within a packaged chip bonded directly to a rigid glass substrate, e.g., using a chip-on-glass process. In an alternative example embodiment, the slide 30 is formed of a flexible foil-type substrate and the control unit 12 is glued to the slide 30 using a z-axis adhesive to form a chip-on-foil, in a manner similar to how chips are bonded in certain liquid crystal displays. The control unit 12 can include, for example, a non-transitory computer readable storage medium containing program code that implements the example bubble detection and pH modulation techniques described herein. In addition to bubble detection, the control unit 12 can control the electrodes to perform other types of sensing or to control other sensing structures, as is known in the art of biosensors.

In an example embodiment, the control unit 12 transmits control signals that cause input pulses to be applied at specified electrodes. Capacitance values can be measured at the control unit 12 based on the responses of the electrodes to the input pulses. The measurement of capacitance is known in the art of touch screen displays, which utilize measurements of self-capacitance (e.g., a single electrode) or mutual capacitance (e.g., between two electrodes). To support bubble detection, the control unit 12 has a capacitance detection range that is greater than that of typical control units that measure capacitance in life science experiments. Control signals can also be used to apply input pulses for pH modulation. Control signals for pH modulation can be initiated by the control unit 12, e.g., in accordance with a predefined program sequence designed for pH modulation. Alternatively, the control signals for pH modulation is initiated externally, e.g., in response to a command from a data processing unit 50. In an example, the control unit 12 includes hardware and/or software components that perform preliminary signal processing on the measured capacitance values, including converting the measurements from analog to digital format and/or filtering the measurements. In an example, the processed measurements are then output as raw data to the data acquisition unit 40.

The power source 14 provides power to the control unit 12 and to the electrode array 10. For example, in an example embodiment, the power source 14 is a battery such as a coin-cell or a printed battery. In one example embodiment, the slide 30 is designed for one-time use and is disposable, the battery therefore being provided with a small energy capacity, e.g., sufficient for a single measurement, and the battery can be permanently attached to the slide, e.g., bonded or glued to the glass surface. In an example embodiment where the slide 30 is reusable, the battery can be rechargeable or user replaceable. Other forms of electric power delivery may alternatively be used. In one example embodiment, electrical power is delivered wirelessly through magnetic coupling between an external power supply (e.g., the data acquisition unit 40) and one or more resonant coils in the slide. As an alternative to magnetic coupling, but also using wireless power transfer, the external power supply may couple to the resonant coil using radiofrequency (RF) signals. In yet another example embodiment, the slide 30 receives power through a wired connection to the data acquisition unit 40.

In an example, the data acquisition unit 40 is a device that communicates with the slide 30 to receive the measured capacitance values from the control unit 12, in the form of raw data. For example, in an example, the data acquisition unit 40 includes a wired communication interface 20 to a corresponding interface in the slide 30. In one example embodiment, the raw data is output from the control unit 12 in parallel. For example, in an example embodiment, the control unit 12 includes a plurality of output channels, with data from a single row or a single column being output on a corresponding channel. In this embodiment, the interface 20, for example, converts the parallel data into a format suitable for transmission to the data processing unit 50. The conversion may involve parallel-to-serial conversion using a Universal Asynchronous Receiver/Transmitter (UART) or other conventional data conversion apparatus. In an alternative embodiment, the interface 20 communicates wirelessly with the slide 30, e.g., using RF signals.

In an example embodiment, the data processing unit 50 receives the raw data from an output interface 22 of the data acquisition unit 40, e.g., from a transmitter portion of the UART. The output interface 22 can be a wired, serial interface such as a Universal Serial Bus (USB) interface. Alternatively, the output interface 22 can be wireless, e.g., a Bluetooth or WiFi interface. In an example, the interface is a Bluetooth low energy (LE) interface. The data processing unit 50 can be, for example, a general purpose computer in the form of a desktop, a laptop or tablet, and includes, for example, a processor and a memory storing instructions for further processing of the raw data. For example, in an example embodiment, the further processing includes normalizing the raw data to a predefined scale and using the normalized data to generate output images, such as two or three-dimensional graphs, for display at the display device 60. Where the data processing unit 50 is a laptop or tablet, the display device 60 can be integrated into a housing of the data processing unit 50 as a single unit. The display device 60 may alternatively be externally connected, e.g., where the data processing unit 50 is a desktop. The output images may be combined to form a video that shows changes in the data over time. In one embodiment, the output images, which represent the measured capacitance values, are displayed together with additional output images corresponding to other measured data. For example, the output images and the additional output images may be displayed in different portions of the same display screen or overlaid (superimposed) on the same portion of the display screen.

In an example embodiment, the data processing unit 50 is also configured to issue commands to the control unit 12 for pH modulation. The commands may be automatically generated, e.g., when a processor of the data processing unit 50 determines that the pH level of the test solution should be adjusted. Alternatively or additionally, the commands may be user-initiated.

According to an example embodiment, the slide 30 may include a layered structure in which one or more electrode layers are located on top of a glass substrate. The layered structure can be formed, for example, using a lamination technique in which two or more layers are formed separately and then laminated together, e.g., using adhesive or bonding. Alternatively, the layered structure can be monolithically formed as a single unit, using techniques known in the art of semiconductor device fabrication. The layered structure may include one or more passivating layers formed, e.g., of $SiO_2$ (also referred to as oxide). However, it will be understood that the composition and size of passivating layers can vary, e.g., from an atomic layer of $SiO_2$ to several micrometers of $SiO_2$, and formed using various techniques such as low pressure chemical vapor deposition (LPCVD) or plasma-enhanced chemical vapor deposition (PECVD). Silicon nitride ($Si_3N_4$) is another example passivating material. Where the layered structure is formed using lamination, the passivating layer can be formed as a thin film that is laminated.

Figure 18:
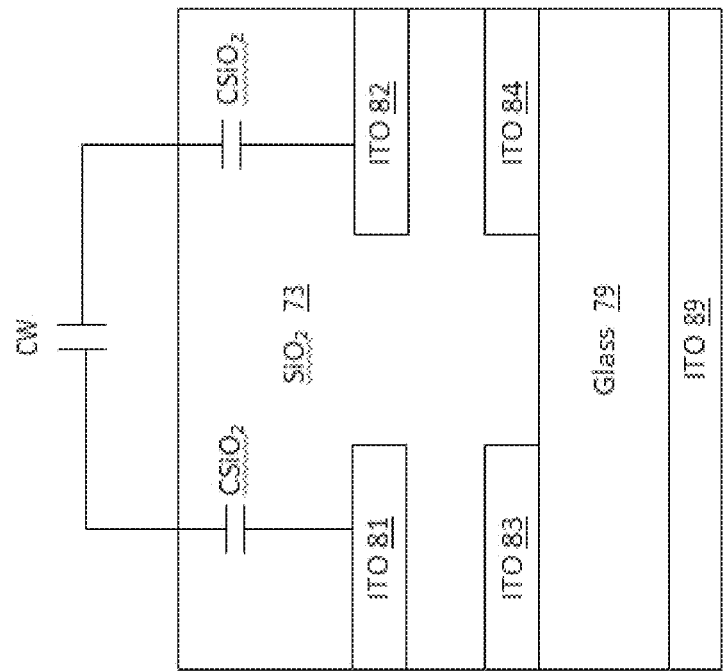

The capacitance based bubble detection principles used in the example embodiments of the present invention will now be described with reference to FIG. 18 to FIG. 23. FIG. 18 shows a simplified electrical model of a slide including electrodes (ITOs 81 to 84) in an $SiO_2$ layer 73. The ITOs 81 and 82 represent electrode pads in a first layer, e.g., row electrode pads. The ITOs 83 and 84 represent electrode pads in a second layer beneath the first layer, e.g., column electrode pads. The ITOs 81 to 84 are formed above a glass substrate 79, with an optional ITO layer 89 that serves as a bottommost, passivating layer. For simplicity, the portion of the electrode array used for pH modulation in certain example embodiments is not shown. In this simplified model, the capacitance of the test solution is assumed to be equivalent to the capacitance of water (CW) since the test solution is, in practice, mostly water. When there is no bubble over the electrodes, the solution is in contact with the $SiO_2$ layer 73 and contributes to a series capacitance between ITOs 81 and 82. The $SiO_2$ layer 73 also contributes to the series capacitance, as represented by two capacitances $CSiO_2$.

The pH modulating portion of the electrode array has been omitted for the sake of simplicity. One way to perform pH modulation is to separate the pads of adjacent electrodes so as to form channels that collect the test solution. The channels allow the test solution to come into contact with the electrodes, so that the pH level of the solution can be adjusted by sending a current between the adjacent electrodes. According to an example embodiment, the electrodes may be formed of any suitable conductive material, but are preferably indium tin oxide (ITO) because ITO is transparent and relatively colorless, making it suitable for experiments that involve optical measurements. This allows the entire measurement area 10 to be transparent. An oxide layer may be used as a passivating layer to cover the electrodes, similar to how the $SiO_2$ layer 73 covers the electrodes in FIG. 18 and FIG. 19. In fact, the same oxide layer may be used over the electrodes in both the bubble detecting and the pH modulation portions of the electrode array. Where the pH modulation is implemented using channels, in an example embodiment, the oxide layer does not completely fill the channels, but instead a lateral portion of the electrodes is left exposed to allow for contact with the test solution.

Figure 19:
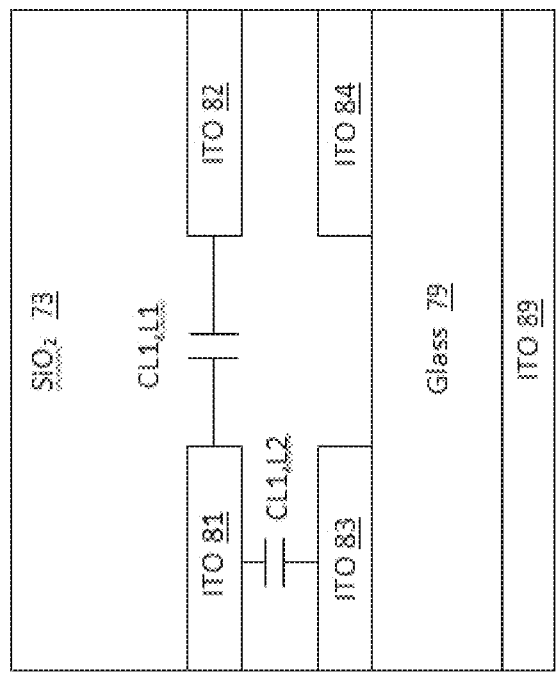
FIG. 18 and FIG. 19: show a simplified electrical model of a slide that provides bubble detection, according to an example embodiment of the present invention.

FIG. 19 shows additional details regarding the electrical model of FIG. 18 according to an example embodiment. In FIG. 19, the series capacitances are collectively represented as a mutual capacitance CL1,L1 between ITOs 81 and 82. Additionally, there exists a mutual capacitance between ITOs 81 and 83. In an example embodiment, bubbles are detected as a change in capacitance (e.g., in either of these mutual capacitances or in a self-capacitance) that results when the test solution is displaced by a bubble, which is typically formed of air. Since air has a much lower capacitance (the dielectric strength of air is approximately eighty times less than water), it is possible to detect a drop in capacitance associated with the presence of a bubble. This detection assumes that there is no electric field on top of the bubble which would minimally interfere with capacitance measurements. It also assumes that the size of the bubble is comparable to the pad, such that most of the surface of the pad is covered by the bubble, i.e., that no or almost no test solution is in contact with the pad. In practice, electromagnetic interference may create electric fields. Interference can be avoided through setup of an appropriate, low interference testing environment. As for bubble size, in practice the size will vary dramatically and it is unavoidable that sometimes a bubble will be smaller than the pad. To minimize the occurrence of bubbles that are smaller, each pad may be sized as small as possible while balancing performance parameters such as power consumption and maintaining inter-operative compatibility with the control unit 12. In one embodiment the pads are less than 2 millimeters wide, preferably 1 millimeter or less. This is substantially smaller than the size of electrodes typically used for conventional touch-screen applications or conventional bio-sensor applications.

Figure 20:
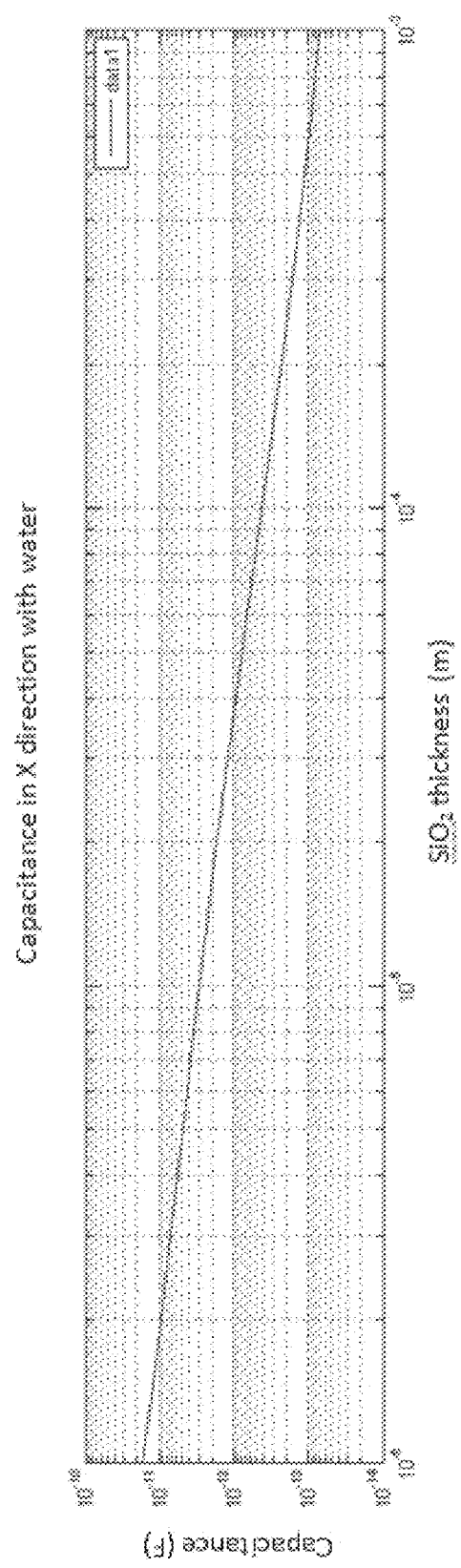
FIG. 20 to FIG. 22: are graphs showing simulated capacitance values with and without the presence of a bubble.

FIG. 20 is a simulated graph of self-capacitance along the x direction (from the top surface of the slide towards the glass substrate) when water covers a pad, in an example embodiment. The graph of FIG. 20 was generated based on a square pad of size 1 mm×1 mm. As shown, the capacitance decreases continuously from a value of approximately $2 \times 10^{-11}$ Farads at $10^{-6}$ meters down to approximately $7 \times 10^{-14}$ Farads at $10^{-3}$ meters.

Figure 21:
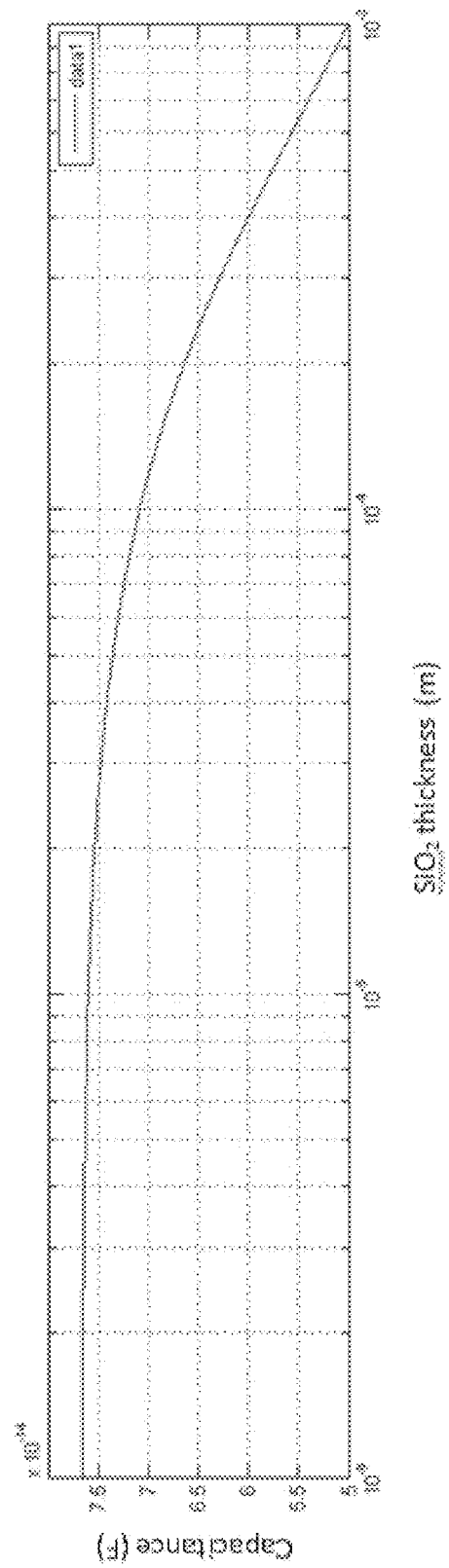

FIG. 21 is a simulated graph of self-capacitance along the x direction when a bubble having a diameter of 1 millimeter is present on a 1 mm×1 mm pad, in an example embodiment. As shown, the capacitance values are substantially smaller than the corresponding capacitance values from FIG. 20 between $10^{-6}$ and $10^{-3}$ meters. Specifically, the capacitance starts at approximately $7.6 \times 10^{-14}$ Farads and drops beginning around $3 \times 10^{-5}$ meters to approximately $5 \times 10^{-14}$ Farads. Therefore, the capacitance with water is several orders of magnitude greater for the majority of points between $10^{-6}$ and $10^{-3}$ meters. Accordingly, one way to detect bubbles, according to an example embodiment of the present invention, is based on an evaluation of the value or the magnitude of a capacitance at any given pad, e.g., by comparing the value or magnitude to a predefined threshold value. A bubble would then correspond to a capacitance that is less than the threshold. FIG. 20 and FIG. 21 are provided to illustrate basic electromagnetic principles by which example embodiments of the present invention detect bubbles based on changes in capacitance, and are not to be construed as restricting the range of capacitance detection techniques that may be applicable to a system or method of the present invention.

Figure 22:
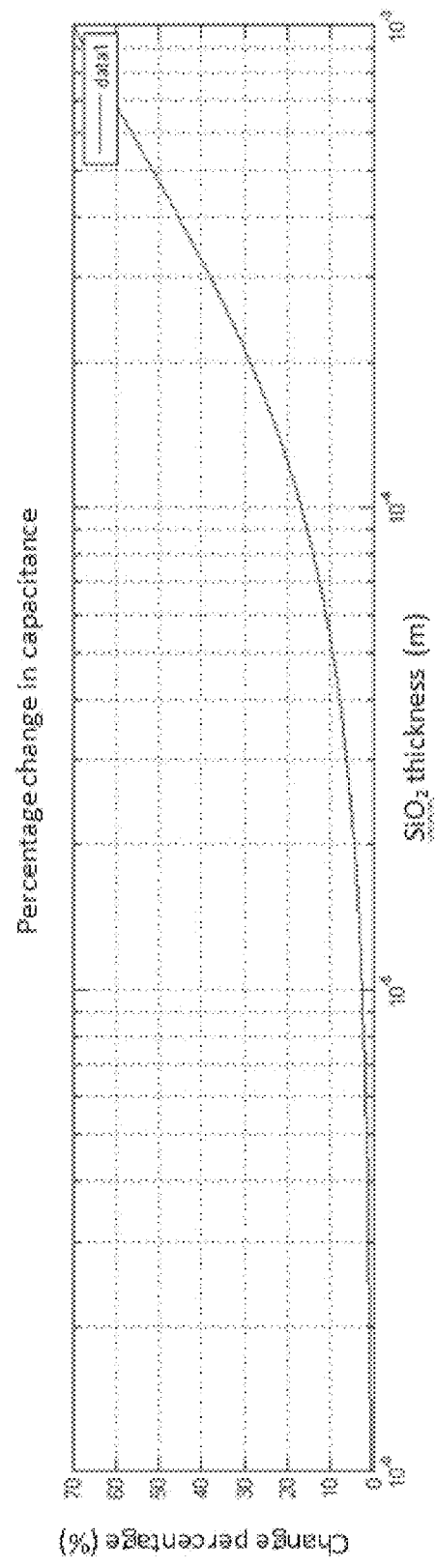

Another way to detect bubbles is based on the percentage change in capacitance from water to a bubble. The simulated graph in FIG. 22, whose values were calculated using the values from FIG. 20 and FIG. 21, shows this difference in an example embodiment. In FIG. 22, the percentage change is initially small, but starts to increase at around $10^{-5}$ meters. Therefore, detection may be based on the percentage change if the pads are suitably located, e.g., at a distance of $10^{-5}$ meters or more from the top surface of the slide.

In addition or as an alternative to evaluating the capacitance on an individual basis (e.g., for each pad when evaluating self-capacitance or for a pair of pads when evaluating mutual-capacitance), detection can be based on a comparison of capacitance values associated with a plurality of pads, according to an example embodiment. For example, according to an example embodiment, capacitance values from a group of neighboring pads are compared to determine whether any of the capacitance values is unusually small relative to the other capacitance values. This comparison is advantageous because it does not require the use of a threshold value, which may need to be adjusted based on the design of the slide, e.g., parameters such as pad size, shape or location.

Figure 23:
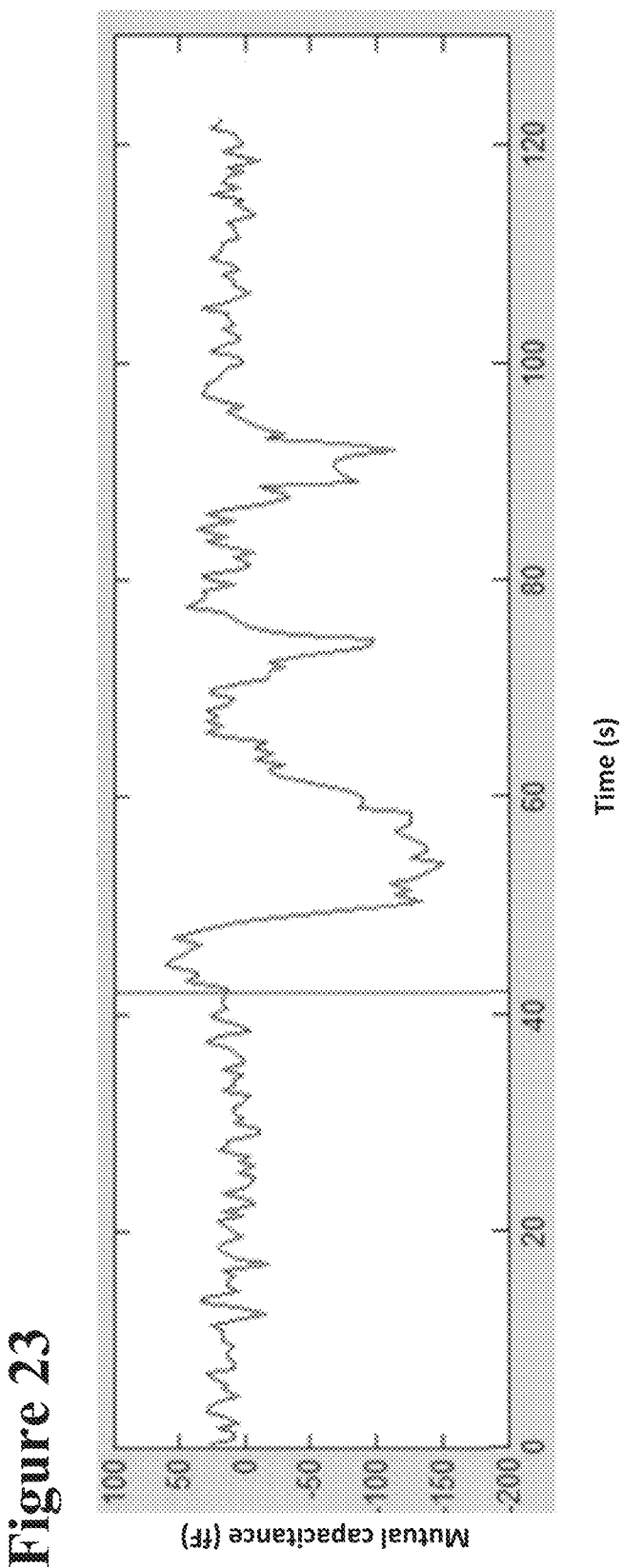
FIG. 23: is a graph showing actual measured capacitance values with and without the presence of a bubble.

FIG. 23 is a graph showing actual test results from a prototype slide of an example embodiment. The graph shows mutual capacitance values between a column electrode and a row electrode. A bubble was manually introduced at the intersection of these electrodes, beginning at around 50 seconds. The bubble was then removed and another bubble introduced at around 75 seconds. This process was repeated again, with another bubble at around 90 seconds. Each time a bubble was introduced, the capacitance dropped substantially.

Control units exist for acquiring capacitance measurements in connection with touch-screen applications. However, these control units are generally unsuitable for use with the bubble detection according to the example embodiments of the present invention. These conventional control units are unsuitable because they tend to have a narrower detection range and lower sensitivity than what is required for the example embodiments. In contrast, bubble detection according to the example embodiments requires the ability to capture large capacitance swings (e.g., a 400 pF change in going from water to bubble) in addition to a high resolution in order to capture the low capacitance values associated with bubbles. A typical capacitance value range for when a bubble exists could be between 20 fF to 40 μF. The large range is due to the fact that many choices are available as to the size of the electrodes and the thickness of the passivation layer on top of the electrodes (e.g., $SiO_2$, $TiO_2$, nitride, or no passivation layer at all).

Figure 24:
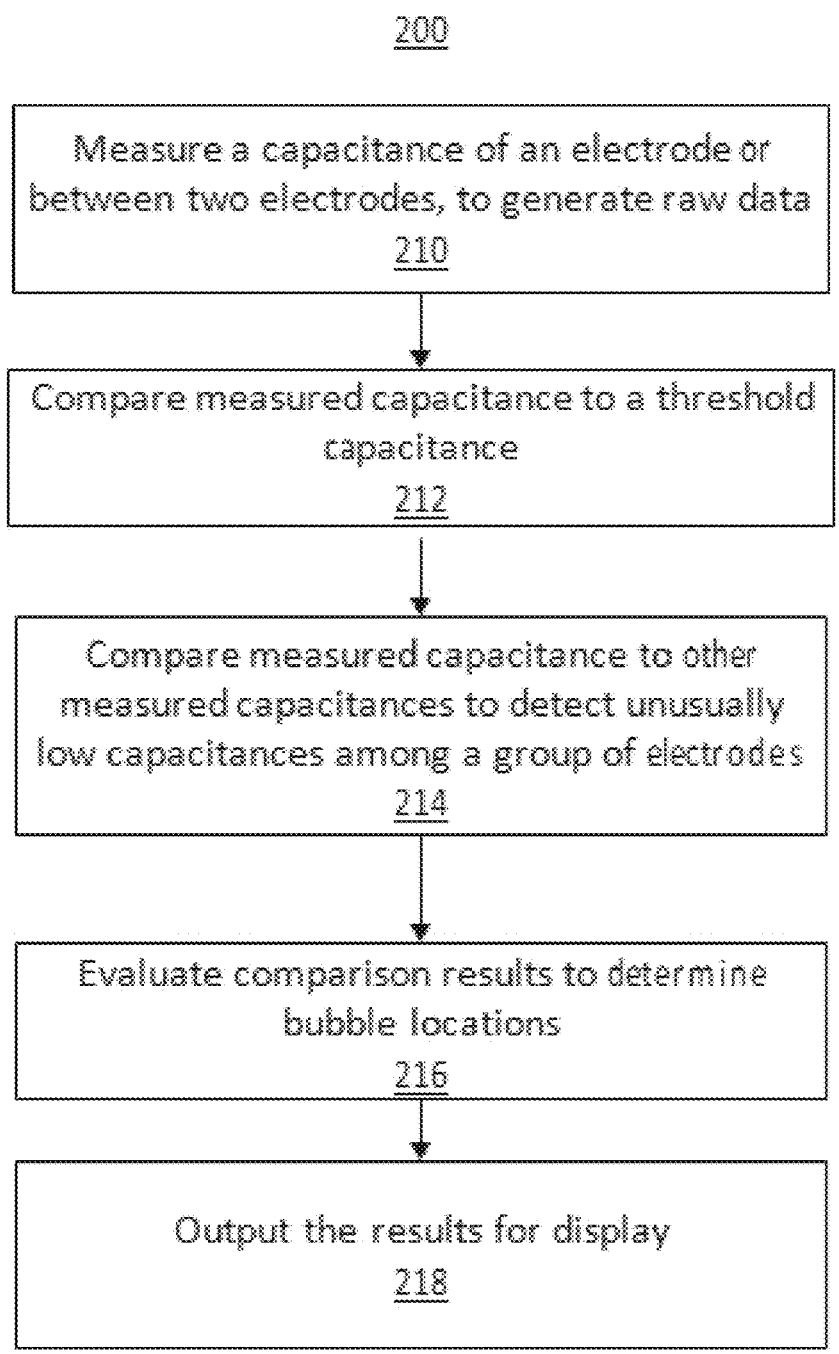
FIG. 24: is a flowchart of a method for detecting bubbles, according to an example embodiment of the present invention.

FIG. 24 is a flowchart of a method 200 for detecting bubbles according to an example embodiment of the present invention. According to an example embodiment, the method 200 is performed using the system 100.

At step 210, a capacitance (self or mutual) is measured at an electrode or between two electrodes to measure a capacitance value and the value is output as raw data. For example, in an example embodiment, the measurement is performed by outputting a control signal from the control unit 12, which control signal results in the application of an input pulse to an electrode being measured. The control unit 12 senses the electrical response of the electrode, e.g., by measuring a voltage or a current across the electrode, or between the electrode and another electrode, and calculates the capacitance as a function of this response. The calculation of self and mutual capacitances is known in the art of touch screen displays. Each measured capacitance can be output as a raw data value to the data processing unit 50 using the data acquisition unit 40.

Figure 25:
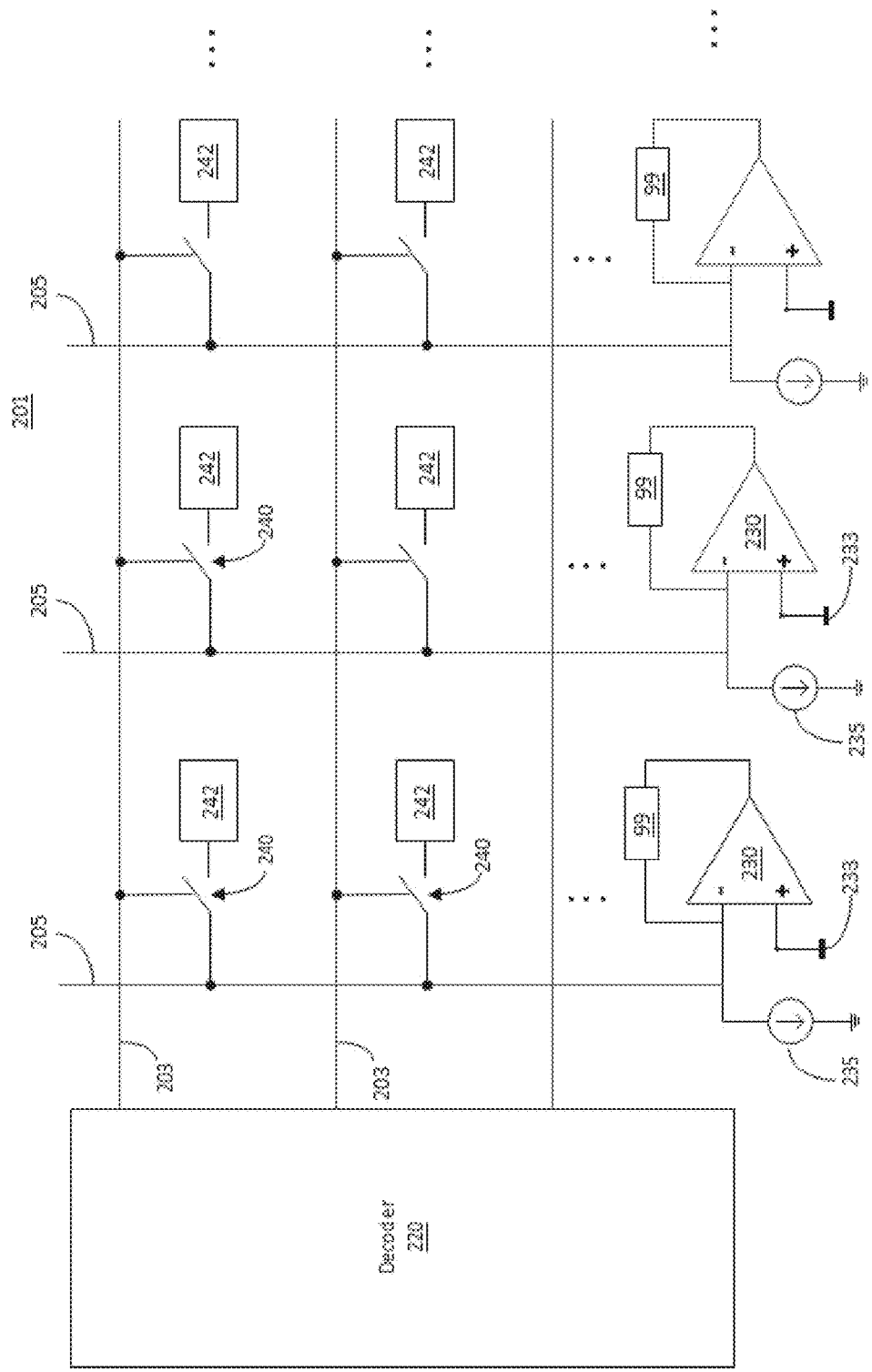
FIG. 25: is a simplified schematic of a circuit for calculating capacitance, according to an example embodiment of the present invention.

FIG. 25 is a simplified schematic of a circuit 201 for measuring capacitance according to an example embodiment of the present invention, and is provided in support of the method 200. The circuit 201 includes a decoder 220, which may be included in the control unit 12 of FIG. 14. The decoder 220 is connected via a plurality of driving lines 203, over which the decoder 220 sends signals to activate switches 240. The switches 240 may be implemented as thin-film transistors (TFTs) and are switched to connect to respective electrodes 242 that form the electrode array. The switches 240 are controlled by the decoder 220 to perform the capacitance measurements, e.g., by driving a specific line 203 simultaneously with an adjacent line 203. The switches 240 are further connected to sensing lines 205, which in this example, form the columns of the array. Each sensing line 205 is connected to a respective amplifier 230. The amplifiers 230 are in a negative feedback configuration with a sensing line 205 and a capacitor 99 being connected to a negative amplifier input, which is also connected to ground via a current source 235. A positive input of each amplifier 230 is connected to reference voltage 233, which may also be ground. The voltages on the sensing lines 205 are influenced by the capacitances at the electrodes, which capacitances depend on whether a bubble is present. Thus, the voltage outputs of the amplifiers 230 correspond to measured capacitances.

Returning to FIG. 24, at step 212, the measured capacitance is compared to a threshold value. As mentioned above, the threshold value may vary depending on factors such as pad size, shape or location. However, given the design specifications of the slide, and in view of the above discussion on the bubble detection principles, one of ordinary skill in the art would be able to compute a suitable threshold value.

Alternatively or additionally, at step 214 the measured capacitance is compared to other measured capacitances, e.g., from a group of neighboring electrodes or the entire set of electrodes in the array, to detect unusually low capacitances.

At step 216, the results of the comparisons are evaluated at the data processing unit 60 to determine, based on the bubble detection principles described earlier, whether any bubbles exist, and if so, where the bubbles are located.

At step 218, the results are output for display at the display device 60. According to an example embodiment, raw data values are displayed in the form of a two-dimensional table. Each table entry corresponds to a measured capacitance value obtained from a corresponding electrode pad. The raw data may be displayed as a three-dimensional graph, e.g., a 3-D mesh where the x and y values correspond to electrode locations and the z values correspond to measured capacitance values. To facilitate visual recognition, in an example embodiment, the graph is color coded, e.g., using a gradient scheme, e.g., a gray scale scheme or a heat map in which the color gradually changes until a bubble location is reached, at which point the color is changed to a color that contrasts the color(s) of non-bubble locations. In another embodiment, color coding is used to show bubble locations on a two-dimensional graph in which the capacitance values are represented using changes in color. Alternatively or additionally to the display of raw data, the data processing unit 60, according to an example embodiment, processes the raw data by normalizing it to a predefined scale. The above described graphs can be displayed alone or together with additional graphs from other parameters that are the subject of the experiment, e.g., pH value and flow rate. In one embodiment, the additional values are displayed on the same graph, e.g., using a different color scheme and superimposed onto the capacitance values.

Advantageously, the graphical display of the capacitance values allows a user to quickly determine where bubbles are located, and to take appropriate corrective action in response to the presence of bubbles. The user may decide, for example, to keep those additional values (corresponding to one or more parameters being measured by the experiment) which are not associated with the locations of detected bubbles, while discarding values associated with bubble locations. Alternatively, the user may decide that the entire set of data should be discarded because there are too many bubbles, thus making the additional values unreliable as a whole.

According to an example embodiment, the capacitance values are superimposed onto additional measurement data, which additional data is stored in association with layout data representing the physical configuration of the measurement area. The layout data may be stored in an electronic file in the form of an image (e.g., a scanned image of the measurement area) or text (e.g., a configuration file for a microarray spotter used to fabricate the array, or a GenePix Array List (GAL) file). The additional measurement data may also be image or text (e.g., measured pH values stored in a GAL file or measured pH values rendered in grayscale on a scanned image of the measurement area).

According to an example embodiment in which the capacitance values are superimposed, a composite display may be generated in step 218, which display shows a graphical representation of the array together with the capacitance values superimposed onto the additional measurement values at corresponding locations in the array. The superimposition can be rendered as text-on-text, text-on-image or image-on-image. An example of text-on-text is displaying a capacitance value in one half of an array location and additional measurement data in the other half. An example of text-on-image is displaying the capacitances using a heat map while representing the additional measurement data as numerical values on the heat map. An example of image-on-image is displaying the capacitances using a heat map while representing the additional measurement data using a 3-D mesh. Superimposed data may be stored in the electronic layout file, prior to or in conjunction with the superimposed display.

According to an example embodiment, a processor on the slide or on an external computer is configured to automatically invalidate the additional measurement data (e.g., by replacing measurement values with null values) in response to detecting bubbles. For example, the processor on the slide may detect bubble locations and output an indication of where the bubbles are located to the external computer, which then performs the invalidating based on the indicated locations. This spares the user from having to manually review the capacitance values to decide whether to keep the additional measurement data.

Figure 26:
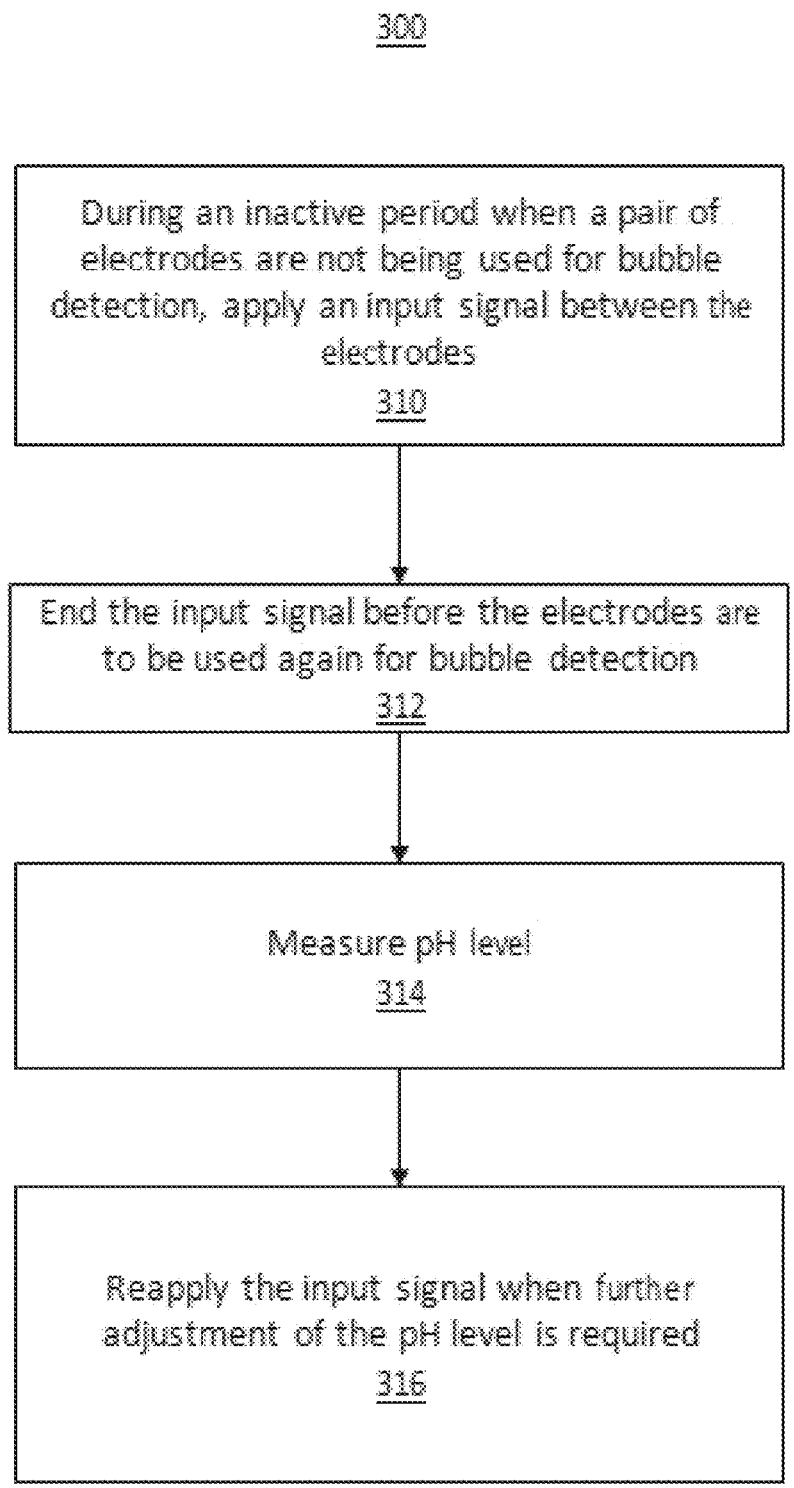
FIG. 26: is a flowchart of a method for pH modulation, according to an example embodiment of the present invention.

According to an example embodiment, bubble detection is combined with pH modulation. FIG. 26 is a flowchart of a method 300 for pH modulation according to an example embodiment of the present invention. According to an example embodiment, the method 300 is performed using the system 100.

At step 310, a pair of electrodes that are not currently being used for bubble detection are switched to a pH modulation mode of operation by applying an input signal, e.g., a pulsed current between the electrodes. Preferably, the switches that control the mode of operation of the electrodes are implemented using TFTs, e.g., formed using amorphous silicon, polysilicon or indium gallium zinc oxide (IgZo). An advantage to using thin-film transistors is that the total capacitance of each electrode and its corresponding circuitry is reduced, thereby increasing the speed of measurement in addition to circumventing the need for thick oxides on the electrodes.

To perform bubble detection, an input pulse can be applied, for example, to a single electrode. The input pulse for bubble detection may, but need not be identical in shape, magnitude or duration to the input pulse used for pH modulation. Changes in capacitance between water contact and bubble contact are detected by observing the electric response of the same electrode or in the case of mutual capacitance, the response of another electrode.

The input signal applied at step 310 for pH modulation may be applied during a time in which the input pulse for the bubble detection is not being applied. As mentioned above, the input pulse for pH modulation is applied between a pair of electrodes. This produces a current that, through oxidation and reduction of buffer components (e.g., quinones), changes the pH level of a test solution situated between the electrodes.

At step 312, the input signal is ended before the electrodes are to be used again for bubble detection.

At step 314, the pH level of the test solution is measured to determine whether additional adjustment is required. Where the slide is configured for pH level measurement, the pH level can be calculated at the control unit 12. Alternatively, the pH level can be measured using a separate testing device.

At step 316, the input signal is reapplied by the control unit 12 in response to determining that further adjustment of the pH level is required. In one embodiment, the control unit 12 is configured to apply the input signal multiple times, as a plurality of pH modulating pulses, before determining whether further adjustment is required. The plurality of pH modulating pulses can be applied to the same pair of electrodes or to a different electrode pair. Similarly, the input signal may be reapplied at step 316 to the same or a different pair of electrodes. For example, the pH modulating pulses may be applied to different electrode pairs in a sequential manner so that the entire electrode array is triggered over time to perform pH modulation.

According to an example embodiment, the electrodes can be used to perform functions in addition to bubble detection and pH modulation. For example, electrodes can be used for temperature modulation. As another example, the capacitance measurements can be used to estimate the dielectric constant of the test solution, which dielectric constant is then correlated to a rate of cell growth or a rate with which the substance-on-interest binds to a biomolecule.

Example embodiments were described in which the electrodes were arranged in two layers (FIG. 18 and FIG. 19). However, it will be understood that the number of layers can be more or less. In fact, a single layer may be sufficient for both pH modulation and bubble detection. Additionally, not every electrode layer needs to be used for pH modulation or bubble detection. Instead, further electrode layers can be used for other purposes, in accordance with the usage of electrodes in conventional biosensors.

Figure 27:
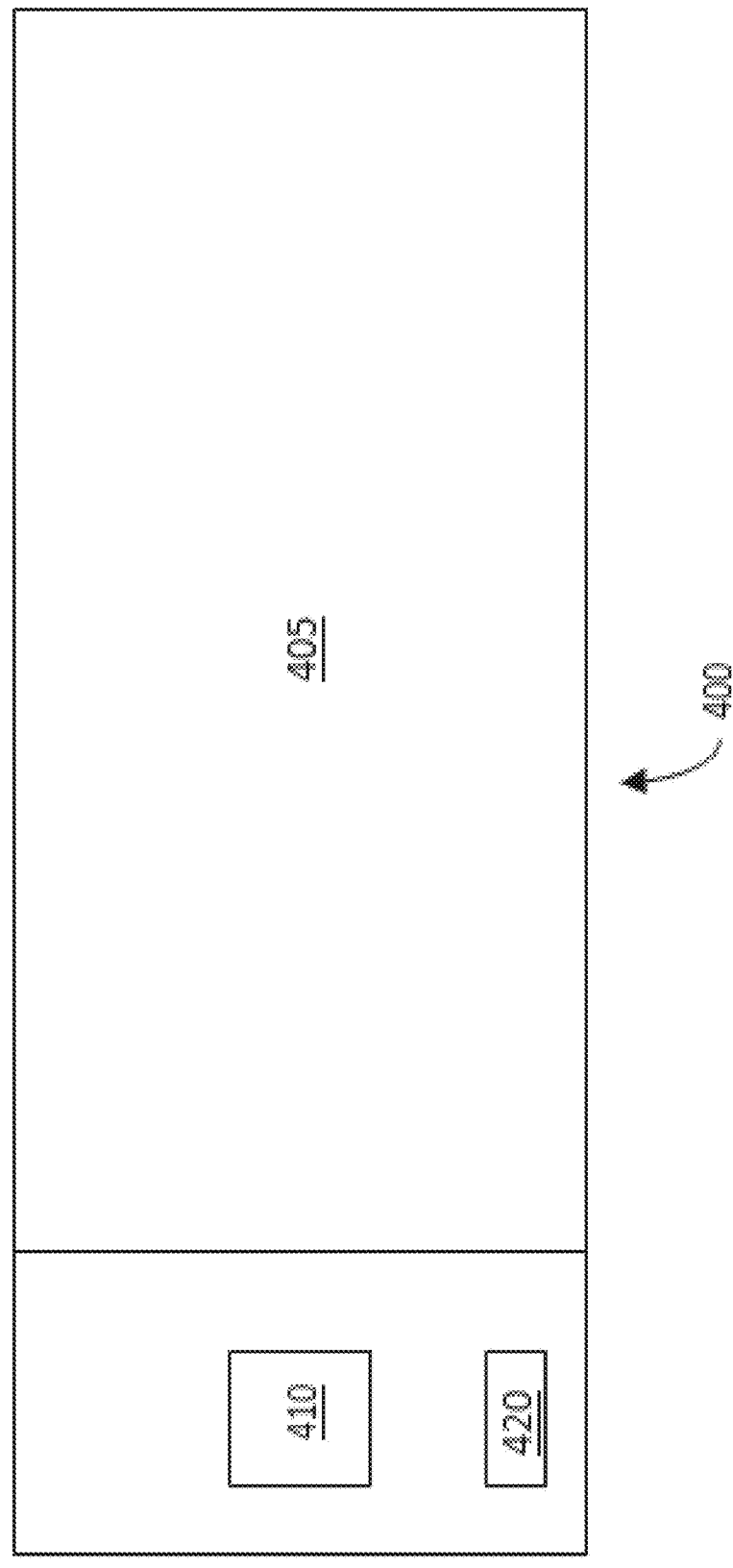
FIG. 27 to FIG. 29: each show a slide with data processing capability, according to an example embodiment of the present invention.
Figure 28:
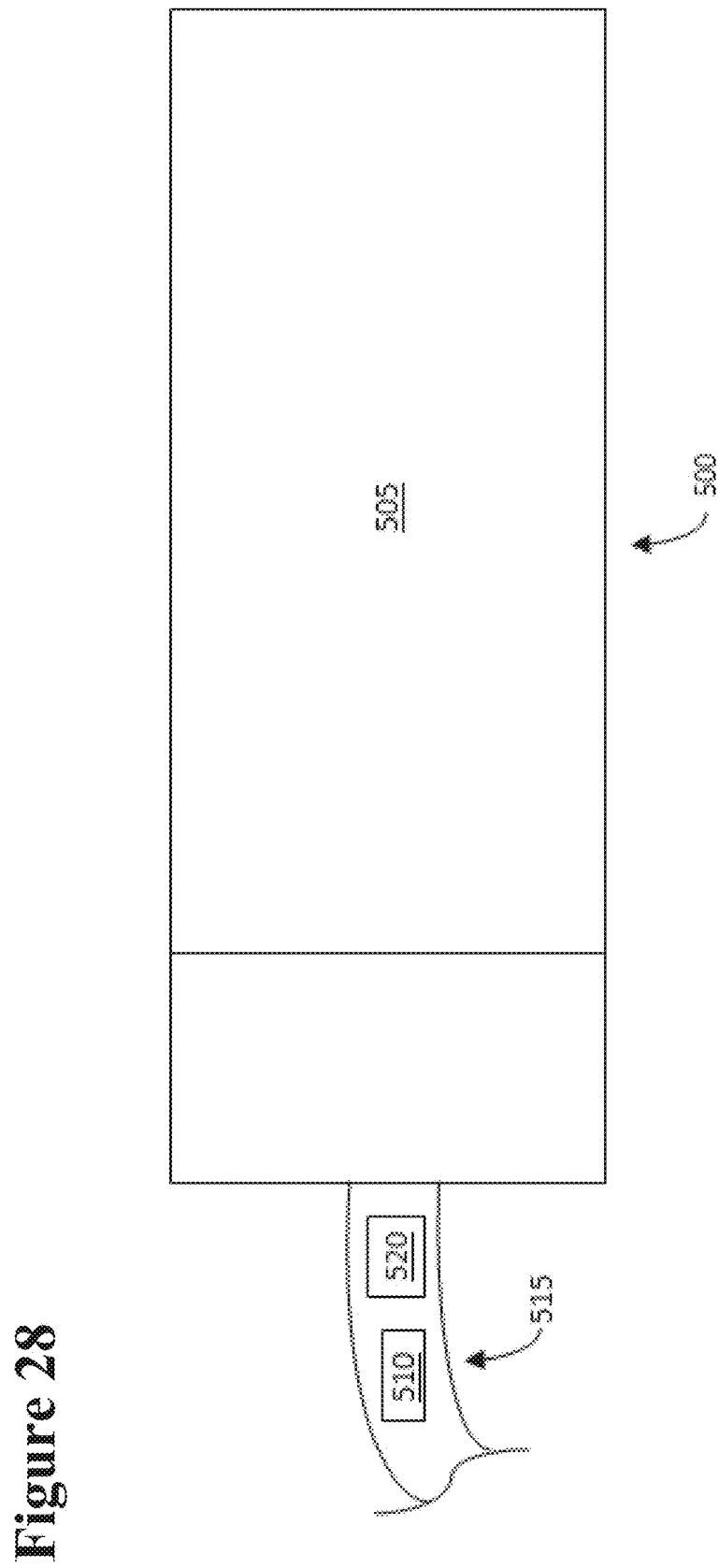
Figure 29:
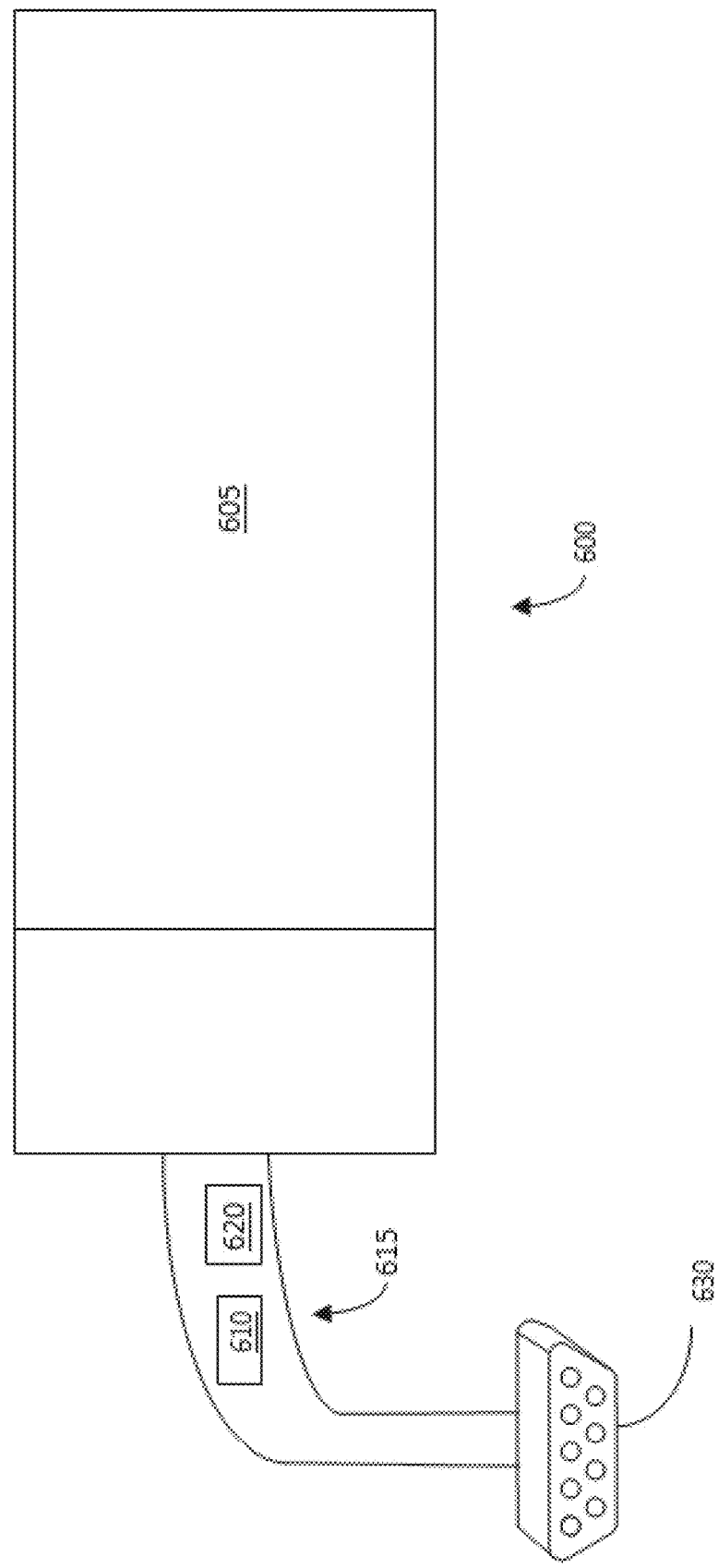

Example embodiments of the present invention relate to glass slides with at least some of the processing of measurement data being performed on the slide itself or on a peripheral device connected to a body of the slide, rather than at an external computer responsible for displaying the processed data. Such slides are referred to herein as an instrument-on-glass. FIG. 27 to FIG. 29 each show an example embodiment of an instrument-on-glass.

FIG. 27 shows a slide 400 according to an example embodiment of the present invention. The slide 400 includes a measurement area 405, a power source 410 and a processing circuit 420. The measurement area 405 may be formed of TFTs (for the switches) together with ITO (for the electrodes). Alternatively, the measurement area 405 may be formed using only ITO or ITO in combination with other metals. The power source 410 is analogous to the power source 14 in FIG. 14 and may be a battery or a passive power source powered, e.g., using magnetic or RF coupling.

The processing circuit 420 is analogous to the control unit 12 in FIG. 14 and may perform preliminary signal processing. Additionally, the processing circuit 420 may perform some of the functions described earlier with respect to the data processing unit 50 (e.g., normalizing or scaling capacitance values or controlling pH modulation). The processing circuit 420 may include a processor (e.g., one or more CMOS chips) that processes the raw data obtained from measurement area 405. The processing circuit 420 may further include a memory storing instructions or data, used by the processor to process the raw data. The processing circuit 420 may be configured to arrange the raw data into a suitable format for output to an external computer, or to perform preliminary data analysis (e.g., bubble detection and invalidating data associated with bubbles). The processor may control the sensing operation of the measurement area 405 (e.g., driving and reading data out of the array), perform data compression, and perform wired or wireless transmission of the preliminarily processed data to an external computer. Post-processing and output of the data for display may be performed at the external computer.

FIG. 28 shows a slide 500 according to an example embodiment of the present invention. The components 505, 510 and 520 are analogous to and perform the same functions as the components 405, 410 and 420, respectively, in FIG. 27. However, instead of being located on the body of the slide 500, the power source 510 and the processing circuit 520 are externally connected, e.g., on a peripheral circuit board 515 that fits into a hardware interface of the slide 500.

FIG. 29 shows a slide 600 according to an example embodiment of the present invention. The components 605, 610 and 620 are analogous to and perform the same functions as the components 405, 410 and 420, respectively, in FIG. 27. In the embodiment of FIG. 29, the power source 610 and the processing circuit are externally connected, similar to FIG. 28. However, the circuit board 615 includes a serial port connector for transmission of data and power between the board 615 and the external computer. Specifically, the serial port may be used to transfer measurement data to the external computer, and to supply power for operating the measurement area 605 or for recharging the power source 610.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a non-transitory hardware computer-readable medium including any conventional memory device, to perform any of the methods described herein, alone or in combination, e.g., to output any one or more of the described graphical user interfaces. The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), flash memory, and magnetic tape.

An example embodiment of the present invention is directed to a non-transitory, hardware computer-readable medium, e.g., as described above, on which are stored instructions executable by a processor to perform any one or more of the methods described herein.

An example embodiment of the present invention is directed to a method, e.g., of a hardware component or machine, of transmitting instructions executable by a processor to perform any one or more of the methods described herein.

Example embodiments of the present invention are directed to one or more of the above-described methods, e.g., computer-implemented methods, alone or in combination.

Example embodiments of the present invention provide devices and methods for using electronics to control the pH of a solution close to an electrode and a device for implementing the methods in an integrated electronic system. Preferably the devices and methods of the present invention are able to control the pH of the solution surrounding the electrode within a distance of about 1 cm.

According to an example embodiment, a method for changing the pH of a solution by electronic control includes providing an amount of electric input to the solution using two or more electrodes to electrochemically generate and/or consume hydrogen ions in the solution. The generation and/or consumption of the hydrogen ions are achieved by an electrochemical reaction of one or more redox active species in the solution. Preferably, the one or more redox active species is selected from the following: quinones, catechols, aminophenols hydrazines, and derivatives thereof. More preferably, the one or more redox active species is a quinone (See Thomas Finley, "Quinones," Kirk-Othmer Encyclopedia of Chemical Technology, 1-35 (2005)). Even more preferably, the one or more redox active species is selected from the following: hydroquinone, benzoquinone, naphthoquinonenaphthoquinone. Most preferably, the one or more redox active species is a quinone derivative, further defined below.

Preferably, the two or more electrodes comprise a sense electrode and a reference electrode (RE). In certain example embodiments of the present invention, the sense electrode also functions as a working electrode. In certain example embodiments of the present invention, the two or more electrodes include a counter electrode and/or a working electrode. In certain example embodiments of the present invention, the two or more electrodes are each independently made of metal oxide, gold, glassy carbon, graphene, silver, platinum, silver chloride, normal hydrogen, mercury drop, or saturated calomel. In certain example embodiments of the present invention, the solution is buffered, unbuffered, aqueous, organic, or a mixture thereof. In certain example embodiments of the present invention, the amount of electric input is provided by providing an amount of electric current. In certain example embodiments of the present invention, an electric source waveform is selected based on the amount of electric input to be provided. Preferably, the electric source waveform is a galvanostatic waveform or a potentiostatic waveform. More preferably, the electric source waveform is selected from a predetermined map that maps electric input amounts to respective solution pH values.

According to an example embodiment of the present invention, a method for controlling the pH of a solution using two or more electrodes includes obtaining the open circuit potential (OCP) of two or more electrodes in the solution while no electric input is being applied between the two or more electrodes, selecting an amount of electric input based on the OCP, and providing the amount of electric input to the solution between the two or more electrodes to change the pH of the solution. In certain example embodiments of the present invention, the OCP is obtained by measuring the OCP of the two or more electrodes in the solution or calculated from a known or measured initial pH. In certain example embodiments of the present invention, the method also includes determining the pH of the solution based on the OCP of the two or more electrodes in solution. In certain example embodiments of the present invention, the method also includes selecting an electric source waveform based on the amount of electric input and the amount of electric input is provided according to the selected electric source waveform.

In certain example embodiments of the present invention, the method further includes determining the pH of the solution based on a measured OCP of the two or more electrodes in the solution. In certain example embodiments of the present invention, the amount of electric input is selected based on the determined pH.

According to an example embodiment of the present invention, a method for monitoring the pH of a solution using a sense electrode, a reference electrode, and a working electrode includes selecting a target open circuit potential (OCP), characterizing an OCP of the solution between the reference electrode and the sense electrode while no electric input is being applied to the working electrode, and iteratively performing the following steps: selecting an amount of electric input to be applied to the working electrode in order to minimize a difference between the OCP of the solution and the target OCP; and applying the amount of electric input to the working electrode to adjust the OCP of the solution.

In certain example embodiments of the present invention, the target OCP is a fixed value and in other example embodiments, the target OCP is a variable value. In certain example embodiments of the present invention, the target OCP is a range with an upper bound and a lower bound or is a single value. Preferably, the target OCP is selected based on a target pH. Preferably, the target pH is user defined. In certain example embodiments of the present invention, the sense electrode also functions as the working electrode. In certain example embodiments of the present invention, the sense electrode and the working electrode are distinct electrodes. Preferably, the distance between the sense electrode and the working electrode is 0 cm to 1 cm. The electric input may be provided as an electric current or as an electric potential. Preferably, the amount of electric input is provided by applying an electric potential to the working electrode. More preferably, the electric potential is provided according to an electric source waveform. The electric source waveform is a galvanostatic waveform or a potentiostatic waveform. Even more preferably, the electric source waveform is selected from a predetermined map that maps electric input amounts to respective solution pH values. Preferably, the sense electrode is coated with a pH sensitive coating and the OCP of the sense electrode and the pH sensitive coating is dominated by the $H^+$ ion concentration. In certain example embodiments of the present invention, the pH sensitive coating is an organic material. In other example embodiments of the present invention, the pH sensitive coating is an inorganic material. Preferably, the pH sensitive coating is made from a material that is selected from the group consisting of polyaniline, polypyrrole, and iridium oxide.

The example embodiments involve monitoring and/or characterizing electrochemical parameters and using a detected signal as a feedback control to generate a desired pH waveform for a specific length of time. All the described methods involve the use of a redox couple to release $H^+$ ions, lowering pH, upon oxidation, and to consume $H^+$ ions, increasing pH, upon reduction based on the formula:

$$RH_2 \rightleftharpoons R + 2H^+ + 2e^-$$

An example of a redox reaction is the reaction of quinone derivatives. There are many different derivatives of quinone, each with specific oxidative and reductive peaks and the redox reaction rate has been shown to be dependent on the pH of the solution. The electrochemical properties of the electrode, including the electron transfer coefficient and the open circuit potential (OCP) in relation to a reference electrode, are also important. The OCP has been previously demonstrated to be dependent on the pH of the solution.

According to an example embodiment of the present invention, a device for controlling the pH of a solution includes a controller, two or more electrodes, and a solution containing one or more redox active species. The device is configured to measure the OCP between the two or more electrodes in the solution to generate a measured OCP data and send the measured OCP data to the controller. The controller is configured to iteratively perform the following steps: select an amount of current or an electric source waveform based on a difference between the target OCP data and the measured OCP data, apply the selected amount of current to the solution by providing an electric current or an electric potential, according to the electric potential waveform, to one or more of the two or more electrodes, and send a request to the device for another measurement of the OCP.

Preferably, the one or more redox active species in the solution generates and/or consumes hydrogen ions through an electrochemical reaction induced by the electric current or the electric potential applied to the solution. Preferably, the one or more redox active species is selected from the following: quinone, catechol, aminophenol, hydrazine, and derivatives thereof. More preferably, the one or more redox active species is a quinone. (See, Thomas Finley, "Quinones," Kirk-Othmer Encyclopedia of Chemical Technology, 1-35 (2005)). Even more preferably, the quinone is selected from the following: hydroquinone, benzoquinone, naphthoquinone, and derivatives thereof. Most preferably the one or more redox active species is a quinone derivative. In certain example embodiments of the present invention, the solution is buffered, unbuffered aqueous, organic, or a mixture thereof. In certain example embodiments of the present invention, the electric source waveform is a galvanostatic waveform or a potentiostatic waveform. Preferably, the electric source waveform is selected from a predetermined map that maps electric inputs to respective solution pH values. In certain example embodiments of the present invention, the two or more electrodes are made of metal oxide, glassy carbon, graphene, gold, silver, or platinum. Preferably, the two or more electrodes include a reference electrode and a sense electrode. More preferably, the two or more electrodes further include a working electrode and/or a counter electrode. Each of the two of more electrodes is respectively made of metal oxide, gold, glassy carbon, graphene, silver, platinum, silver chloride, normal hydrogen, mercury drop, or saturated calomel. In certain example embodiments of the present invention, the sense electrode also functions as a working electrode. Preferably, the sense electrode is coated with a pH sensitive coating and the OCP of the sense electrode and the pH sensitive coating is dominated by the H+ ion concentration. In certain example embodiments of the present invention, the pH sensitive coating is an organic or an inorganic material. Preferably, the pH sensitive coating is made from a material that is selected the group consisting of polyaniline, polypyrrole, and iridium oxide.

Also provided are quinone derivatives that can be added to solutions and are suitable for electrochemical pH modulation in biological buffers, electrochemically active compositions comprising the quinone derivatives, methods of making the derivatives and/or compositions, and uses thereof.

According to example embodiments, the electrochemically active composition comprising a quinone derivative, where the reactivity between a nucleophile and the quinone derivative is reduced compared to a reactivity between the nucleophile and an unsubstituted quinone from which the quinone derivative is derived, and the composition is configured such that the pH of the composition is electrochemically modulated via the quinone derivative. More preferably, the reactivity between the nucleophile and the quinone derivative is reduced by at least 50% compared to the reactivity between the nucleophile and the unsubstituted quinone from which the quinone derivative is derived. Preferably, the quinone derivative is defined by a chemical formula selected from the group consisting of:

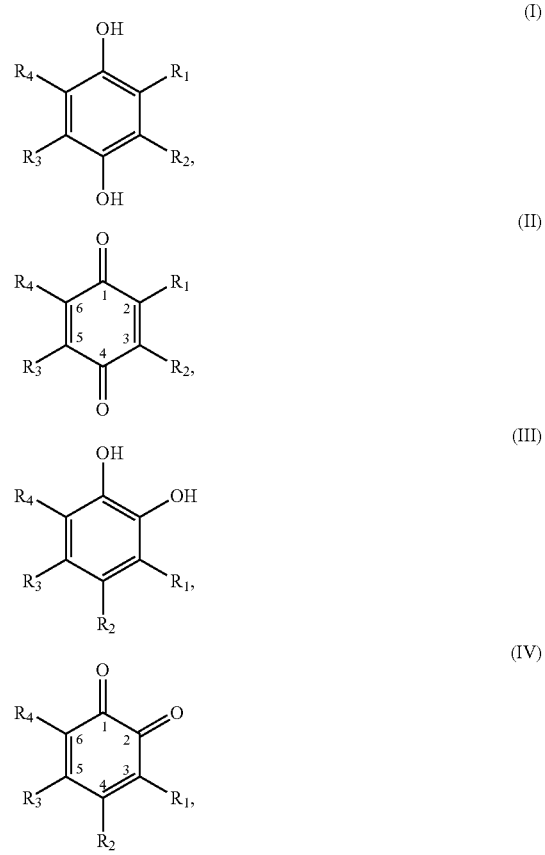

-continued

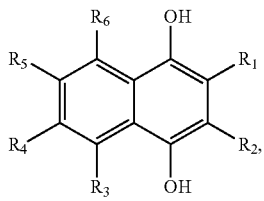
(V)

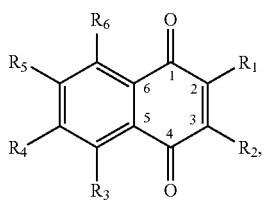
(VI)

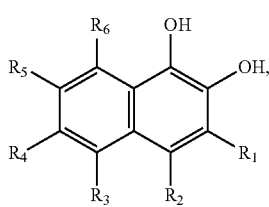
(VII)

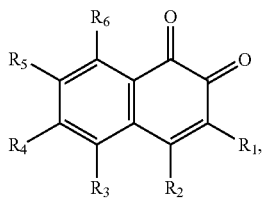
(VIII)

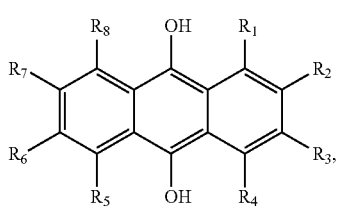
(IX)

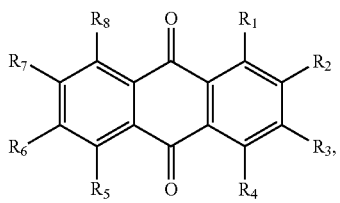
(X)

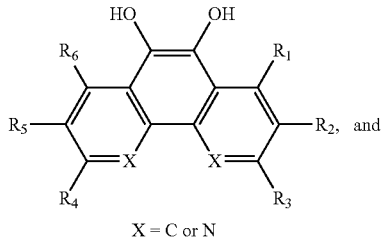
(XI)

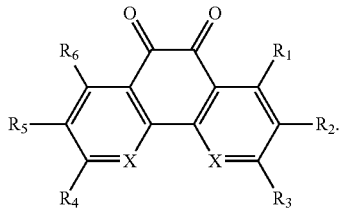
(XII)

X = C or N

In the above chemical formulas I to XII, each R group is independently selected from the group consisting of: H, $C_nH_{2n+1}$, Cl, F, I, Br, OM, $NO_2$, OH, $O_nCH_{2n}$, $O_nCH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids; at least one of the R groups is not hydrogen; M is any metal cation or $NH_4$; n is an integer from 1 to $10^9$; and y is an integer from 1 to $10^9$.

According to example embodiments, all of the R groups of the quinone derivative are different from each other. According to example embodiments, two or more of the R groups of the quinone derivative are the same. Preferably, the composition is an aqueous solution. According to example embodiments, the composition further comprises an additive selected from the group consisting of: an aqueous buffer, an organic solvent, an electrolyte, a buffer salt, a bioreagent, a biomolecule, a surfactant, a preservative, a cryoprotectant, and combinations thereof. Preferably the one or more nucleophiles are selected from the group consisting of: amines, thiols, amino acids, peptides, proteins, and combinations thereof. According to example embodiments, the reactivity between the nucleophile and the quinone derivative is reduced compared to the reactivity between the nucleophile and the unsubstituted quinone from which the quinone derivative is derived due to: (i) increased steric hindrance of a nucleophile binding site by one or more of the R groups; (ii) elimination of the nucleophile binding site by covalent bonding between the nucleophile binding site and one of the R groups. Preferably the reactivity between the nucleophile and the quinone derivative is reduced compared to the reactivity between the nucleophile and the unsubstituted quinone from which the quinone derivative is derived due both (i) and (ii).

Also provided are methods comprising modifying a quinone having one or more R groups by substituting one or more of the R groups with a substituent to provide a quinone derivative, where the quinone derivative has a reduced reactivity with a nucleophile compared to a reactivity between the quinone and the nucleophile; and the substituent is independently selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids; M is any metal cation or $NH_4$; n is an integer from 1 to $10^9$; and y is an integer from 1 to $10^9$. According to example embodiments, the one or more R groups are substituted with a polar. Preferably the polar group has atoms containing lone pair electrons. Preferably, the polar group is capable of forming hydrogen bonds with water. Preferably, the polar group contains at least one of oxygen, nitrogen, and sulfur atoms. More preferably, the polar group is selected from the group consisting of: OH, $CH_2OH$, $OCH_3$, COOH, $SO_3H$, $NH_2$, $NH_3Cl$, ONa, a sugar, an amino acid, and a peptide.

Also provided are methods of synthesizing substituted methyl quinone comprising: (i) a halide substitution step of reacting a starting material with a hydrogen halide in the presence of acetic acid and an aldehyde; (ii) reacting a material produced by step (i) with a nucleophile of structure R—X; (iii) reacting a material produced by step (ii) with an oxidizing agent; and (iv) reacting a material produced by step (iii) with a reducing agent, where R is selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids; M is any metal cation or $NH_4$; n is an integer from 1 to $10^9$; y is an integer from 1 to $10^9$; and X is either OH, $NH_2$, NHR, SH, $O^-$, or $S^-$.

According to example embodiments, the starting material is dialkoxybenzene and the result of the halide substitution step is an ortho-quinon, para-quinone, or a combination thereof. Preferably, the number of halide groups per molecule of the ortho-quinone or para-quinone is 1, 2, 3, or 4. According to example embodiments, the starting material is dialkoxynaphthalene and the result of the halide substitution step is an ortho-naphthoquinone, para-naphthoquinone, or a combination thereof. Preferably, the number of halide groups per molecule of the ortho-naphthoquinone or para-naphthoquinone is 1 or 2. Preferably, the hydrogen halide is selected from the group consisting of: HCl, HBr, HI, and combinations thereof. Preferably, the oxidizing agent is selected from the group consisting of: cerium ammonium nitrate, iodine, hydrogen peroxide, hypervalent iodine, iodobenzene diacetate, bromine compounds, and combinations thereof. Preferably, the reducing agent is selected from the group consisting of: sodium borohydrate, potassium borohydrate, sodium hydrosulfite, trichlorosilane, and combinations thereof.

Also provided are methods comprising: providing a biosensor comprising a support in an solution, the support comprising one or more electrodes and a biomolecule interface layer having one or more immobilized probes thereon, and the solution comprising a quinone derivative; adding a biomolecule analyte to the solution; electrochemically reacting the quinone derivative using the one or more electrodes to produce an amount of $H^+$ ions and/or an amount of OFF ions, wherein the pH of the solution close to the one or more electrodes is controlled by the amount of $H^+$ ions and/or the amount of OFF ions produced; collecting signals from the biosensor, where a reactivity between a nucleophile and the quinone derivative is reduced compared to a reactivity between the nucleophile and an unsubstituted quinone from which the quinone derivative is derived Preferably, the pH of the solution before electrochemically reacting the quinone derivative using the one or more electrodes is 1 to 14. Preferably, the pH of the solution after electrochemically reacting the quinone derivative using the one or more electrodes is 1 to 14. Preferably, the solution contains one or more nucleophiles. Preferably, the one or more nucleophiles are selected from the group consisting of: amines, thiols, amino acids, peptides, proteins, and combinations thereof. According to example embodiments, the solution contains a reduced quinone derivative and electrochemically reacting the quinone derivative results in an electrochemical oxidation reaction of the reduced quinone derivative to make the pH of the solution more acidic. Preferably, the concentration of the reduced quinone derivative is 0 to 1M. According to example embodiments, the solution contains an oxidized quinone derivative and electrochemically reacting the quinone derivative results in an electrochemical reduction reaction of the oxidized quinone derivative to make the pH of the solution more basic. Preferably, the concentration of the oxidized quinone derivative is 0 to 1M. Preferably, the solution contains one or more buffer components provided in a concentration that is 0 to 1M. Preferably, the one or more buffer components are selected from the group consisting of: organic solvents, electrolytes, bioreagents, biomolecules, surfactants, and combinations thereof. According to example embodiments, the method further comprises measuring the pH of the solution. Preferably, the pH is measured continuously. Preferably, the quinone derivative is electrochemically reacted by providing an amount of electric current. Preferably, the pH is measured before providing the amount of electric current. Preferably, the amount of electric current is selected based on the measured pH.

Quinones are herein defined as unsubstituted quinones. For example, the chemical structures I-XII would represent quinones if all of the R groups were hydrogen. Quinone derivatives are herein defined as compounds that are structurally similar to quinones except that at least one hydrogen is replaced by a substituent. In cases where more than one hydrogen is replaced by a substituent, the identity of the substituents may be independently selected but are not required to be unique. Compared to their unsubstituted counterparts the quinone derivatives of the present invention have reduced reactivity with nucleophiles and the pH of the biological buffer containing the quinone derivatives is able to be electrochemically modulated.

Also provided are methods for controlling a pH of a solution using two or more electrodes, the method comprising measuring an open circuit potential (OCP) of the two or more electrodes in the solution while no current is being applied between the two or more electrodes, selecting an amount of current based on the measured OCP, and providing the selected amount of current to the solution, thereby changing the pH of the solution by at least one electrochemically generating or consuming hydrogen ions. Preferably, generation and/or consumption of the hydrogen ions are achieved by an electrochemical reaction of one or more redox active species in the solution. Preferably, the one or more redox active species is selected from the group consisting of: quinones, catechols, aminophenols, hydrazines, derivatives thereof, and combinations thereof. Preferably, the one or more redox active species is a quinone selected from the following: hydroquinone, benzoquinone, naphthaquinone, derivatives thereof, and combinations thereof. Preferably, the two or more electrodes comprise a sense electrode and a reference electrode. According to example embodiments, the sense electrode is configured to also function as a working electrode. Preferably, the two or more electrodes also comprise a counter electrode and/or a working electrode. Preferably, the two or more electrodes are each independently made of a material selected from the group consisting of: metal oxide, gold, glassy carbon, graphene, silver, platinum, silver chloride, normal hydrogen, mercury drop, saturated calomel, and combinations thereof. Preferably, the solution is buffered, unbuffered, aqueous, organic, or a mixture thereof. Preferably, the method further comprises determining the pH of the solution based on the measured OCP of the two or more electrodes in the solution. Preferably, selection of an electrical waveform is based on the determined pH. Preferably, the method further comprises selecting an electrical waveform and providing the electrical waveform to the solution. The electrical waveform is either a galvanostatic waveform or a potentiostatic waveform. Preferably, the electrical waveform is selected from a predetermined map that maps respective current amounts to respective electrical waveforms.

Also provided is a biosensor system comprising a support that includes an a sense electrode, a reference electrode, and a working electrode; an electrochemically active agent, wherein the biosensor is configured to control a change of a redox state of the electrochemically active agent, and the biosensor is configured to iteratively perform the following: selecting an amount of current to be applied to the working electrode in order to minimize a difference between the OCP of the solution and the target OCP; applying the selected amount of current to the working electrode to adjust the OCP of the solution; and measuring the OCP of the solution. Preferably, the solution is an aqueous solution. According to example embodiments, the sense electrode also functions as the working electrode. According to example embodiments, the sense electrode and the working electrode are distinct electrodes and a distance between the sense electrode and the working electrode is 0 cm to 1 cm. Preferably, the amount of current applied to the working electrode is provided by applying an electrical waveform. The electrical waveform is a galvanostatic waveform or a potentiostatic waveform. Preferably, the electrical waveform is selected from a predetermined map that maps respective current amounts to respective electrical waveforms. Preferably, the sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and a combination thereof.

Also provided are methods for monitoring pH of a solution using a sense electrode, a reference electrode, and a working electrode, the method comprising selecting a target open circuit potential (OCP) based on a target pH for the solution; characterizing an OCP of the solution between the reference electrode and the sense electrode while no current is being applied to the working electrode; and iteratively performing the following: selecting an amount of current to be applied to the working electrode in order to minimize a difference between the OCP of the solution and the target OCP; applying the selected amount of current to the working electrode to adjust the OCP of the solution; and measuring the OCP of the solution. Preferably, the solution is an aqueous solution. Preferably, the target pH is set by incorporating an electro-chemical delta-sigma-modulator. More preferably, the output-signal of the electro-chemical delta-sigma-modulator is digitally filtered to get a digital representation of the charge needed to create the target pH. Preferably, the target OCP is a range with an upper bound and a lower bound. More preferably, the target pH is a single target value. According to example embodiments, the sense electrode also functions as the working electrode. According to example embodiments, the sense electrode and the working electrode are distinct electrodes and a distance between the sense electrode and the working electrode is 0 cm to 1 cm. Preferably, the amount of current applied to the working electrode is provided by applying an electrical waveform. The electrical waveform is a galvanostatic waveform or a potentiostatic waveform. Preferably, the electrical waveform is selected from a predetermined map that maps respective current amounts to respective electrical waveforms. Preferably, the sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and combinations thereof.

Also provided is a device for controlling a pH of a solution comprising: a controller; two or more electrodes; and a solution containing one or more redox active species, wherein the device is configured to iteratively perform the following: measure an open circuit potential (OCP) between the two or more electrodes in the solution to generate a measured OCP data; select, using the controller, an amount of current or an electric potential waveform based on a difference between target OCP data and the measured OCP data; and apply, using the controller, the selected amount of current or the selected electric potential waveform to the solution via one or more of the two or more electrodes. Preferably, the solution is an aqueous solution. Preferably, the one or more redox active species generates or consumes hydrogen ions through an electrochemical reaction induced by the electric current or the electric potential applied to the solution. Preferably, the one or more redox active species is selected from the following: quinones, catechols, aminophenols hydrazines, derivatives thereof, and combinations thereof. Preferably, the one or more redox active species is a quinone selected from the following: hydroquinone, benzoquinone, naphthaquinone, derivatives thereof, and combinations thereof. Preferably, the solution is buffered, unbuffered aqueous, organic, or a mixture thereof. Preferably, the electric potential waveform is a galvanostatic waveform or a potentiostatic waveform. More preferably, the electric potential waveform is selected from a predetermined map that maps respective current amounts to respective electric potential waveforms. Preferably, the two or more electrodes comprise two or more of a reference electrode, working electrode, counter electrode, or sense electrode that is made of a material independently selected from the group consisting of: metal oxide, gold, glassy carbon, graphene, silver, platinum, silver chloride, normal hydrogen, mercury drop, saturated calomel, and combinations thereof. According to example embodiments, the sense electrode also functions as a working electrode. Preferably, the sense electrode is coated with a pH sensitive coating. The pH sensitive coating is an organic material or an inorganic material. Preferably, the pH sensitive coating is made from a material selected from the group consisting of: polyaniline, polypyrrole, iridium oxide, and combinations thereof.

Figure 30:
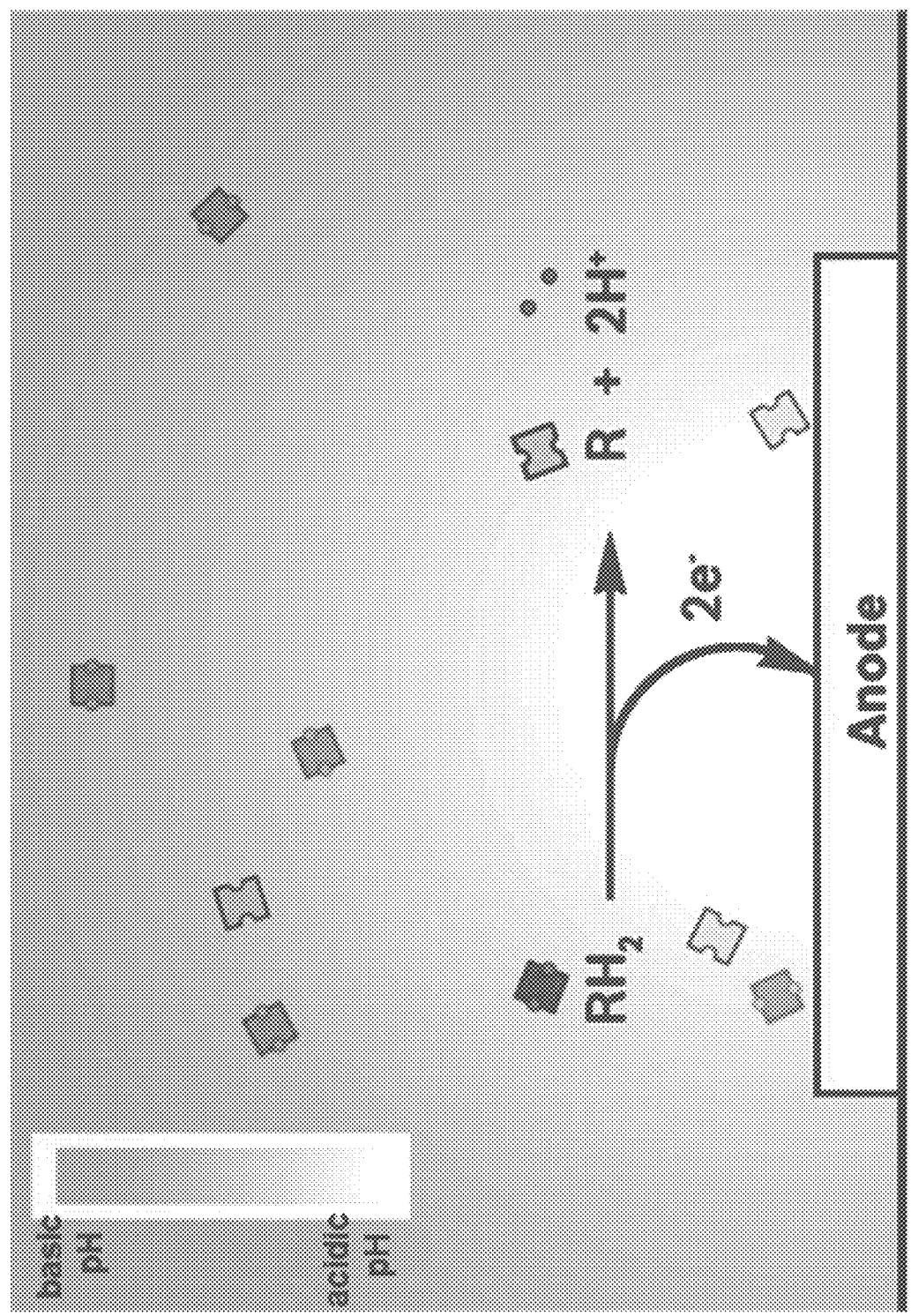
FIG. 30: shows a graphic representation of a system for electrochemical pH generation comprising a biological buffer with an electrochemically active agent dissolved in bulk solution over an electrode, where the change in pH is confined to the vicinity of the electrode surface through the buffering action of bulk solution, according to an example embodiment of the present invention.

A drawing of a system having electrochemically active agent in solution, according to an example embodiment of the present invention, is presented in FIG. 30. In previously described systems, the electrochemically active agent was attached to the electrode surface and not in solution. As shown in FIG. 30, the system provides an anode electrode and an electrochemically active agent in solution. Applying a current to the electrode induces the electrochemically active agent to undergo an electrochemical redox reaction which makes the pH of the solution near the electrode more acidic. Having the electrochemically active agent in solution rather than attached to the electrode surface has many advantages. For example, a more significant change can be inflicted on the surrounding environment if the amount of electrochemically active agent is not limited by the density of the surface layer, thereby increasing capacity of the device; fresh electrochemically active agent can be supplied to the electrode surface via diffusion from bulk solution, thereby allowing for cycling capability; and universal electrochemistry can be applied to all types of electrodes, which will not interfere with other surface chemistries such as attachment of anti-fouling reagents or biomolecules. Furthermore, in order to make use of quinones as electrochemically active agents for pH generation in biological solutions, the structure of the quinones were modified to satisfy the requirements for use in biological solutions. In order to be useful for pH modulation in biological buffers, a molecule should satisfy the following requirements: release or consume protons through electrochemical reaction upon electronic stimulation, sufficient water solubility, reduction and oxidation potential should be lower than the potential of water hydrolysis or other redox active species within the solution, stability in solution in the absence of electronic stimulation (i.e., no autooxidation/reduction), low reactivity towards nucleophiles, compatibility with biological samples (for example: proteins, peptides, cells, DNA, and enzymes).

Figure 31:
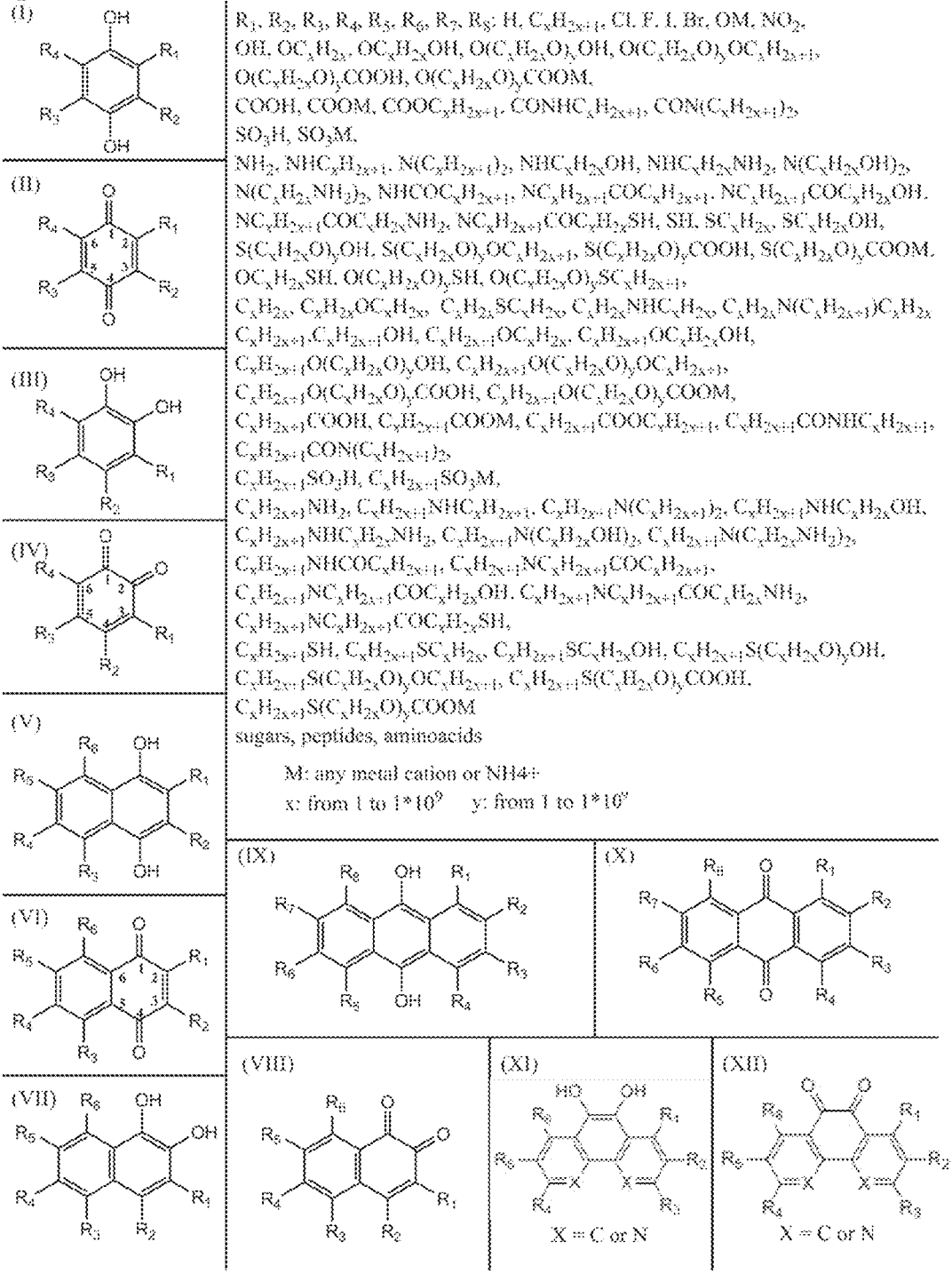
FIG. 31: provides structures of hydroquinones and benzoquinones that can be used for pH generation in biological solutions, according to an example embodiment of the present invention.

FIG. 31 shows quinone derivatives that can be used for pH modulation in aqueous solutions, according to example embodiments of the present invention.

The above description is intended to be illustrative, and not restrictive. Those skilled in the art can appreciate from the foregoing description that the present invention may be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and appendices. Further, steps illustrated in the flowcharts may be omitted and/or certain step sequences may be altered, and, in certain instances multiple illustrated steps may be simultaneously performed.

The following are examples which illustrate specific methods without the intention to be limiting in any manner. The examples may be modified within the scope of the description as would be understood from the prevailing knowledge.

Related applications International Patent App. No. PCT/EP2015/052661 and U.S. Pat. Provisional App. Ser. No. 61/939,396 are hereby incorporated by references in their entirety."

EXAMPLES

Example 1—Electrochemical Generation of H+ or OH− Ions at Electrode Surfaces

Electrode material used: The electrode material was indium tin oxide. This is a semiconducting electrode surface with very large potential window in an aqueous solution.

Electro-Oxidation of Species to Produce H$^+$ Ions.

Oxidation of ascorbic acid at the electrode surfaces produced H$^+$ ions and changed the electrode surface pH to a more acidic state:

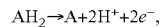

Figure 7A:
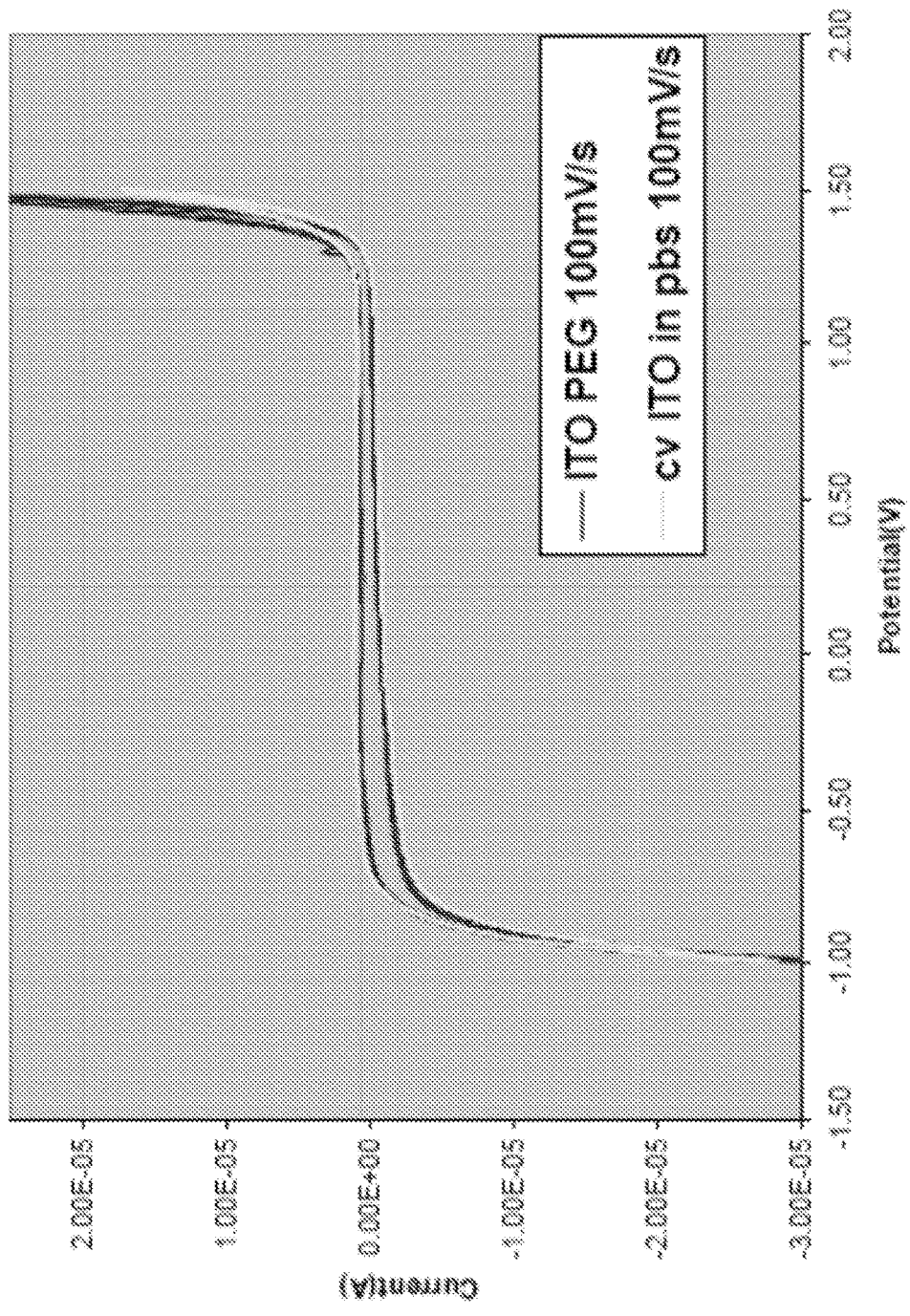
FIG. 7A: Cyclic voltammograms of Indium Tin Oxide (ITO) electrodes in PBS only. The region where pH change can occur is where there is oxygen evolution more than 1V in respect to Ag/AgCl reference electrode.
Figure 7B:
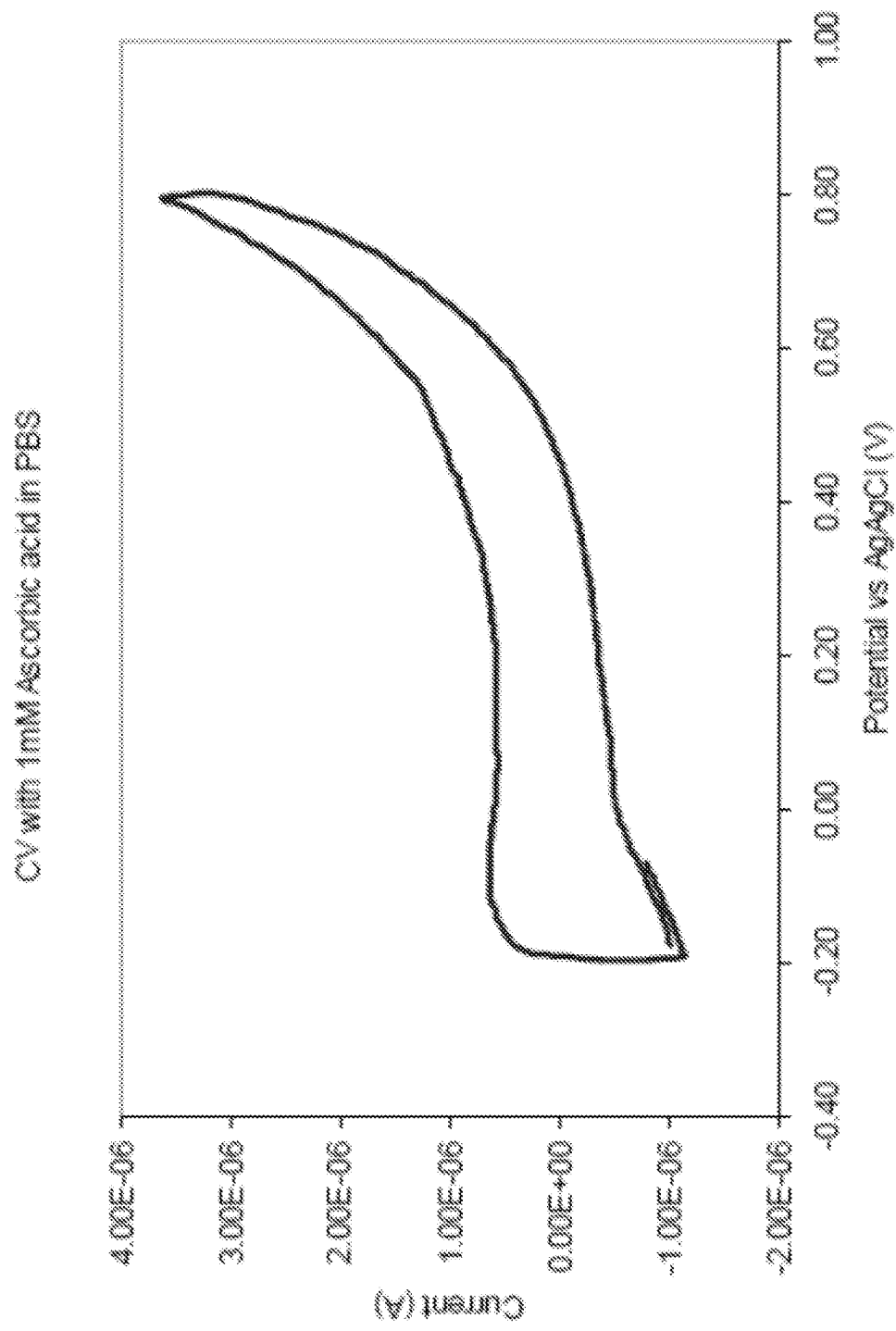
FIG. 7B: Cyclic voltammetric study of the oxidation of Ascorbic acid test in ITO electrodes. Current increase around 0.25V indicates the start of oxidation at ITO electrodes.
Figure 8A:
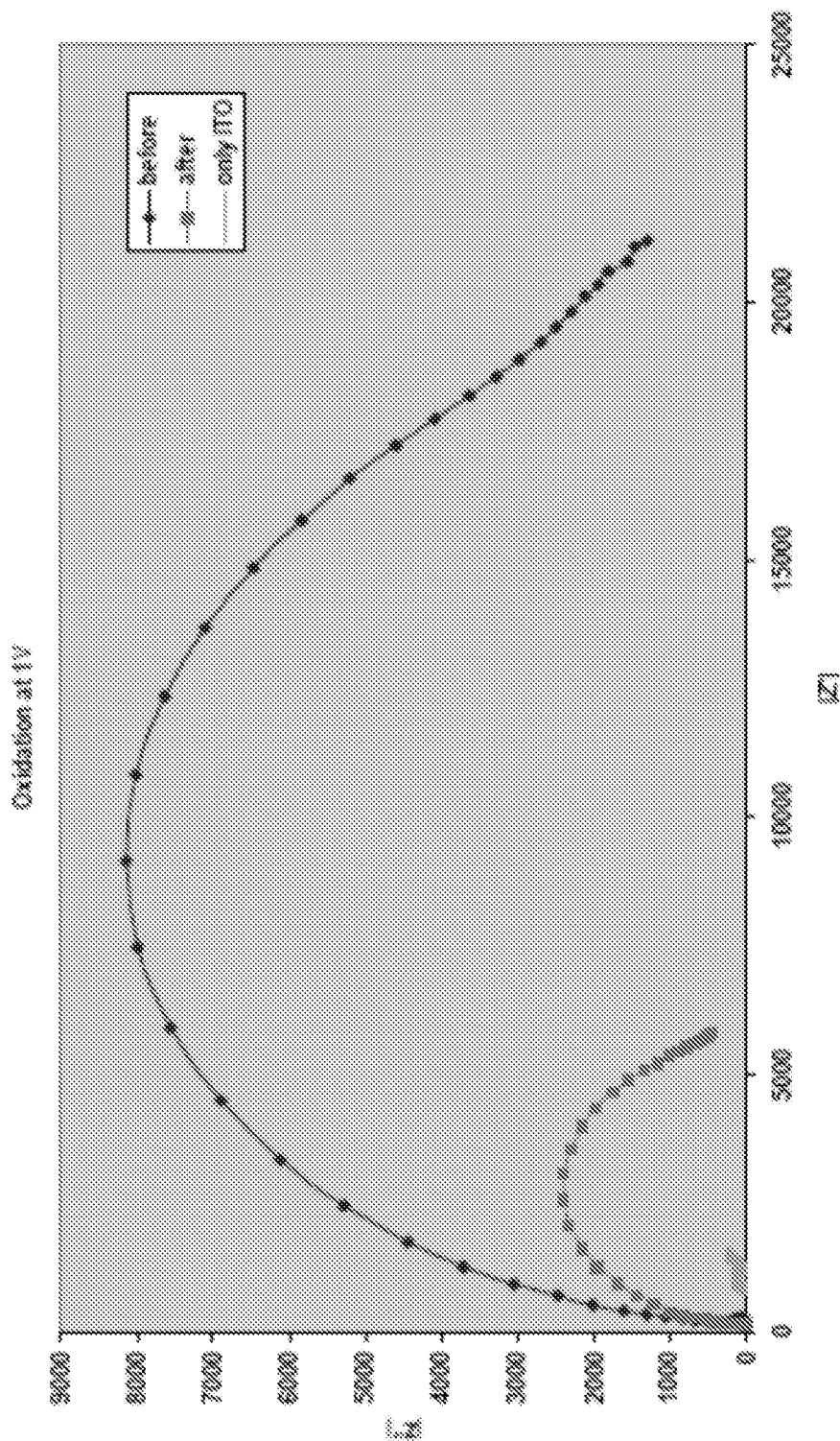
FIG. 8A: Application of 1V on the ITO-PEG surface in Phosphate buffer. Impedance changes before and after application of 1V indicates the changes or removal of PEG from electrode.
Figure 8B:
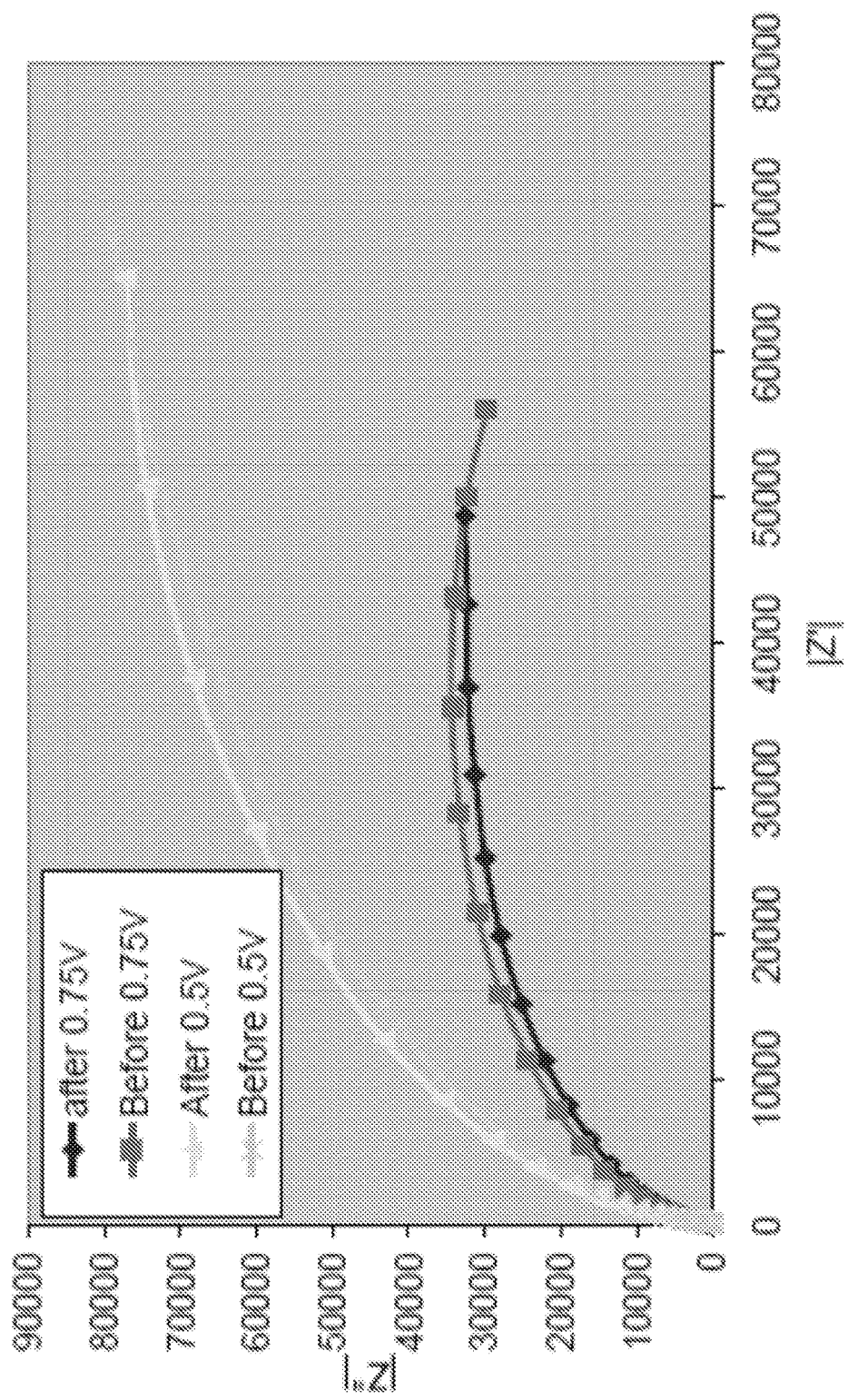
FIG. 8B: Oxidation of ascorbic acid at 0.5V and 0.75V at ITO-PEG surface. No change in impedance during ascorbic acid oxidation indicates PEG layers do not undergo any change.

$AH_2 \rightarrow A + 2H^+ + 2e^-$, where $AH_2$ is ascorbic acid ($C_6H_6O_6$) (as shown in FIG. 5). The electrode potential at which it oxidizes was less than 0.5V for Indium tin oxide material vs Ag/AgCl reference electrode (as shown in FIG. 7). This potential was less than the voltages needed for the oxygen evolution reaction in aqueous solution. Higher electrode potential (e.g >1V for ITO electrodes in just phosphate buffer) can damage the PEG layer (as shown in FIG. 8). The ascorbic acid also acted as a sacrificial species to prevent electrochemical degradation of the surface chemistry.

Electro-Reduction of Species to Produce OH− Ions.

Reduction of benzoquinone ($C_6H_4O_2$) into Hydroquinone ($C_6H_6O_2$) can produce OH− ions at −0.1V:

$$BQ + 2e^- + 2H_2O \rightarrow HQ + 2OH^-$$

This reduction reaction increased the pH at the electrode interface.

In the above examples the amount of $H^+$ or $OH^-$ ions generated will depend on the concentration of species present in solution (nM-mM range), potential applied (−2V to +2V), type of waveform (pulse, constant, sawtooth, sinusoidal, square wave at different frequencies and duty cycles), and diffusion of the species (can be varied due to additives in the solution). These parameters can be optimized to get different pHs at the each of the electrode element present in the multisite biosensor.

Example 2—pH Change Using Enzymatic Reactions

Enzymes such as oxidases, ureases or dehydrogenases have been known to consume or generate hydrogen during the reaction. For example:

$$\beta\text{-}d\text{-glucose} + O_2 \rightarrow d\text{-glucose-}\delta\text{-lactone} + H_2O_2$$

$$d\text{-glucose-}\delta\text{-lactone} + H_2O \rightarrow d\text{-gluconate} + H^+$$

Oxidation of glucose in the presence of glucose oxidase can produce $H^+$ ions that are used to change the pH near the proteins of interest.

Example 3—Co-Immobilization of Enzymes Along with Biomolecular Probes in a Biomolecular Interface Layer The enzymes when co-immobilized on the surface along with proteins brings them in close proximity so the $H^+$ produced by the enzymatic reaction will lead to a localized pH change that can affect protein binding (for example antigen-antibody binding and non-specific binding).

Example 4—Attaching the Enzymes to Magnetic Micro/Nanoparticles

Proteins are attached to micro/nanocavities of a solid surface on an electromagnet. The enzymes are separately attached to magnetic micro/nanoparticles in the solution. Controlling the electromagnet that is fabricated/placed underneath controls the local pH values. Then the enzymatic reaction is triggered by introducing the corresponding enzyme substrate (as shown in FIG. 6). Alternatively electrochemically active enzymes are used. The pH change is localized on the cavities and the protein interactions are modulated.

Example 5—Electrochemical Modulation of pH as Monitored by Fluorescence Intensity with Green Fluorescence Protein (GFP)

Electrode material used: The electrode material was indium tin oxide. The fluorescent protein used is GFP immobilized on a glass substrate which includes an array of electrodes. The GFP is applied as spots, each spot covers an area that overlaps with one electrode and an area that is not overlapping with an electrode.

Figure 11:
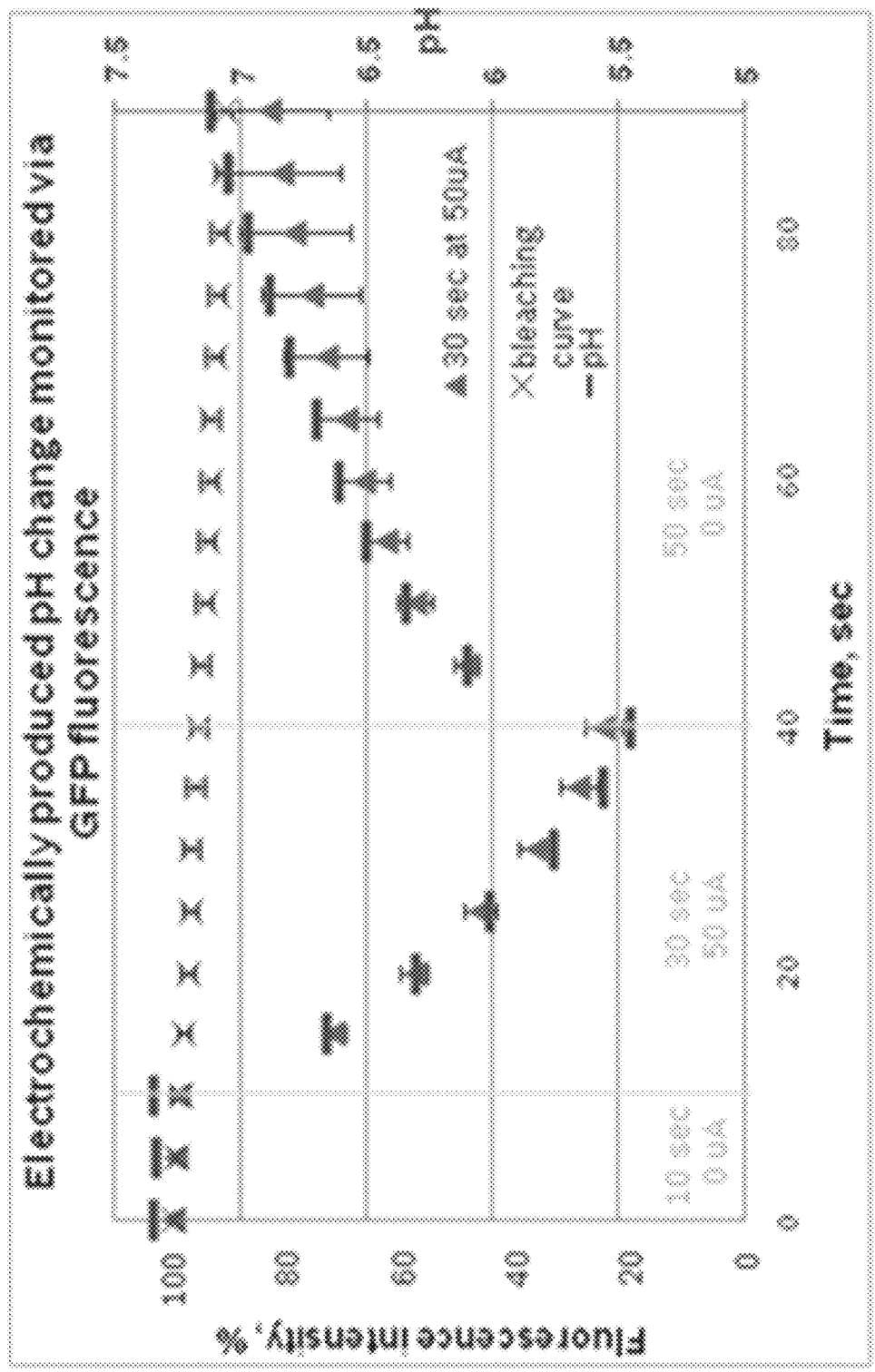
FIG. 11: shows the pH change at the surface of ITO working electrode generated via current-driven oxidation of a redox active molecule, 2-methyl-1,4-dihydroquinone, in diluted phosphate buffer (pH=7.4) containing 0.1M $Na_2SO_4$. After 10 seconds of induction, current (50 microamps) was applied for 30 second, which resulted in a drop of solution pH to 5.5, as was observed by a change in GFP fluorescence intensity (FIG. 10 is used as calibration curve to assess the pH values). After current was turned off, the pH recovered to neutral value within 50 seconds.

The pH change at the surface of ITO working electrode is generated via current-driven oxidation of a redox active molecule, 2-methyl-1,4-dihydroquinone, in diluted phosphate buffer (pH=7.4) containing 0.1M $Na_2SO_4$. After 10 seconds of induction, current (50 microamps) was applied for 30 second, which resulted in a drop of solution pH to 5.5, as was observed by a change in GFP fluorescence intensity. FIG. 10 is used as calibration curve to assess the pH values. After current was turned off, the pH recovered to neutral value within 50 seconds (as shown in FIGS. 11 and 12B).

Example 6—Preventing Reaction with Nucleophiles

Figure 32:
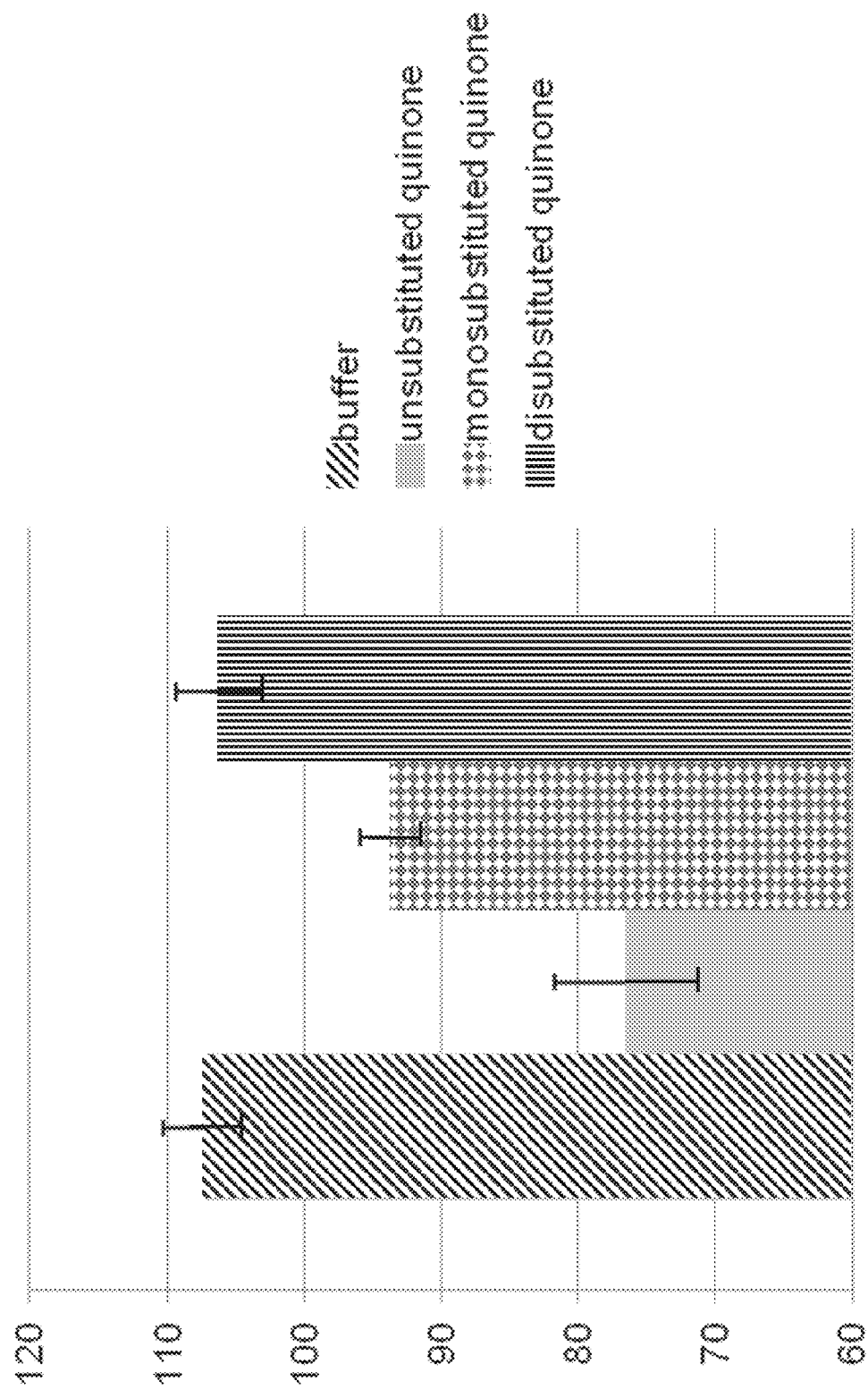
FIG. 32: demonstrates an effect of substitution in benzoquinones on the stability of proteins according to example embodiments of the preset invention.

Para-benzoquinones and ortho-benzoquinones (compounds 2, 4, 6, and 9 in FIG. 31) are susceptible to nucleophilic attack at the double bond of the ring (positions 2, 3, 5 and 6 in structure 2 of FIG. 31, positions 3, 4, 5 and 6 in structure 4 of FIG. 31, and positions 2 and 3 in structure 6 of FIG. 31). Introducing substituents at some or all of those positions can mitigate the problem of nucleophilic attack. For example, 1,4-benzoquinone (structure 2 in FIG. 31, where R1, R2, R3 and R4 are H) undergoes Michael addition reaction with amino groups of proteins (Loomis et al., Phytochemistry, 5, 423, (1966) and U.S. Pat. No. 6,753,312 B2). On the other hand, 2,5-disubstituted 1,4-benzoquinones (structure 2 in FIG. 30, where R1 and R3 are H, and R2 and R4 are groups other than H) do not show susceptibility to Michael addition reaction in the presence of proteins and are more suitable for use in biological buffers. FIG. 32 demonstrates the effect of substitution on protein stability in the presence of benzoquinones. Fluorescence intensity of Green Fluorescent Protein (GFP) was measured after incubation with three different benzoquinones in phosphate buffered saline for 30 min (concentration of benzoquinones was 0.5 mM). The difference in fluorescence intensity indicates the varied effect that the different substitutions in benzoquinones have on the stability of GFP. Fluorescence intensity of GFP is indicative of its structural integrity. Losses in fluorescence intensity usually indicate loss of its tertiary structure (protein denaturation) (Yin D. X., Zhu L., Schimke R. T. Anal. Biochem. 1996, 235:195-201). As shown in FIG. 32, GFP retains 100% of its fluorescence intensity after incubation with di-substituted benzoquinone for 30 min, while incubation with unsubstituted benzoquinone and mono-substituted benzoquinone causes 25% and 7% loss in fluorescence intensity, respectively.

Example 7—Tuning Water Solubility

Water solubility of aromatic compounds can be improved by introducing charged groups or atoms with lone pair electrons that can participate in hydrogen bonding. Such groups are, for example, —OH, —$CH_2OH$, —$OCH_3$, —COOH, —$SO_3H$, —$NH_2$, —$NH_3Cl$, —ONa. Sugars, amino acids, and peptides can also improve water solubility of quinones. Synthetic macromolecules such as polyethyleneglycoles can be used as substituents as well.

Example 8—Adjusting Redox Window

Reduction/oxidation potential of quinones can be tuned to fit the needs of specific application. By introducing electron-donating groups (such as alkyl, hydroxyl, alkoxy, methoxymethyl, morpholinomethyl, amino and chloro substituents) redox potential can be pushed towards higher voltage. Conversely, electron-withdrawing groups (such as nitro, cyano, carboxylic acid or carboxylic ester groups) will push redox potential towards lower voltage.

In an example embodiment, the mechanism of oxidation of hydroquinones in aqueous solutions involves two steps:

transfer of electrons and transfer of protons. Introducing electron-withdrawing or electron-donating substituents addresses the first step of the process. Oxidation potential of hydroquinones can also be lowered by introducing substituents that are capable of forming intramolecular hydrogen bonds with hydroxyl groups of hydroquinone. Such hydrogen bonding weakens the bond between hydrogen and oxygen of hydroxyl group, therefore lowering an overall energy barrier for oxidation reaction. Examples of such R groups are $CH_2OH$, $CH_2OCH_3$, morpholinomethyl, and $COOCH_3$.

Having the ability to select molecules which undergo electrochemical transformation through the same mechanism, but at different potentials enables one to accommodate different pH conditions and avoid undesirable electrochemical reactions involving other redox active components in the system. For example, for applications involving DNA synthesis, it is important to keep the voltage below the reduction potentials of pyrimidine bases, nucleosides, and nucleotides (1V vs. NHE in aqueous solution pH 8) (Steenken, S. J Am Chem Soc, 1992, 114: 4701-09).

Autooxidation of hydroquinones is another issue. In an example embodiment, in order to avoid oxidation, a quinone derivative with high enough electrochemical oxidation potential that is resistant to spontaneous chemical oxidation by molecular oxygen is used.

Conversely, benzoquinones with low enough reduction potentials should be chosen for systems where reducing agents, like mercaptoethanol, glutathione, and dithiothreitol are present in solution. Examples of such applications are DNA synthesis, electrophoresis, and immunoassays.

Figure 33:
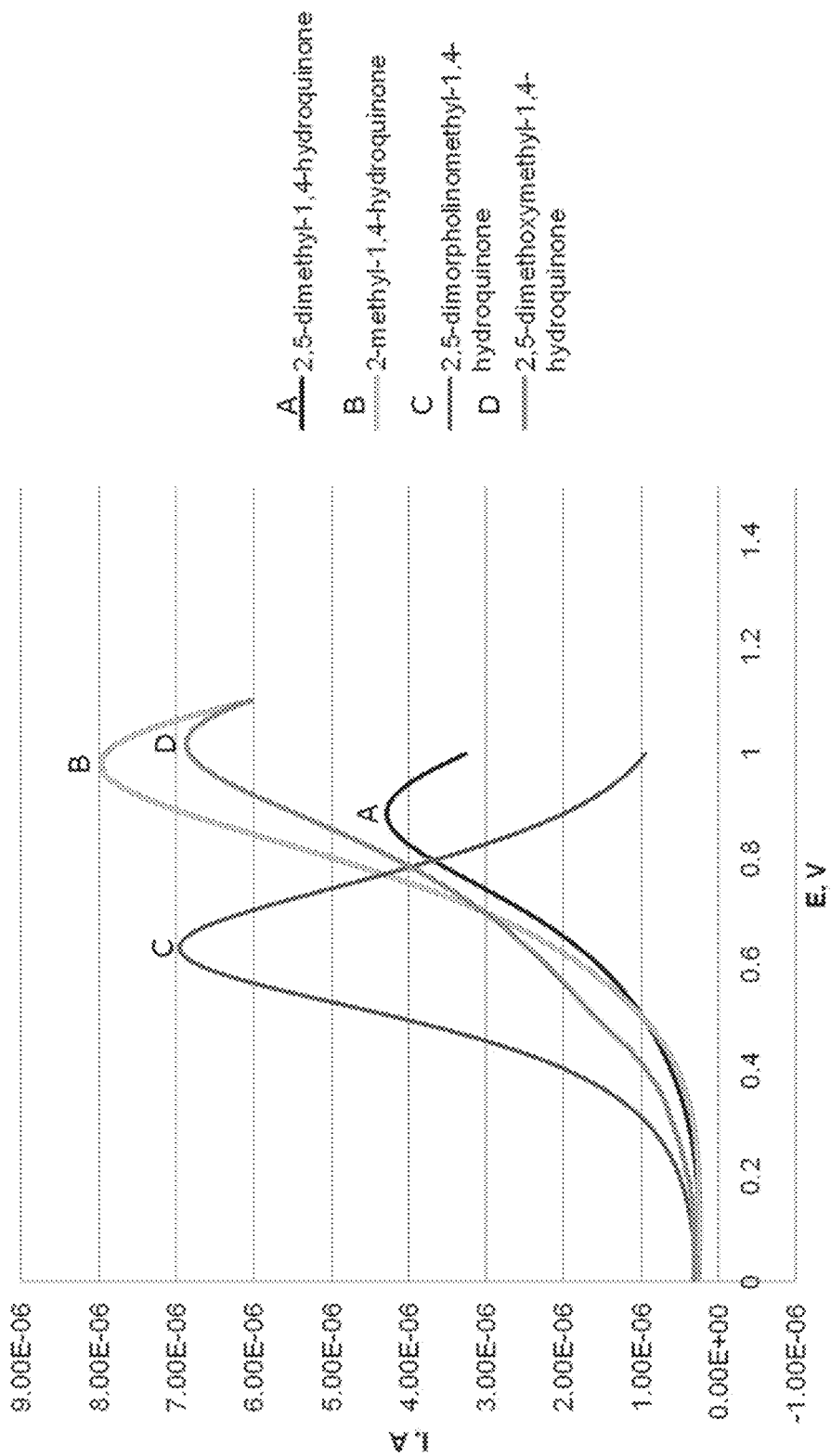
FIG. 33: shows square wave voltammograms of substituted quinones in buffered solution (vs. Ag/AgCl) according to example embodiments of the present invention.

The redox potential of quinones is affected by the pH of the solution. It is easier to oxidize hydroquinones in more basic pH, whereas more acidic pH will require higher oxidation potentials. This, in turn, affects stability of hydroquinones towards autooxidation by oxygen in air. Therefore, if one needs to work in basic pH, using a quinone with higher oxidation potential will improve the stability of electrochemical system. FIG. 33 shows that there are different oxidation potentials for different substituents in quinones (FIG. 33 A-D), and therefore, the oxidations potential can be tuned by varying the substituents in quinones.

Example 9—Synthesis of Substituted Quinones

Figure 34:
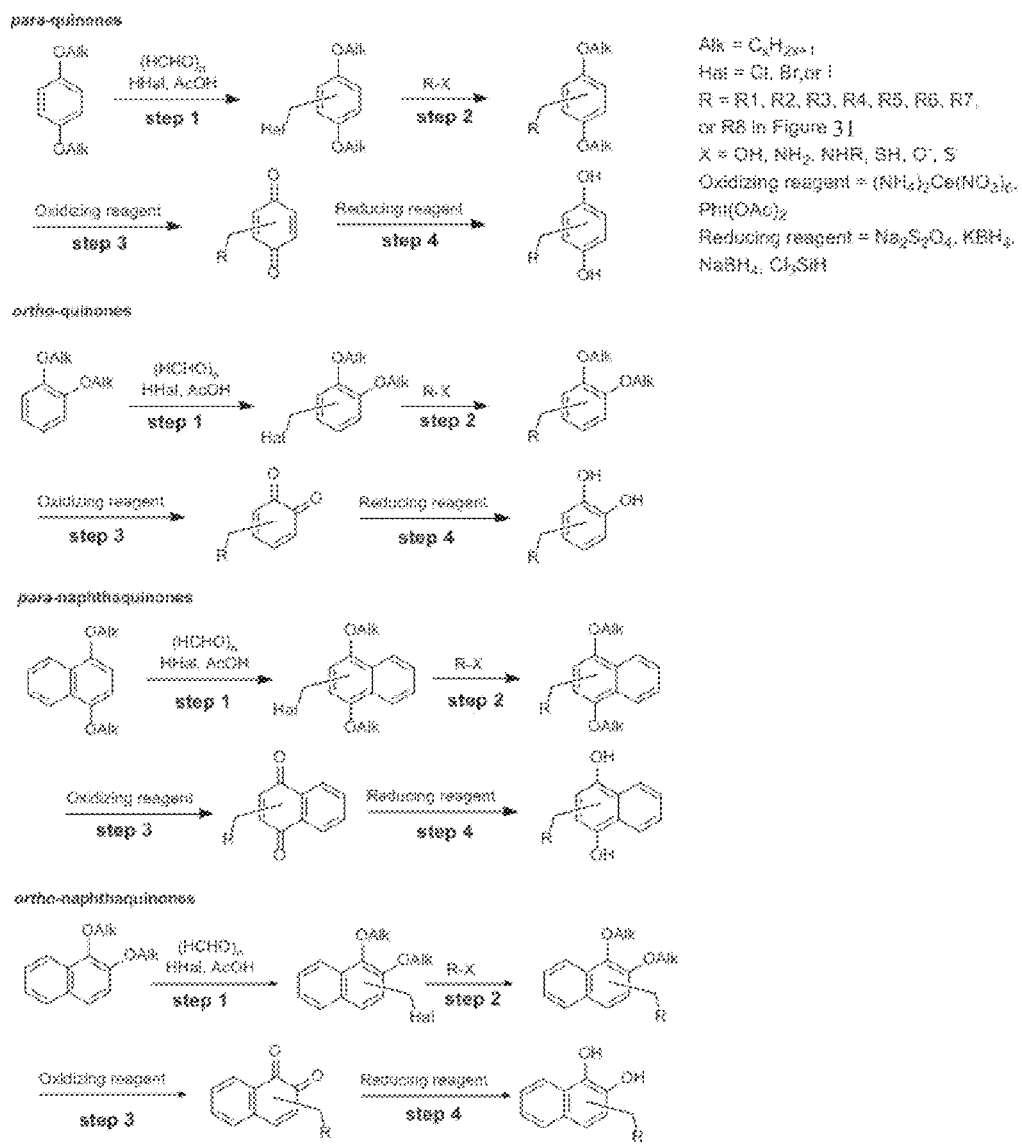
FIG. 34: shows steps for the synthesis of substituted hydroquinones and benzoquinones.

Scheme 1 shown in FIG. 34 is a representation of a synthesis of substituted quinone according to an example embodiment of the present invention.

Example 10—2,5-dimethyl-1,4-hydroquinone

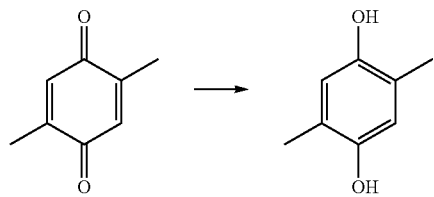

Sodium dithionate (18.7 g, 107.3 mmol, 7.3 equiv) was dissolved in 20 mL $H_2O$ and loaded into a reparatory funnel. Next, a solution of benzoquinone (2 g, 14.7 mmol, 1 equiv) in 75 mL diethyl ether was added. The diphasic mix was stirred vigorously for 30 minutes and the organic layer changed color from orange to pale yellow. Organic phase was washed with brine, dried over $MgSO_4$, and concentrated to yield a white solid (1.69 g, 83%).

Example 11—1,4-Bis(bromomethyl)-2,5-dimethoxybenzene

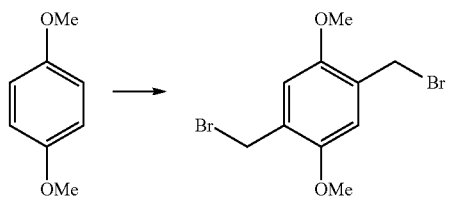 [SMILES: COc1ccc(OC)cc1 ; COc1cc(CBr)c(OC)cc1CBr]

Paraformaldehyde (Aldrich, 4.27 g, 144.75 mmol) and HBr/AcOH (Fluka, 33%, 30 mL) were added slowly to a stirred solution of 1,4-dimethoxybenzene (Aldrich, 10.00 g, 72.37 mmol) in glacial acetic acid (Fisher, 50 mL). The mixture was stirred at 50° C. for one hour, allowed to cool to room temperature, and then hydrolyzed in water (200 mL). The white solid was collected by filtration, suspended in $CHCl_3$ (50 mL), and refluxed for 10 min. After cooling to room temperature, the white solid was again collected by filtration and washed with water (15.75 g, 67%). NMR spectra were obtained experimentally to confirm the chemical structure of the resulting compound and its purity. NMR results were as follows: $^1H$ NMR (300 MHz, $CDCl_3$) δ: 6.88 (s, 2H), 4.54 (s, 4H), 3.87 (s, 6H) ppm.

Example 12—1,4-dimethoxy-2,5-dimethoxymethylbenzene

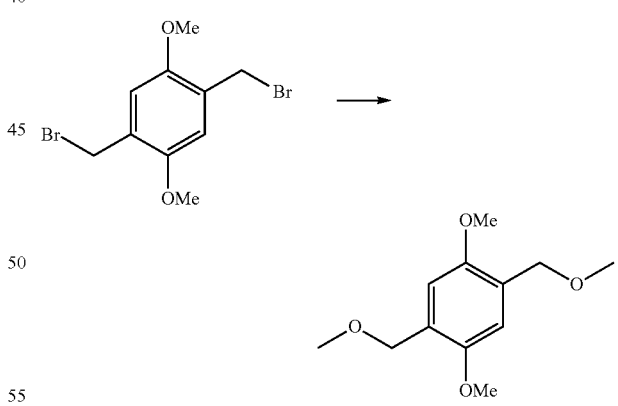

A dry round bottom flask was charged with 2,5-dibromomethyl-1,4-dimethoxy-benzene (3 g, 9.26 mmol, 1.0 equiv), anhydrous $K_2CO_3$ (25.6 g, 185 mmol, 20 equiv), and dry methanol (200 mL). The reaction mixture was heated to reflux for 30 min, then cooled to ambient temperature, filtered, and concentrated to a crude white solid. The solid was resuspended in water and extracted with ethyl acetate, dried over $MgSO_4$, and concentrated. The residue was recrystallized in hexanes as a pale yellow powder (1.2 g, 57%). Retention factor (Rf) (50% EtOAc/hexanes)=0.65.

Example 13—2,5-dimethoxymethyl-1,4-benzoquinone

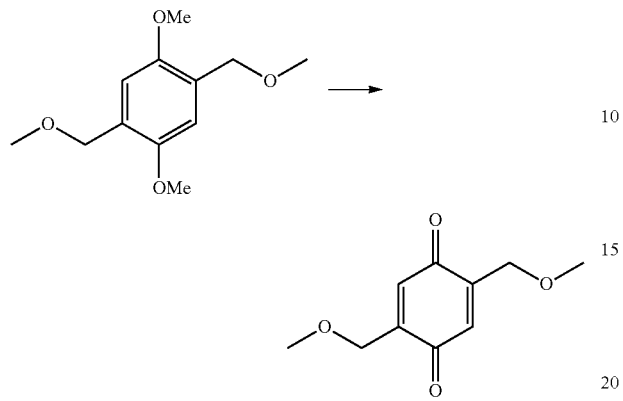

A solution of 1,4-dimethoxy-2,5-dimethoxymethylbenzene (1.2 g, 5.24 mmol, 1.0 equiv) in acetonitrile (0.1 M, 52 mL) was treated with a solution of cerium ammonium nitrate (5.8 g, 10.6 mmol, 2.02 equiv) in water (8 mL). The reaction mixture was stirred under argon at ambient temperature for 30 minutes, then diluted with water, and extracted with dichloromethane. The combined organic layers were washed with water, dried over $Na_2SO_4$, and concentrated to an orange solid. The crude mix was purified by column chromatography on deactivated silica gel (0-5% ethyl acetate/hexanes) to yield yellow crystals (300 mg, 67%). Rf (50% EtOAc/hexanes)=0.7; $^1$H NMR (300 MHz, $CDCl_3$) δ: ppm; UV-Vis=268 nm.

Example 14—2,5-dimethoxymethyl-1,4-hydroquinone

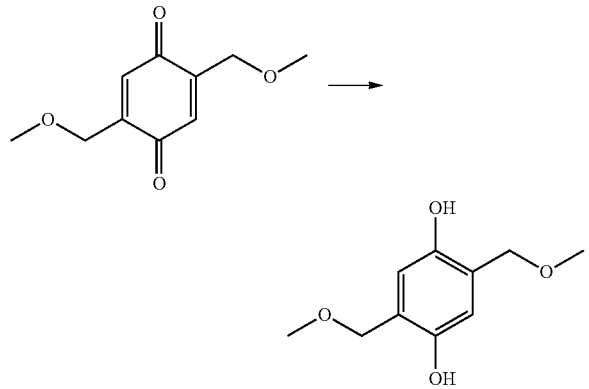

The benzoquinone obtained according to the reaction of Example 13 (200 mg, 1.02 mmol, 1.0 equiv) in 2.5 mL EtOAc was treated with a solution of sodium dithionate (1.3 g, 7.44 mmol, 7.3 equiv) in 2 mL H2O. The diphasic mix was stirred vigorously for 30 minutes and the solution changed colors from bright to pale yellow. The mixture was diluted with water, extracted with ethyl acetate, dried over $MgSO_4$, and concentrated to a white powder (96 mg, 48%).

Example 15—1,4-dimethoxy-2,5-dihydroxymethylbenzene

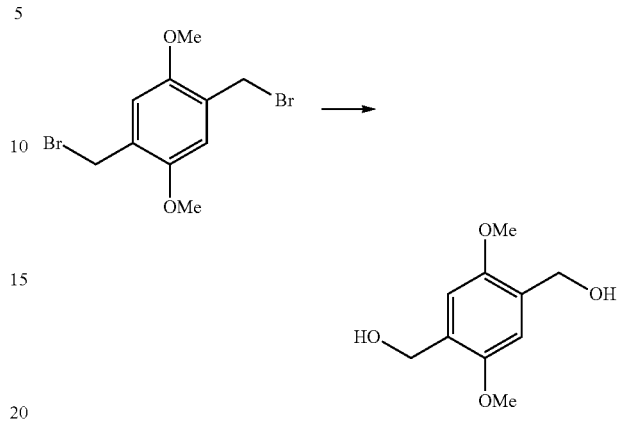

A dry round bottom flask was charged with 2,5-dibromomethyl-1,4-dimethoxy-benzene (5 g, 15.4 mmol, 1.0 equiv) and NaOH (77 mL of 1.0 M solution, 77 mmol, 5.0 equiv), 12 mL H2O, and 38 mL THF. The reaction mixture was sealed and heated to 80° C. for 6 h. After cooling, the reaction mixture was concentrated by rotary evaporation to a crude solid that was recrystallized in hexanes to a white powder (3 g, 60%). Rf (80% EtOAc/hexanes)=0.2.

Example 16—2,5-dimethoxymethyl-1,4-benzoquinone

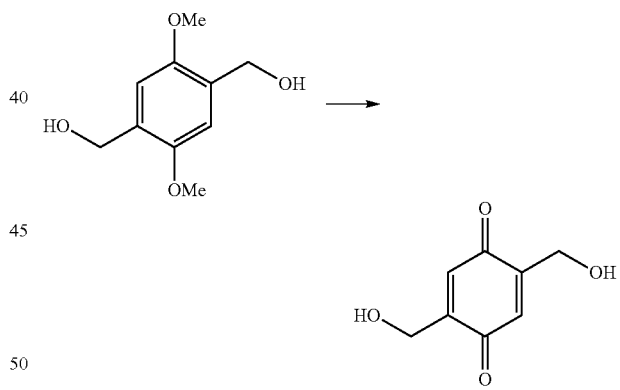

A solution of 1,4-dimethoxy-2,5-dihydroxymethylbenzene (1.0 g, 5.04 mmol, 1.0 equiv) in acetonitrile (0.2 M, 25 mL) was treated with a solution of cerium ammonium nitrate (5.5 g, 10.1 mmol, 2.0 equiv) in water (33 mL) at 0° C. The reaction mixture was stirred under argon at ambient temperature for 30 min, and then extracted with EtOAc. The combined organic layers were dried over $Na_2SO_4$ and concentrated to an orange-red solid. The crude mix was purified by column chromatography on deactivated neutral alumina (0-100% ethyl acetate/hexanes) to yield yellow crystals (300 mg, 67%). Rf (80% EtOAc/hexanes)=0.4; $^1$H NMR (DMSO, 500 MHz): 6.6 (s, 2H), 5.3 (s, 2H), 4.3 (s, 4H), ppm; $^{13}$C NMR (DMSO, 125 MHz): 187.4, 149.1, 129.8, 57.0 ppm; UV-Vis=260 nm.

Example 17—2,5-dihydroxymethyl-1,4-hydroquinone

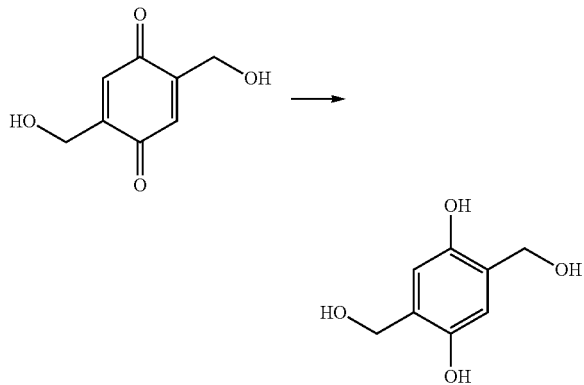

The benzoquinone obtained according to the reaction of Example 16 (60 mg, 0.36 mmol, 1.0 equiv) in 0.6 mL EtOAc was treated with a solution of sodium dithionate (453 mg, 2.6 mmol, 7.3 equiv) in 0.7 mL $H_2O$. The diphasic mix was stirred vigorously for 30 minutes and the solution changed colors from bright to pale yellow. The mixture was diluted with water, extracted with ethyl acetate, dried over $MgSO_4$, and concentrated to a crude solid that was purified by column chromatography on deactivated neutral alumina under Ar to yield a white powder (26 mg, 30%). UV-Vis=297 nm.

Example 18—Open Loop Method

According to an example embodiment, a method, termed open loop pH control, involves using electric current or electric potential shaping to maintain a desired pH of a solution close to the electrode. The method relies on an understanding of the electrochemical components of the system, the major constituents being the reduction/oxidation properties of the quinone, the starting pH of the solution, the electron transfer coefficient of the electrode material, the redox molecule concentration, the salt concentration, and the buffer composition and concentration. All these components impact how the electrochemical reaction changes the pH close to the electrode. With this understanding and by incorporating experimental data, a series of models can be used to define the waveforms to change the pH as required.

Figure 35:
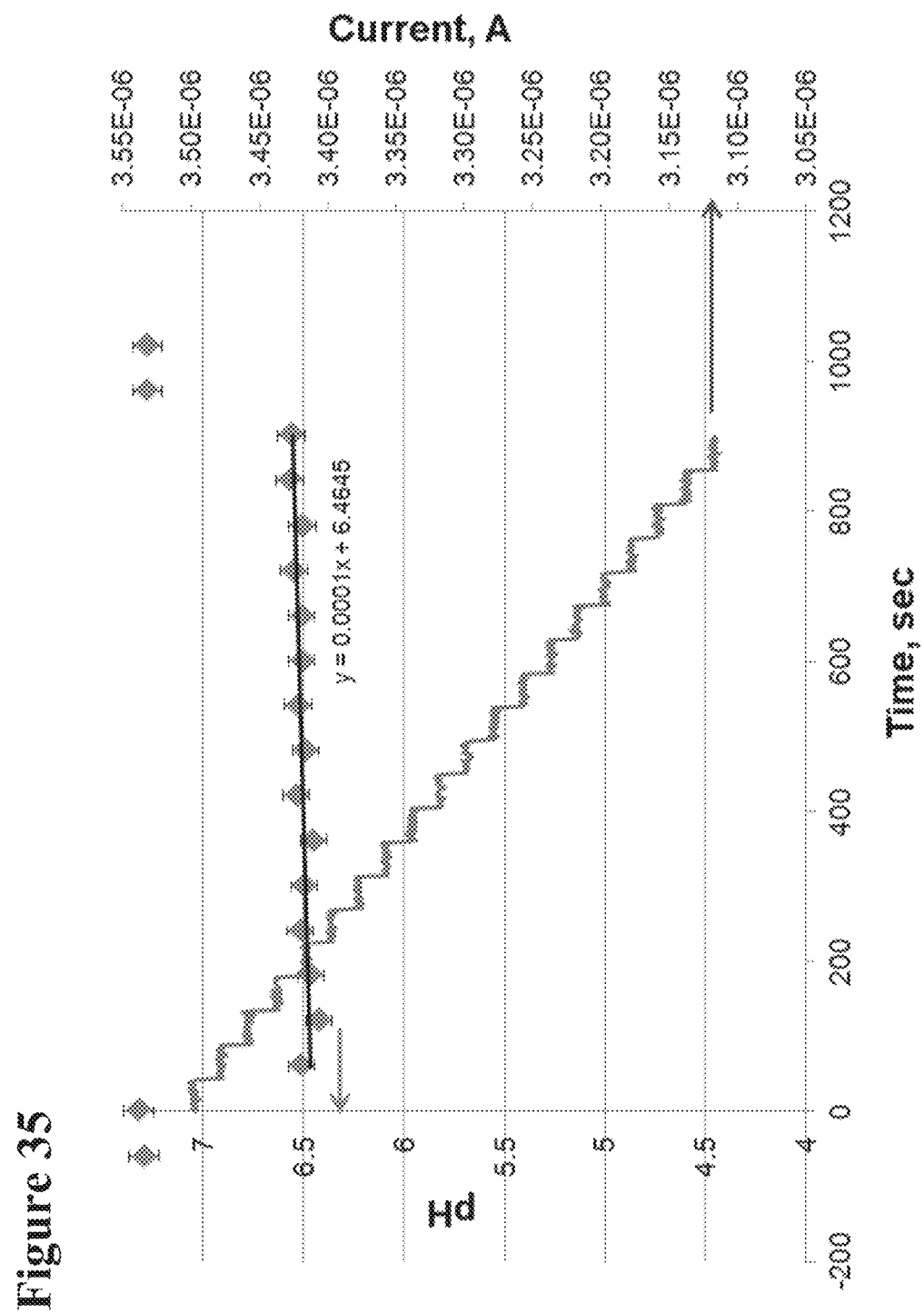
FIG. 35: illustrates an open loop waveform used to maintain the pH of a solution close to an electrode, according to an example embodiment of the present invention.

FIG. 35 shows an outcome from an open loop waveform experiment designed to hold the pH of the solution close to the electrode at pH 6.5 over 15 minutes. The stepped trace approximately extending between current values $3.12\,e^{-6}$ and $3.50\,e^{-6}$ correlates with the current applied to the system (right axis). The approximately straight trace correlates with the observed pH close to the electrode surface, which is measured by analyzing the pH dependent fluorescence of green fluorescent protein bound to the surface (left axis).

Figure 36:
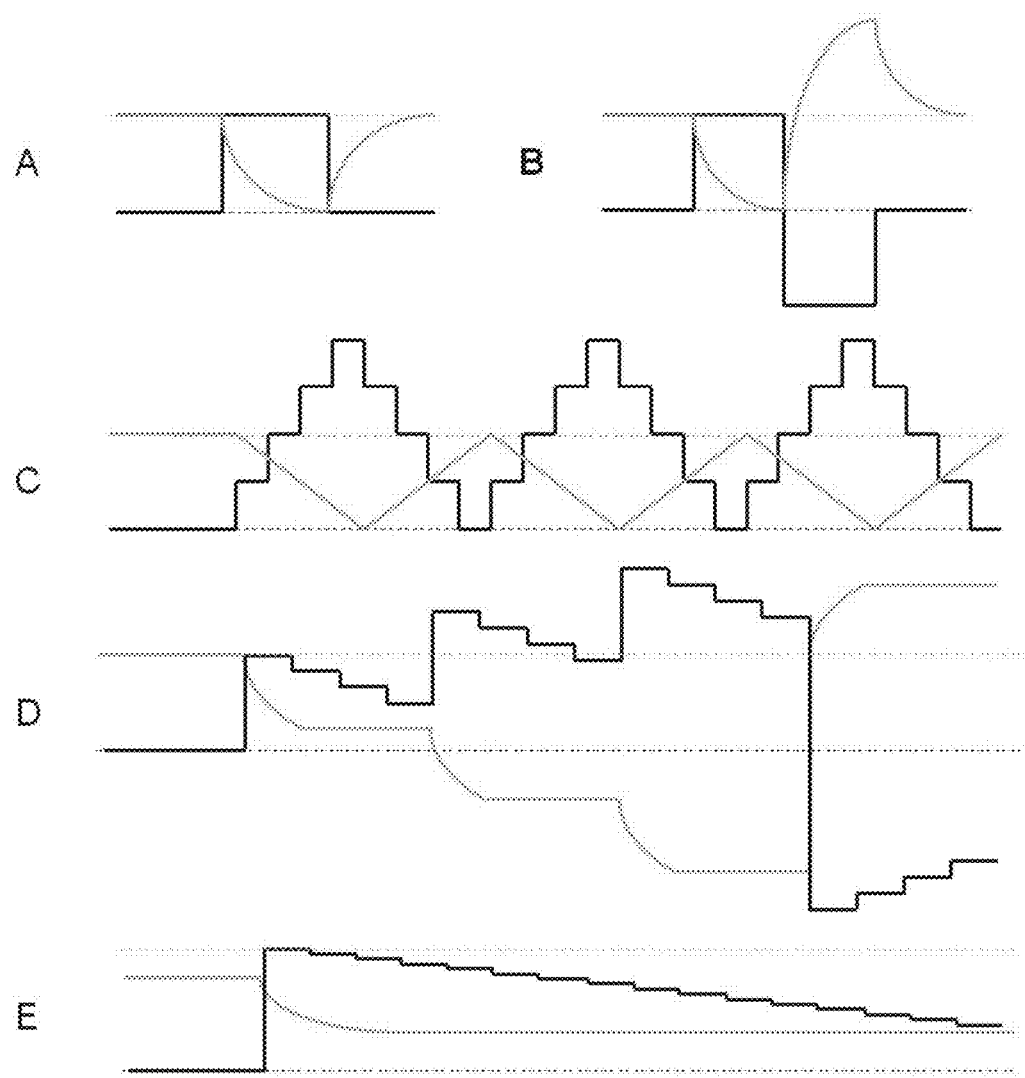
FIG. 36: illustrates examples of waveform shaping for pH control, according to example embodiments of the present invention.

FIG. 36 shows four different examples of waveforms (A-E) usable to shape and control the pH of the solution. The black line is the current/potential driven input and the grey line is the resultant pH change in the solution close to the electrode surface plotted over time.

If the relevant electrochemical components of a system remain fixed, these waveforms can be used to reproducibly generate the same pH change profile of the solution on demand without additional complexity. The method can be implemented using various electrode systems, schematics of example setups are shown in FIG. 40A-B. The method requires a minimum of 2 electrodes 815, 820. Initially, the open circuit potential of the solution close to the electrode 700 can be measured by applying zero current between the 2 electrodes 815, 820. In this state, one electrode acts as the sense electrode (SE) 815 and the second acts as a reference electrode (RE) 820. Once the starting OCP is known a current 800 (FIG. 40A) or an electric potential 804 (FIG. 40B) is applied to the electrodes 815, 820 based on the desired pH change. While a current or potential is being applied, one electrode 815 acts as a working electrode (WE) and the second electrode 820 acts as a counter electrode (CE). This is the simplest case in that the conditions of the system must remain fixed, but to improve accuracy, a method for continuous feedback of the system state is preferred.

Example 19—Closed Loop Method

According to another example embodiment, a method, termed closed loop pH control, uses the open circuit potential as a feedback measurement to control the current or potential.

Figure 41:
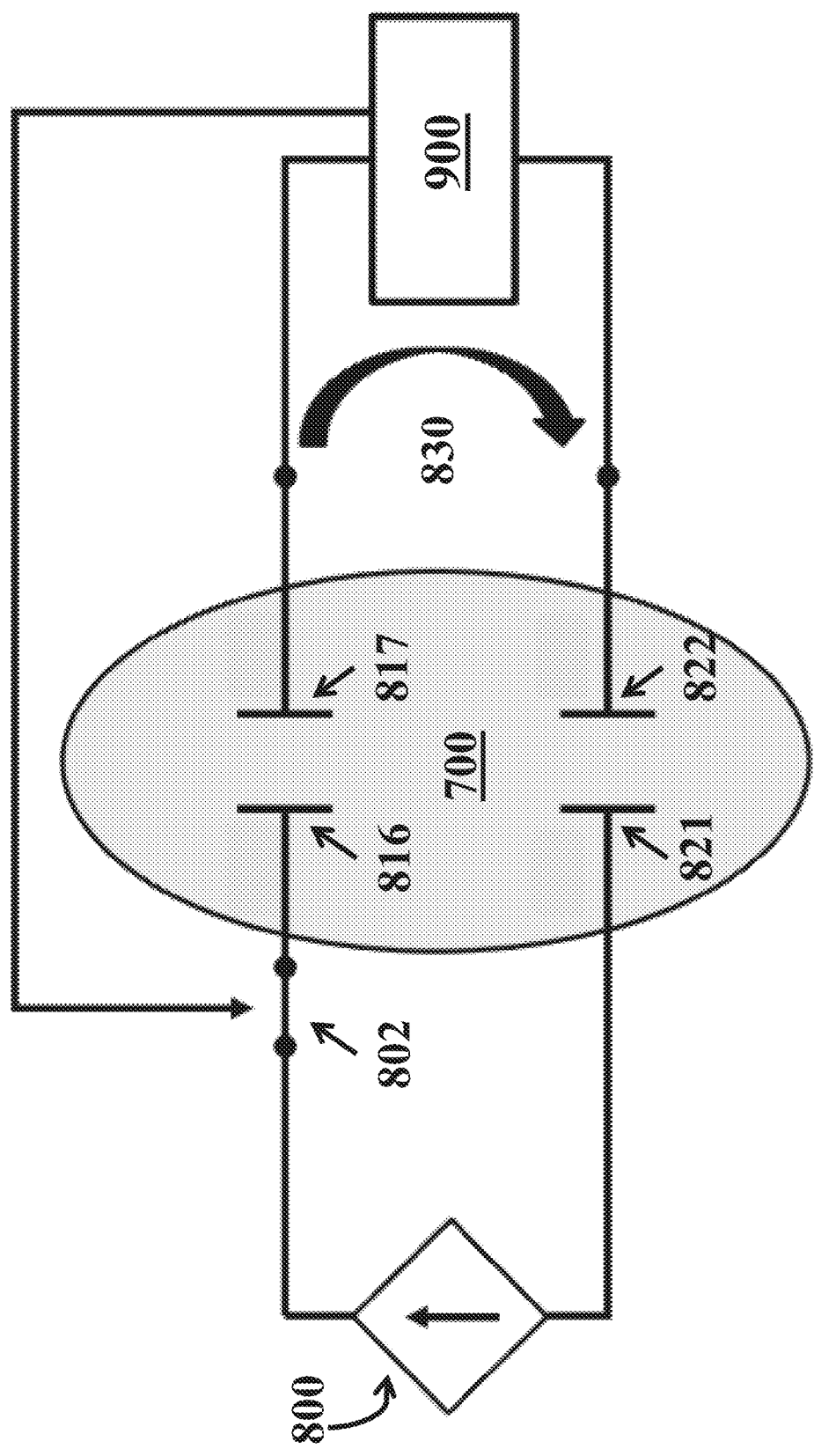
FIG. 41: illustrates a closed loop single controlled current source, according to an example embodiment of the present invention.
Figure 42:
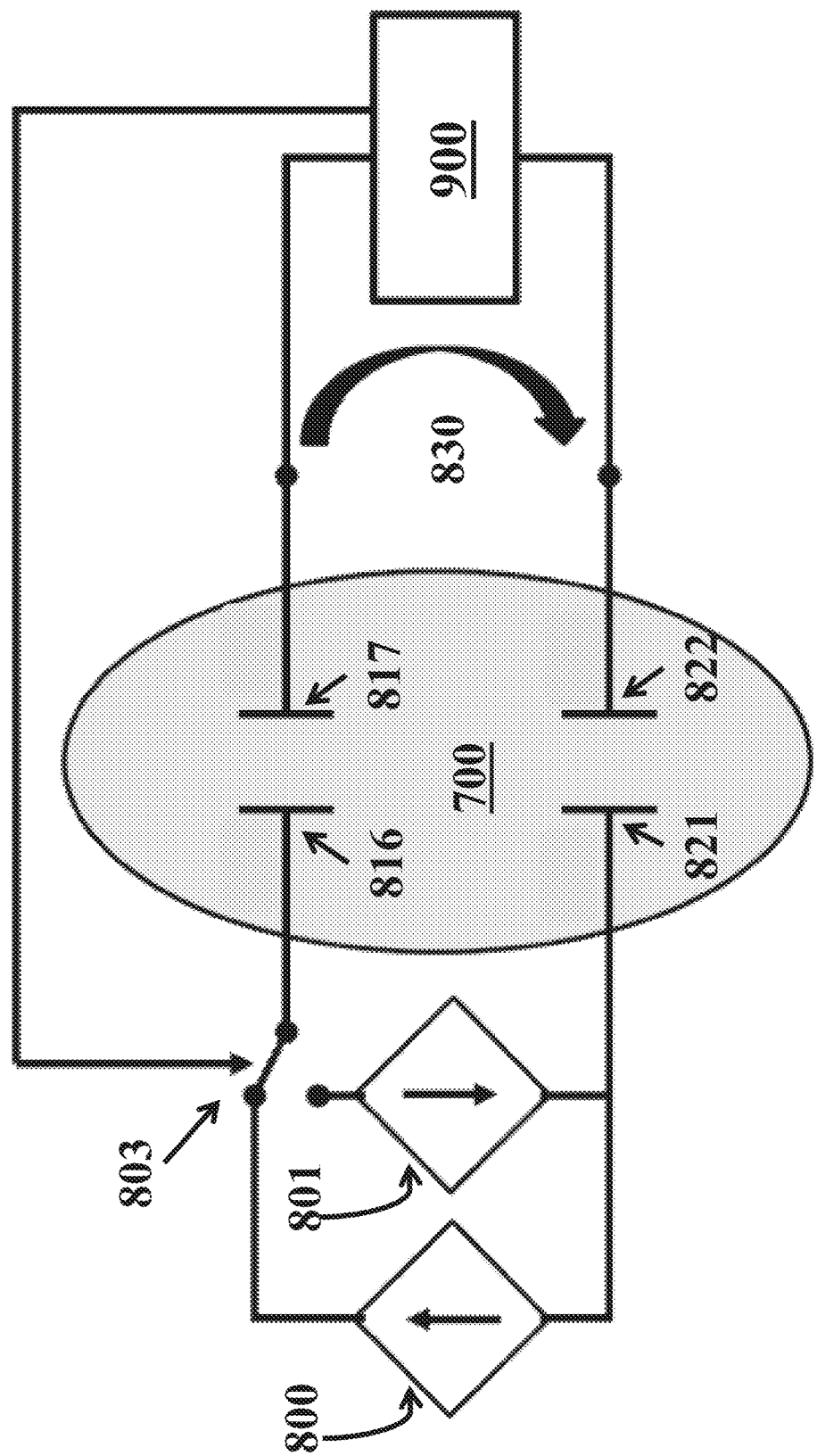
FIG. 42: illustrates a closed loop dual controlled current source, according to an example embodiment of the present invention.
Figure 43:
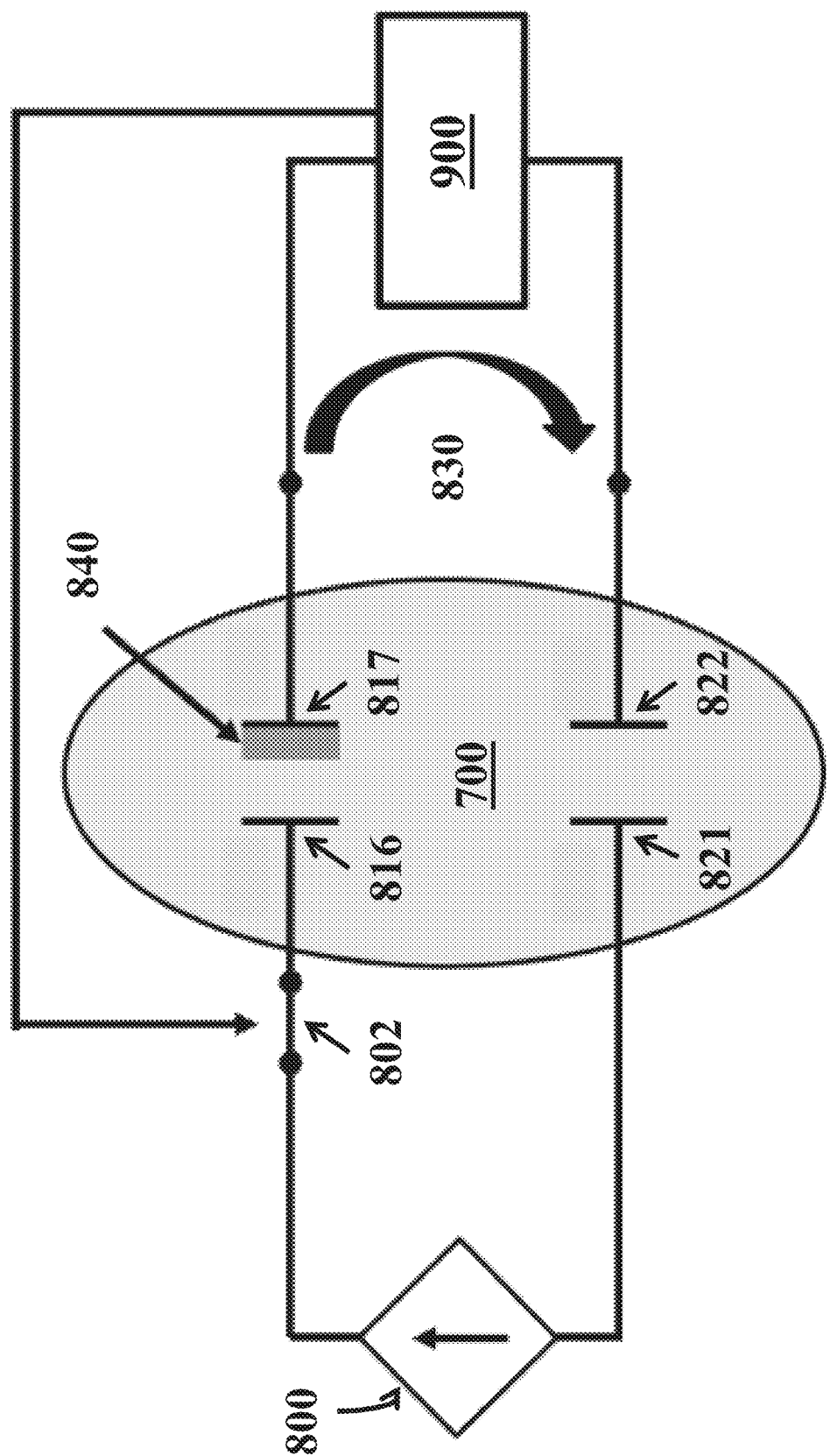
FIG. 43: illustrates a closed loop single controlled current source with a PANI coated sense electrode, according to an example embodiment of the present invention.
Figure 44:
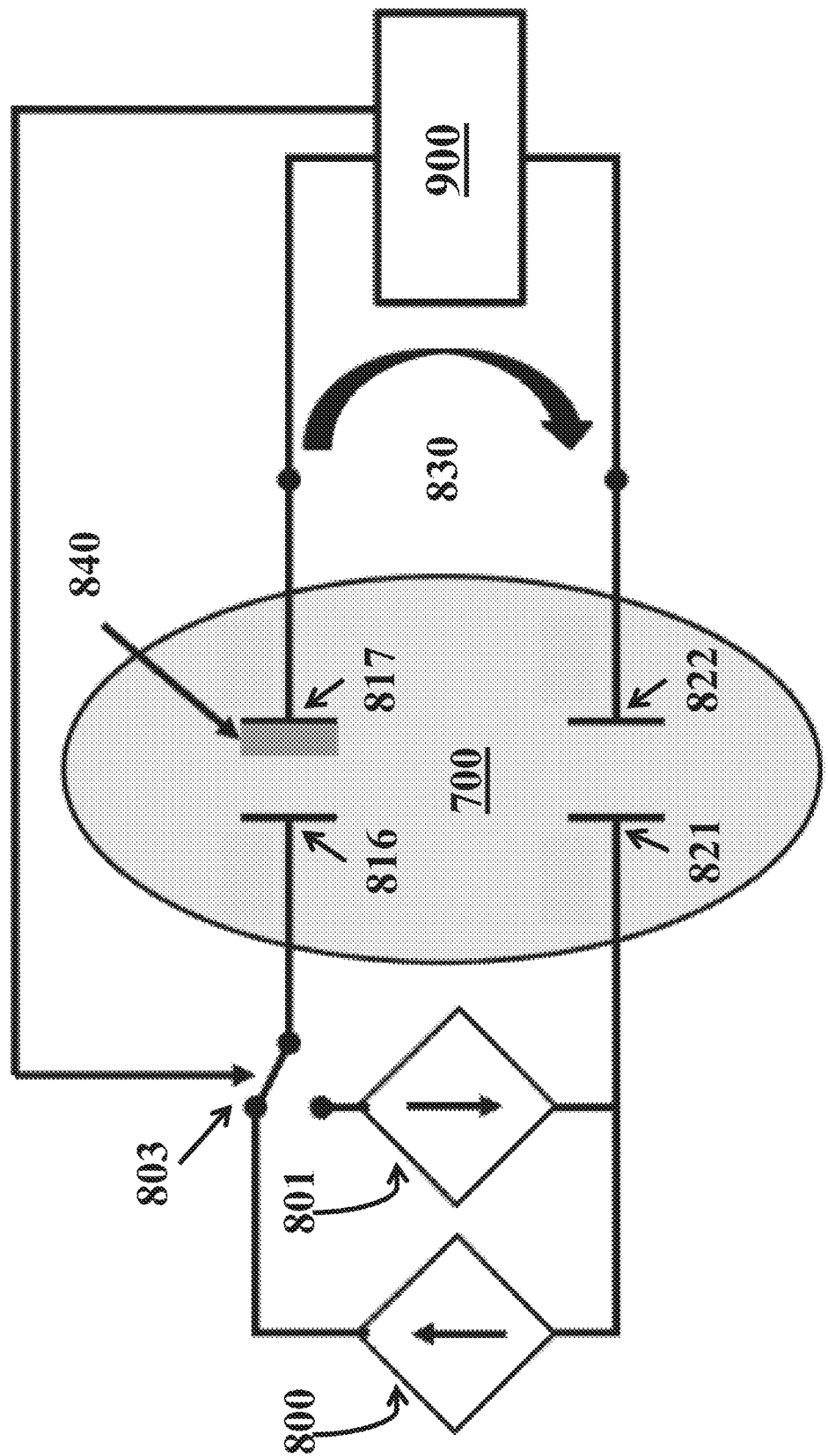
FIG. 44: illustrates a closed loop dual controlled current source with a PANI coated sense electrode, according to an example embodiment of the present invention.
Figure 45:
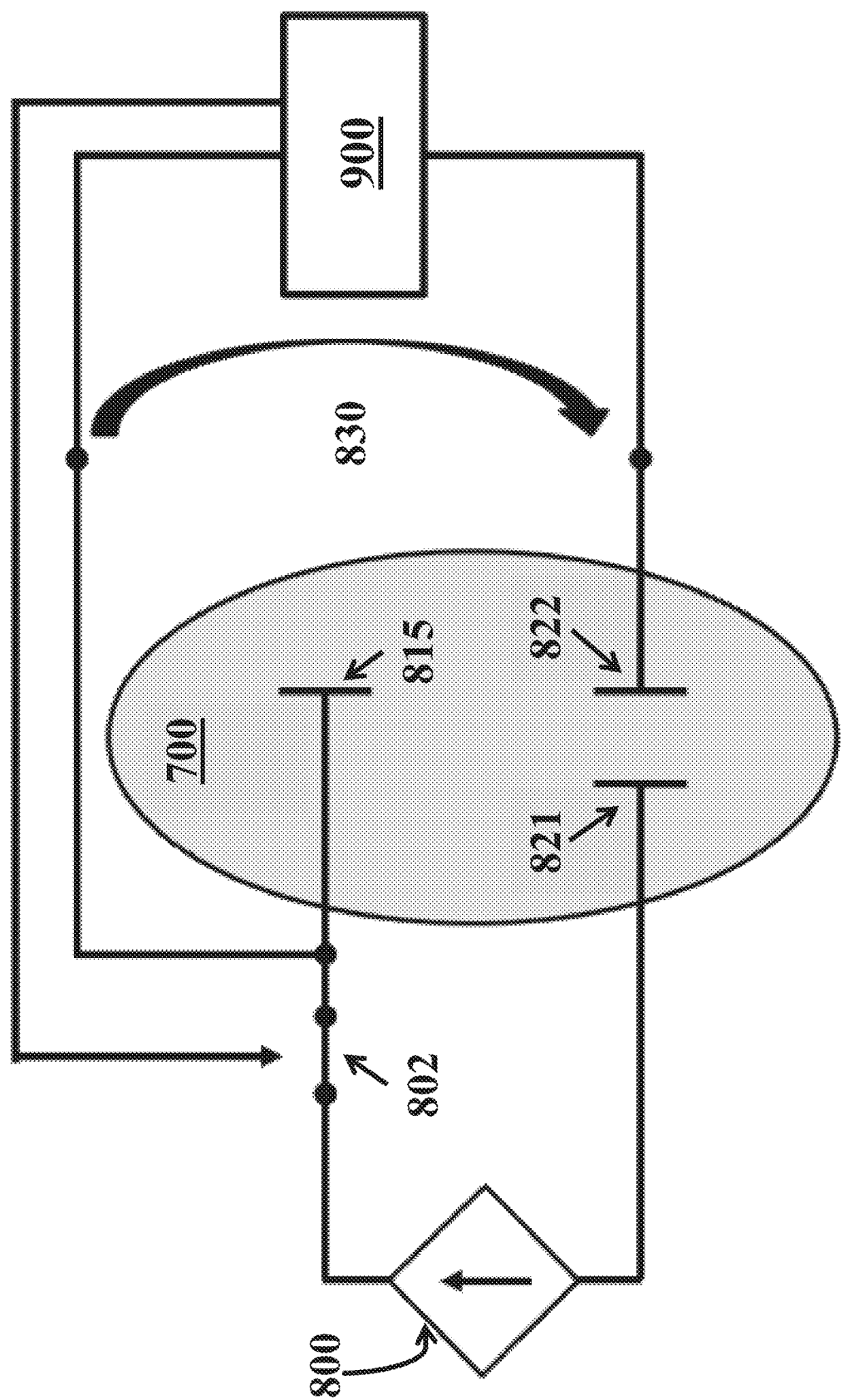
FIG. 45: illustrates a closed loop single controlled current source with a combined working and sense electrode, according to an example embodiment of the present invention.
Figure 46:
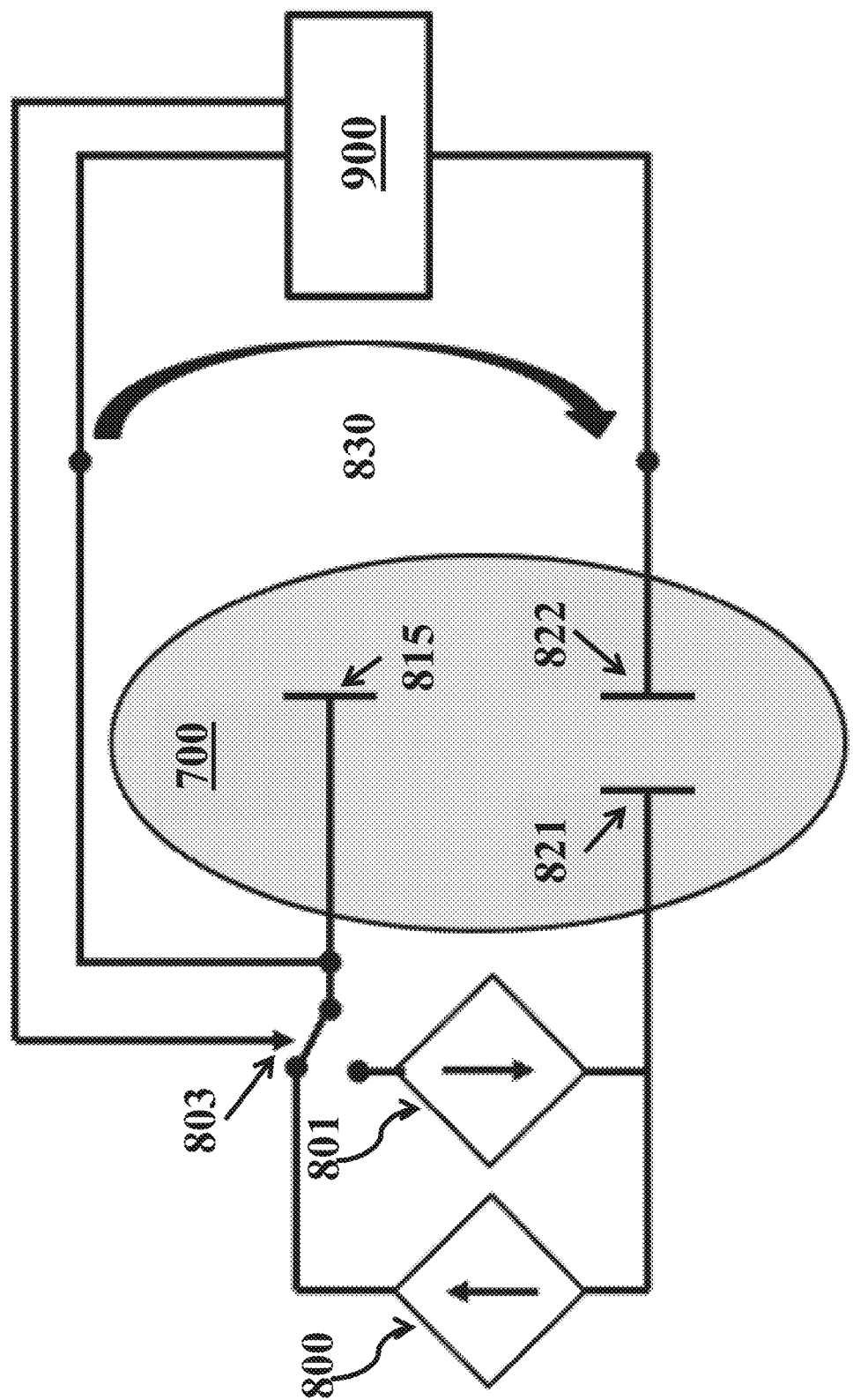
FIG. 46: illustrates a closed loop dual controlled current source with a combined working and sense electrode, according to an example embodiment of the present invention.
Figure 47:
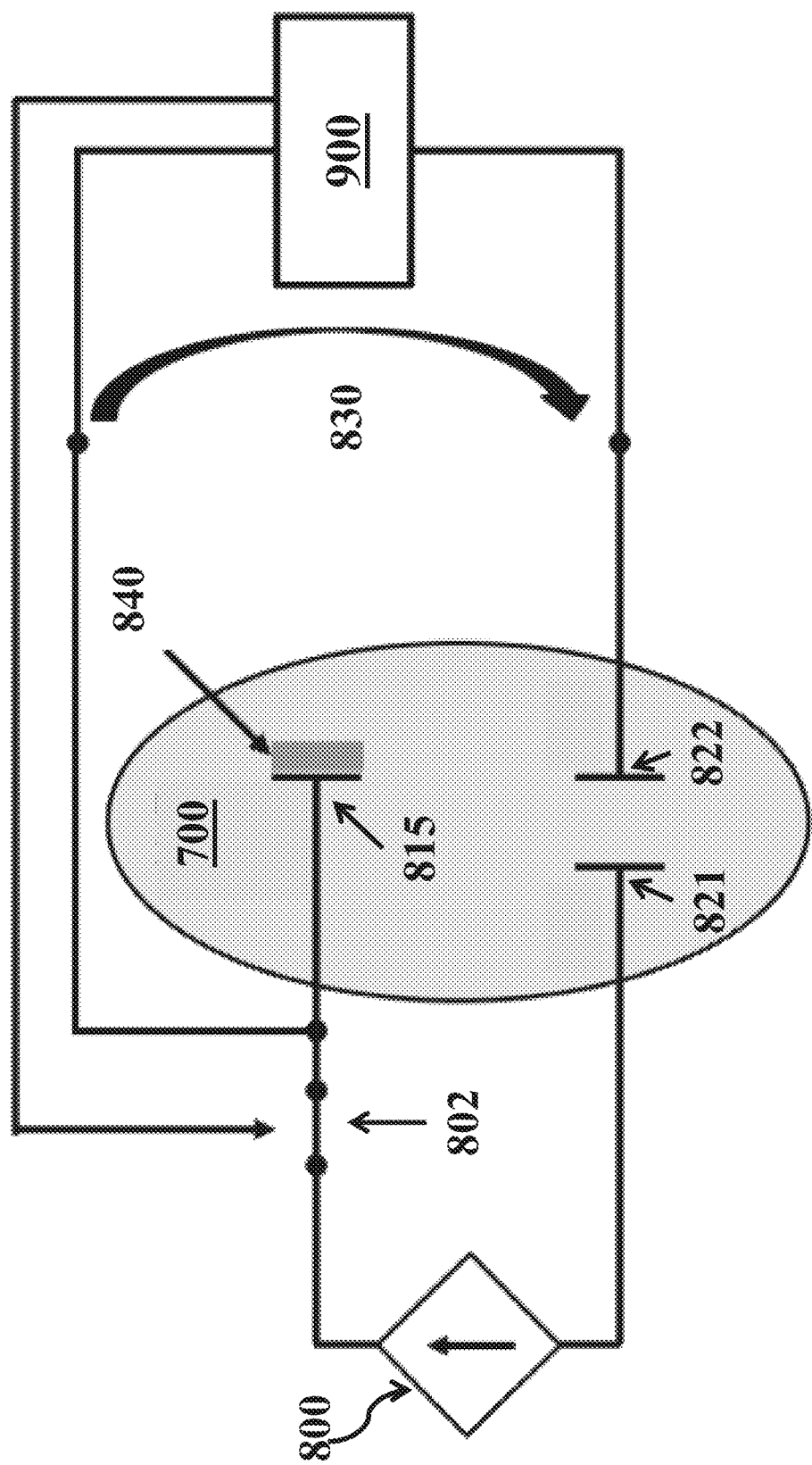
FIG. 47: illustrates a closed loop single controlled current source with a combined working and sense electrode with PANI coating, according to an example embodiment of the present invention.
Figure 48:
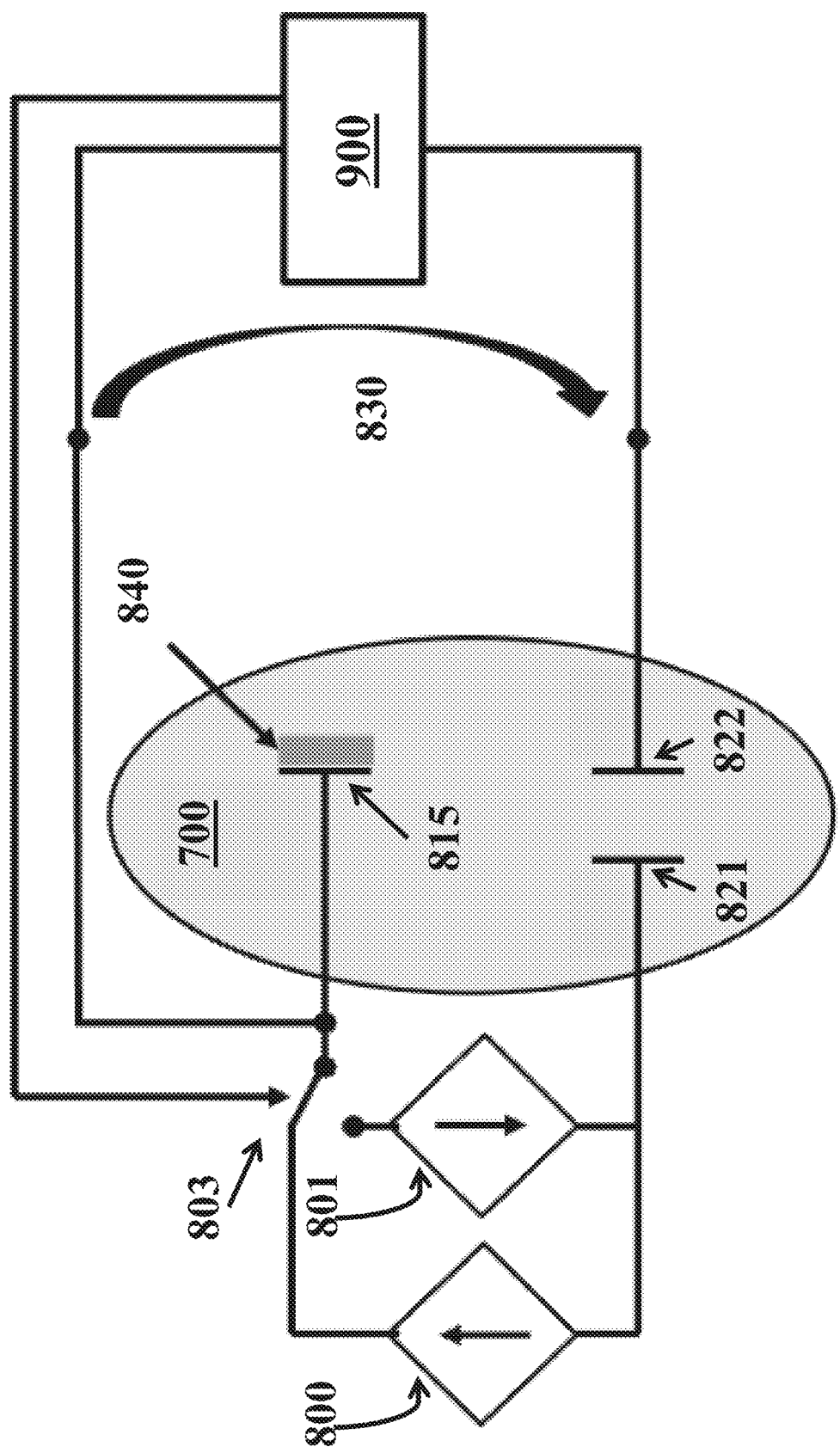
FIG. 48: illustrates a closed loop dual controlled current source with a combined working and sense electrode with PANI coating, according to an example embodiment of the present invention.

FIG. 38A, illustrates a controlled OCP on the SE by using a closed loop feedback method with a single OCP $V_{TARGET}$. In one setup (shown in FIG. 41), the system is driven to apply a current from a current source 800 to increase the H concentration in solution 700 until the $V_{in}$ 830 detected by the SE 817 reaches a single OCP $V_{TARGET}$ value. Then current source 800 is shut off using switch 802 and diffusion of the $H^+$ ions away from the SE 817 results in reduction of the H concentration in solution 700. Similarly, the system can be set to drive a decrease in the H concentration until a OCP $V_{TARGET}$ value is reached and then diffusion of the H ions towards the SE results in increase of the $H^+$ concentration (not shown). In another setup (shown in FIG. 42), positive 800 and negative 802 current sources are used so that the system does not need to rely on diffusion to facilitate the change of pH. This system can actively change the pH in both a positive and negative direction. In this setup the system is driven to apply a positive current from a current source 800 to increase the $H^+$ concentration until the $V_{in}$ 830 reaches a single OCP $V_{TARGET}$ value and a changeover switch 803 is used to connect a negative current source 801 to the WE 816 to apply a negative current and drive the setup in reverse to reduce the H concentration. This way, the system does not rely on passive diffusion but actively monitors and adjusts the pH by electronic control.

Figure 38:
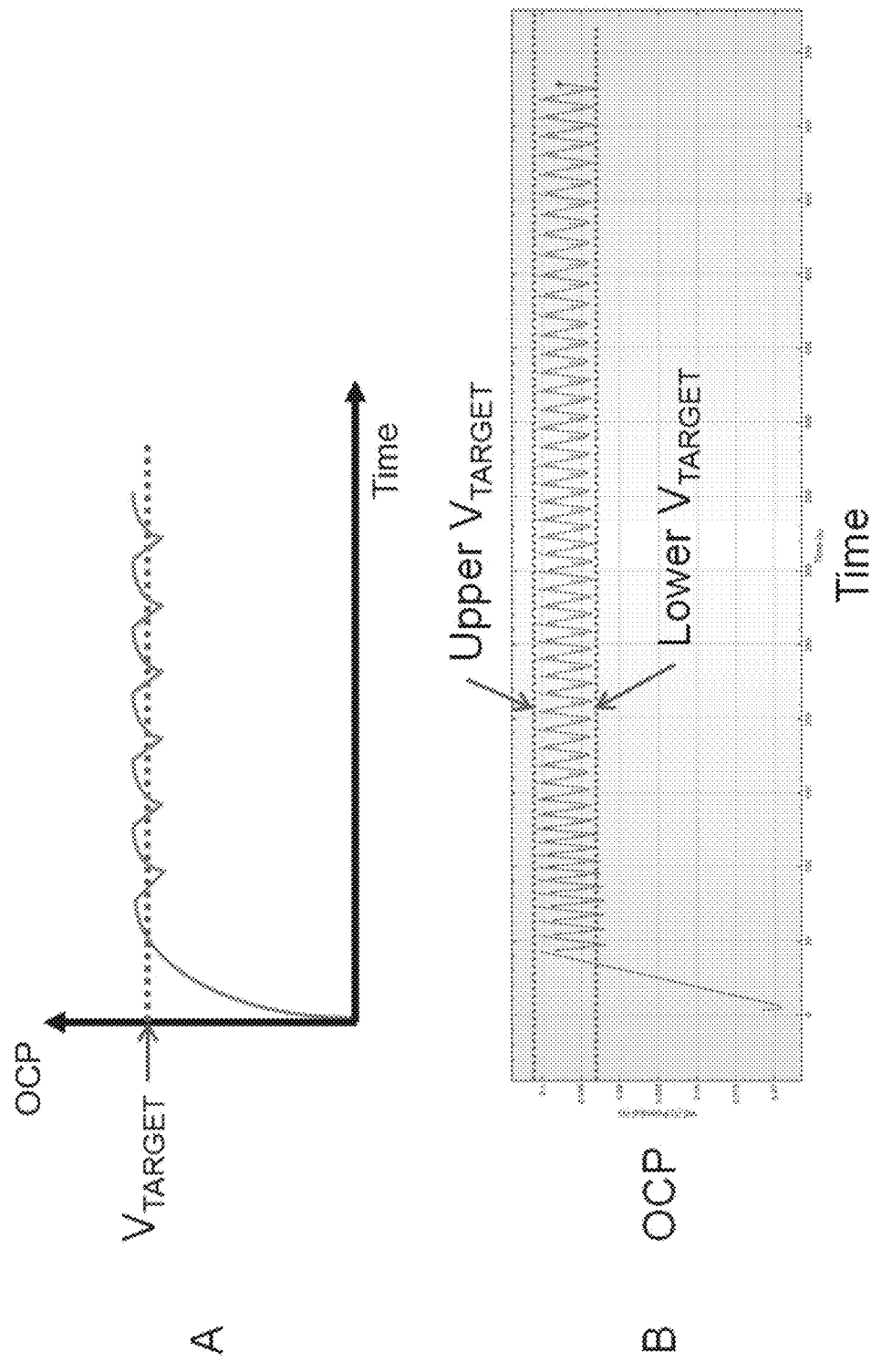
FIG. 38: illustrates, in part A, a controlled OCP on a sense electrode (SE) by using a closed loop feedback method with a single OCP $V_{TARGET}$, and illustrates, in part B, experimental results of a controlled OCP on the SE by using a closed loop feedback with defined upper and lower OCP $V_{TARGET}$ values, according to an example embodiment of the present invention.

FIG. 38 B shows experimental data of the OCP between the SE 817 and RE 822, which changes as current is applied to the WE 816. In this setup (shown in FIG. 41), an upper and a lower target are pre-set via controller 900 for the value of the OCP on the SE 817. The feedback activates current driven pH change when the potential is below the lower bound and switch 802 cuts the current when above the upper bound. The data shows the OCP rising until the upper target is reached. The feedback then switches off the WE 816, which leads to a drop in the OCP as the buffer from the bulk starts to restore the local pH of solution 700. When the OCP reaches the lower target, the current is re-initiated using switch 802 to increase the OCP again. This feedback mechanism allows a defined pH for solution 700 to be maintained close to the WE 816. In another setup (shown in FIG. 42), the feedback can be activated to continuously change the OCP so that a positive current is applied to actively increase the OCP until the upper bound is reached and then a negative current in applied in reverse to actively decrease the OCP until a lower bound is reached. This way, the system does not rely on passive diffusion but actively monitors and adjusts the pH by electronic control.

Figure 39:
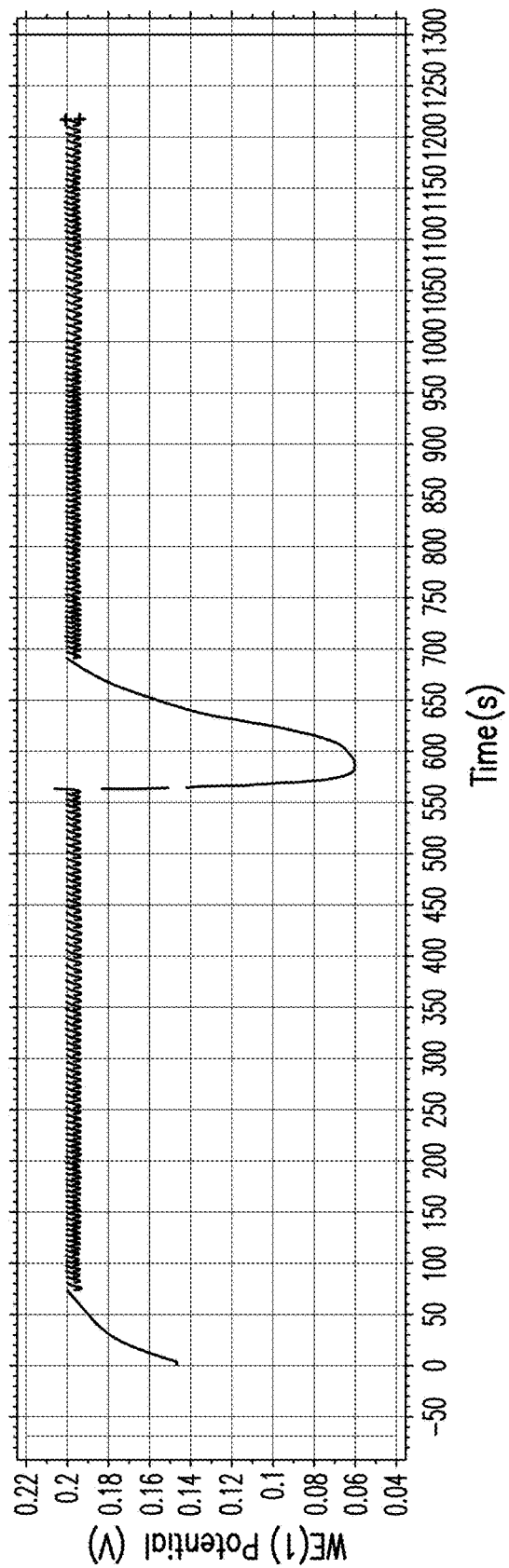
FIG. 39: shows experimental results of a closed look feedback method for controlling the pH of the solution as represented by the open circuit potential voltage measured by the sense electrode (SE) by applying a potential to the working electrode (WE), according to an example embodiment of the present invention.

Further, FIG. 39 shows experimental results of the open circuit potential voltage measured on a sense electrode adjacent to a working electrode with applied current. The working electrode is in a closed loop feedback with the sense electrode. The open circuit potential (OCP) of the working electrode as detected by the sense electrode is analogous to the pH of the solution near the working electrode. The feedback has been set to apply current to the WE only when the sense electrode open circuit potential is below 0.2V. The feedback is then bound between 0.19V and 0.2V (target OCP), switching the potential on the working electrode ON below 0.19 and OFF above 0.2V. The shift at time 560 s is a disruption caused by pipetting the bulk solution into the working electrode. This perturbs the pH gradient that was generated by the current applied to the working electrode causing the pH of the solution to immediately return to the pH of the bulk solution. After pipetting is stopped, the closed loop feedback system is able to restore and then maintain the target OCP.

FIGS. 41-56 show schematics for a closed loop feedback setup, where the OCP between the sense electrode (SE) 816 and reference electrode (RE) 822 is provided as input to a controller 900 that regulates the current source(s) 800-801 or potential source(s) 804-805 through one or more switches 802-803, 806-810. In this way, the system can be triggered on and off to increase or decrease the electrochemial generation/consumption of $H^+$ ions to balance the increase or decrease with the rate of diff-usion of buffering ions from bulk solution to achieve a specific pH value as defined by a target OCP ($V_{TARGET}$) between the SE 816 and RE 822.

Example 20—Use of a pH Sensitive Coating

Figure 37:
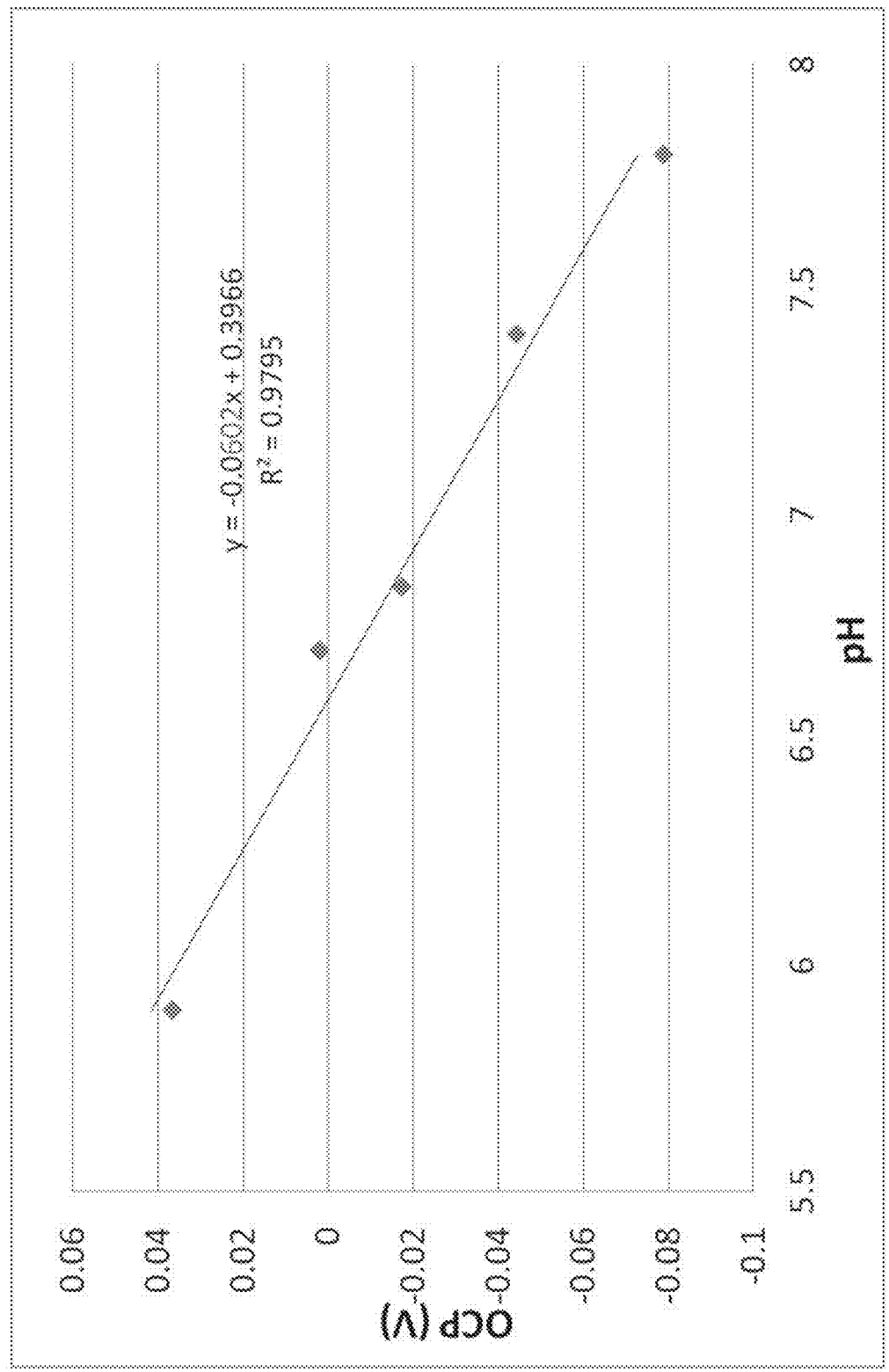
FIG. 37: illustrates a response of the open circuit potential for a PANI coated surface as a function of pH, where the 60 mV/pH is close to the Nernstian limit, according to an example embodiment of the present invention.

To further improve the closed loop pH control method, improved pH sensitivity can be incorporated by the addition of a pH sensitive coating 840 on the working and/or sense electrode 815, 816, 817. An example of such a coating is PANI, which has been shown to have exceptional pH sensitivity. PANI contains charged groups that interact with the hydrogen ions and change the conductivity of the polymer. The response of PANI as a function of pH is close to the Nernstian limit of pH detection (59 mV/pH). The change in open circuit potential of PANI is highly selective for $H^+$ ions, unlike just a bare electrode surface that is sensitive to other ions in solution other than just $H^+$. FIG. 37 shows a response of the open circuit potential (OCP) as a function of pH where the surface of the electrode is coated with a pH sensitive PANI coating. The response of the OCP as a function of pH is shown by the slope of the line to be approximately 60 mV/pH which is close to the Nernstian limit.

Example 21—Device Designs

Figure 40:
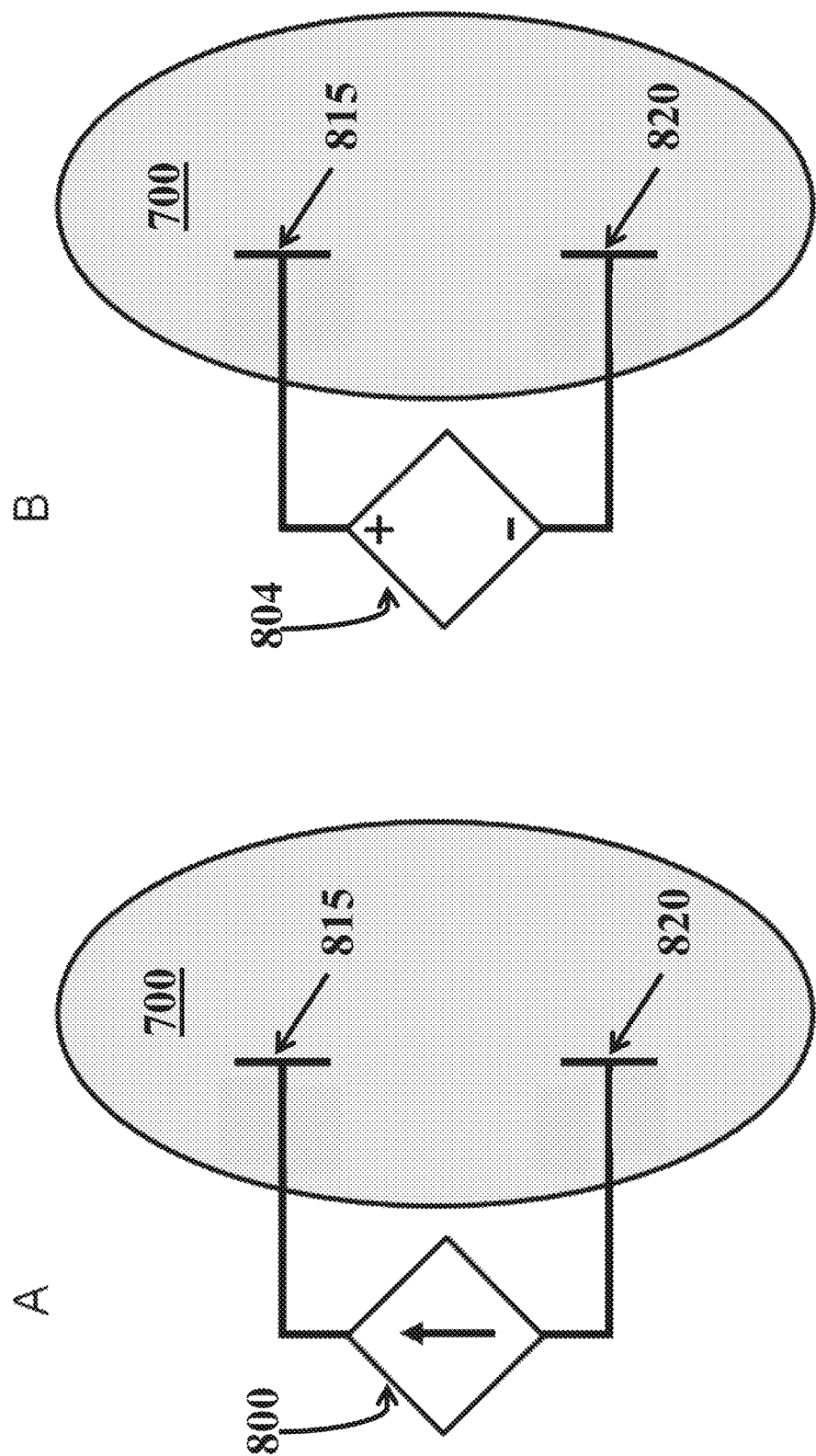
FIG. 40: illustrates open loop schematics, in part A, a controlled current source is used, while in part B, a controlled voltage source is used, according to an example embodiment of the present invention.

FIG. 40 shows example schematics of device designs utilizing the open loop method. In part A, a controlled current source is used while in part B a controlled voltage source is used.

Figure 49:
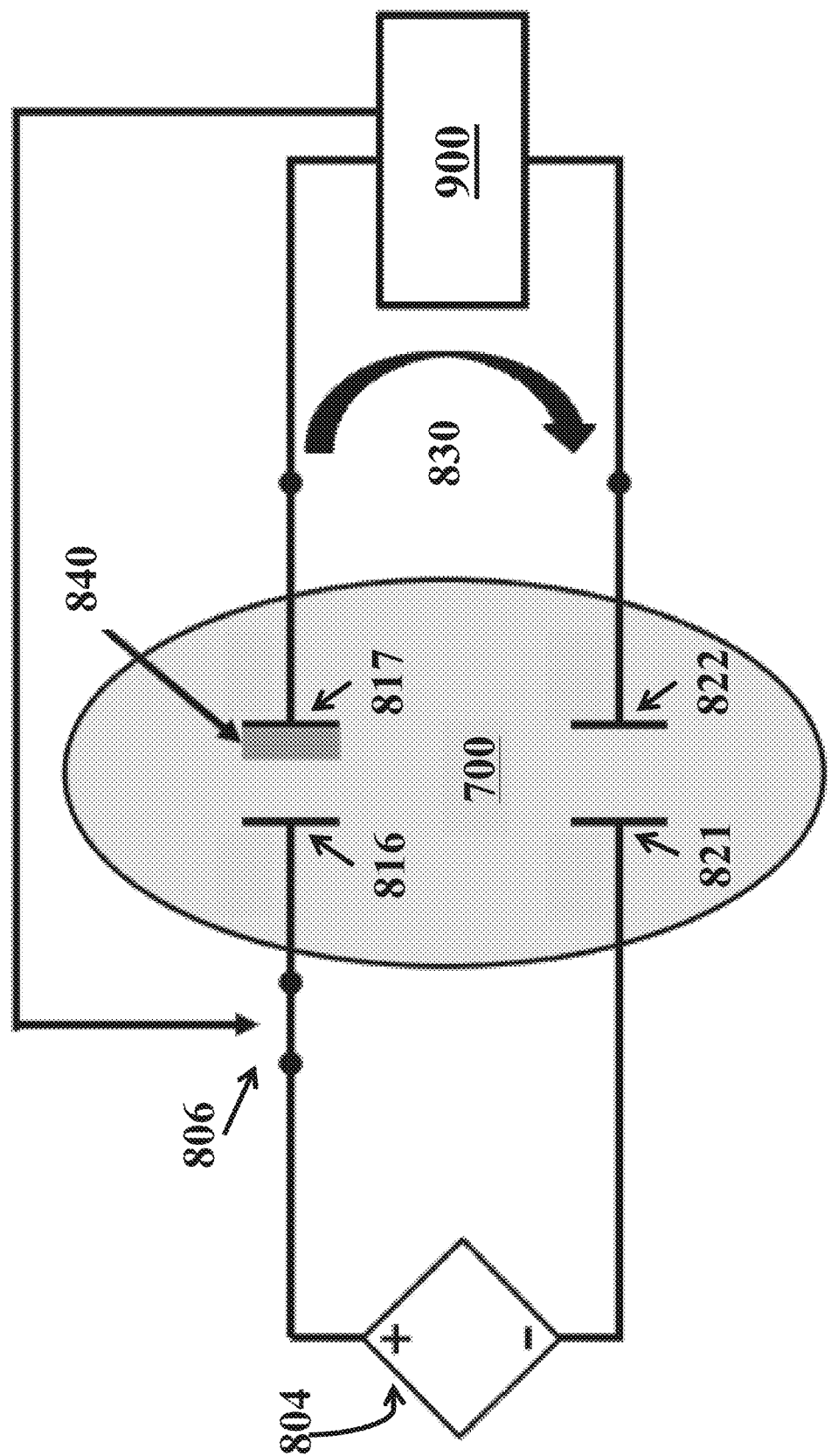
FIG. 49: illustrates a closed loop single controlled potential source with a PANI coated sense electrode, according to an example embodiment of the present invention.
Figure 50:
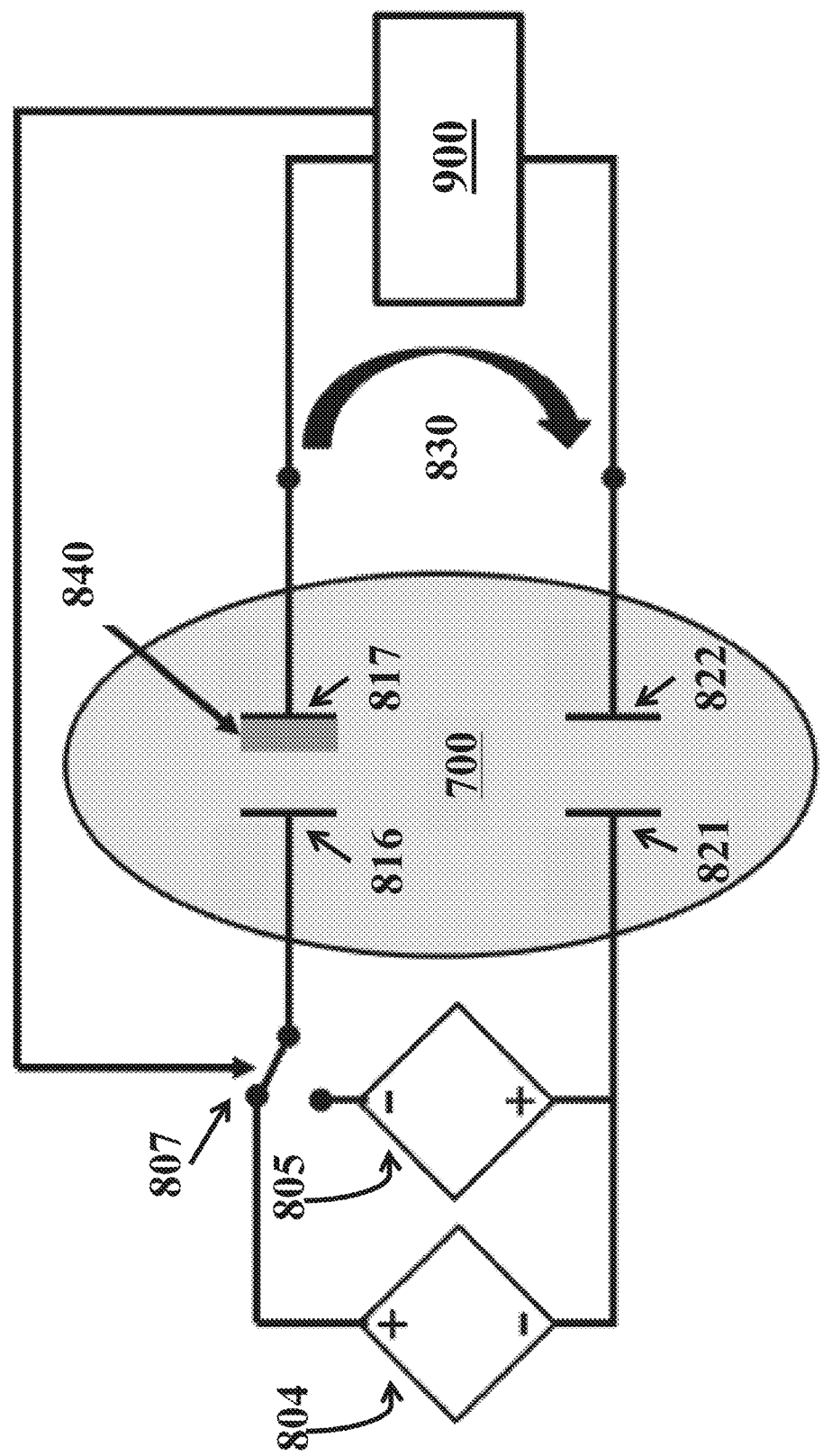
FIG. 50: illustrates a closed loop dual controlled potential source with a PANI coated sense electrode, according to an example embodiment of the present invention.
Figure 51:
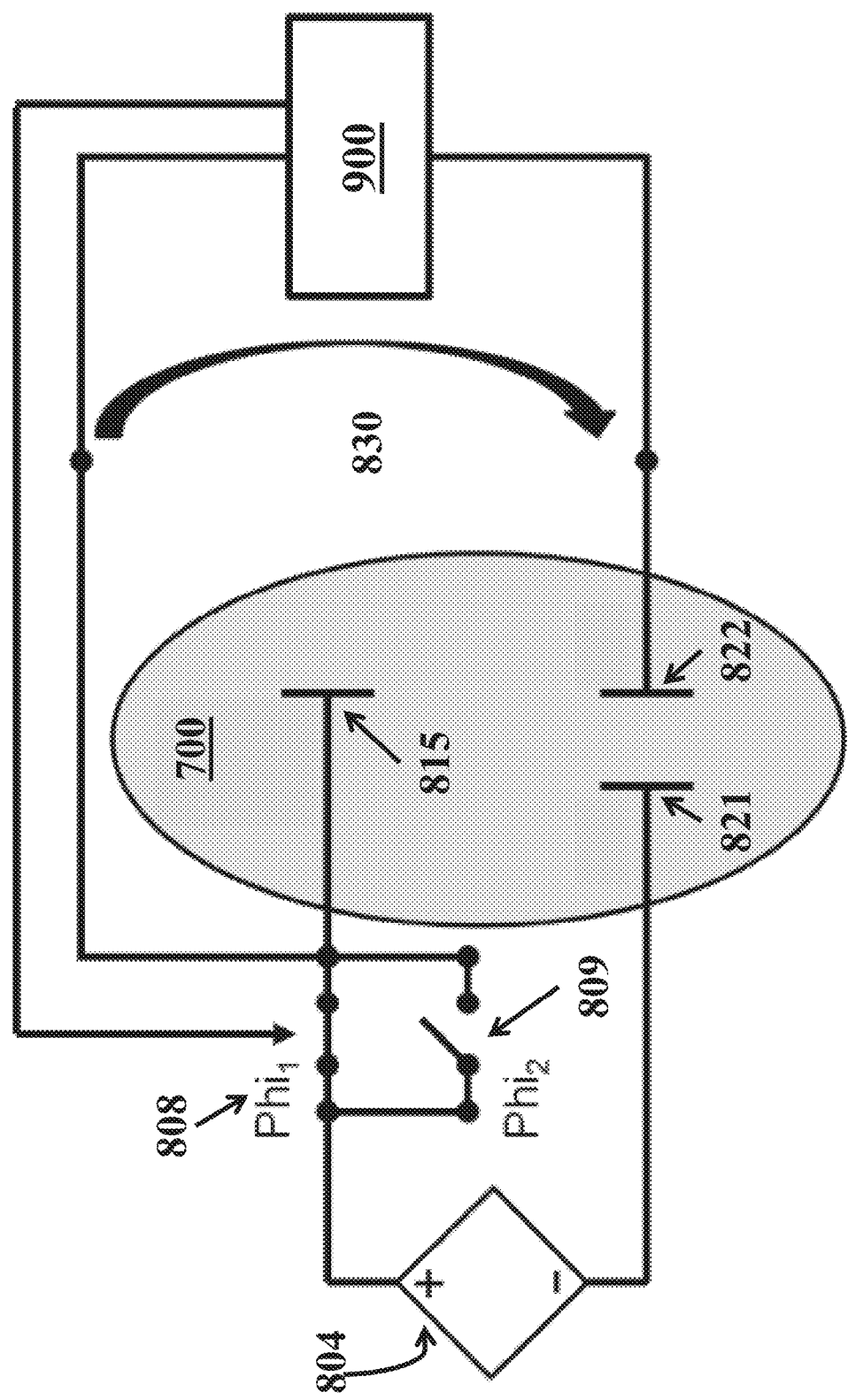
FIG. 51: illustrates a closed loop single controlled potential source with a combined working and sense electrode, where feedback controlled Phi1 and Phi2 switches are for WE potential input and SE measurement output, according to an example embodiment of the present invention.
Figure 52:
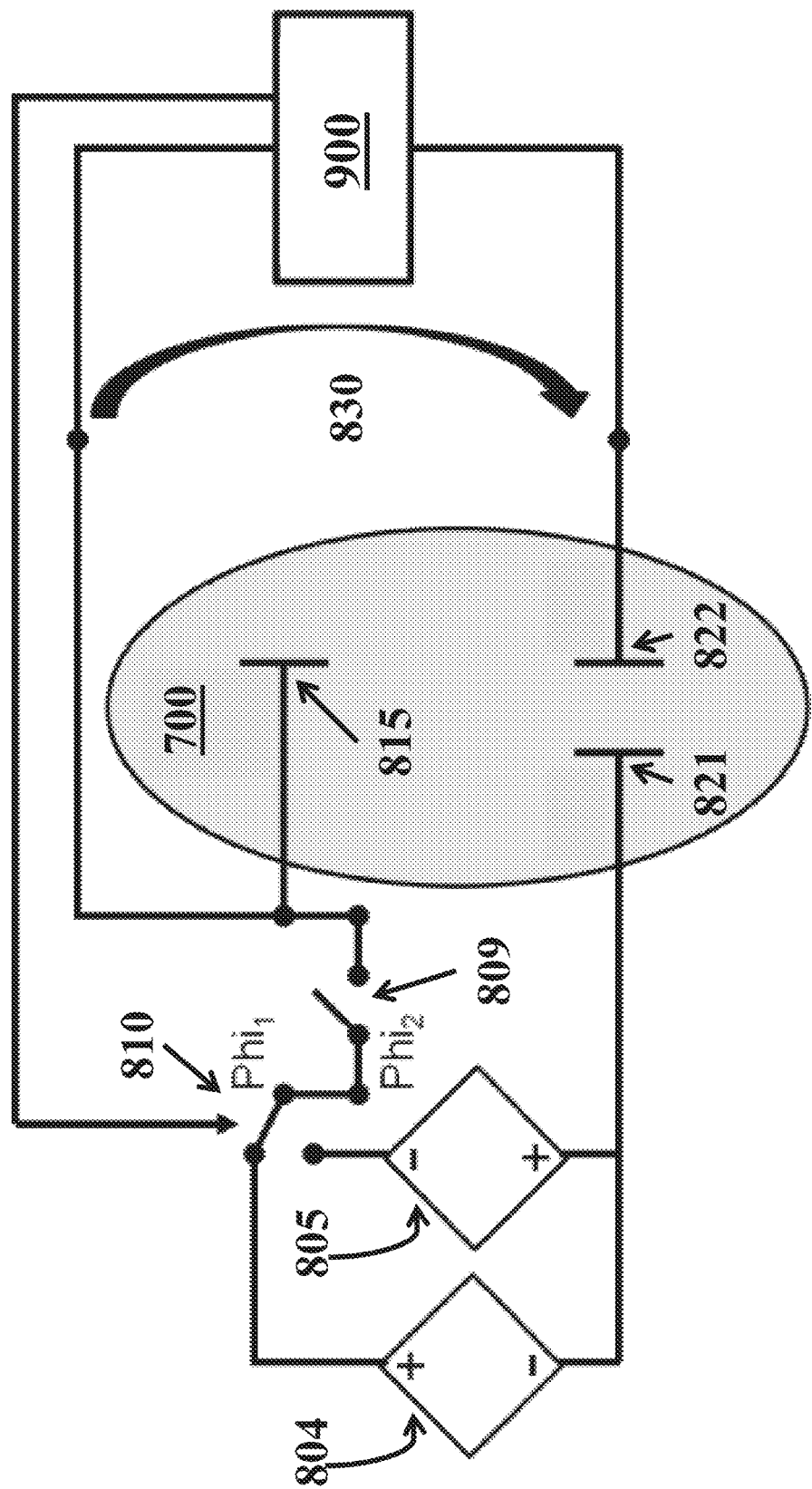
FIG. 52: illustrates a closed loop dual controlled potential source with a combined working and sense electrode, where feedback controlled Phi1 and Phi2 switches are for WE potential input and SE measurement output, according to an example embodiment of the present invention.
Figure 53:
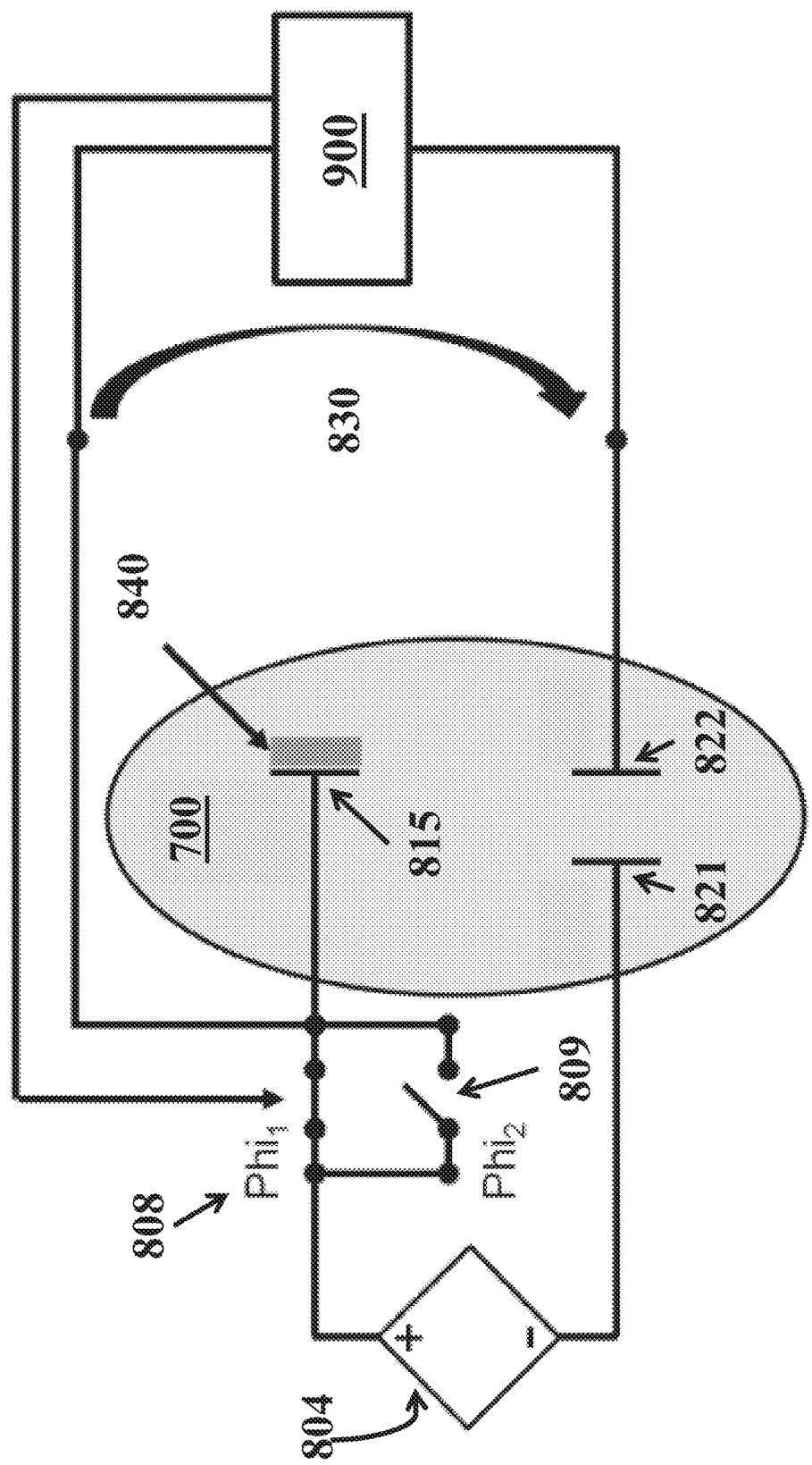
FIG. 53: illustrates a closed loop single controlled potential source with a combined working and sense electrode with PANI coating, where feedback controlled Phi1 and Phi2 switches are for WE potential input and SE measurement output, according to an example embodiment of the present invention.
Figure 54:
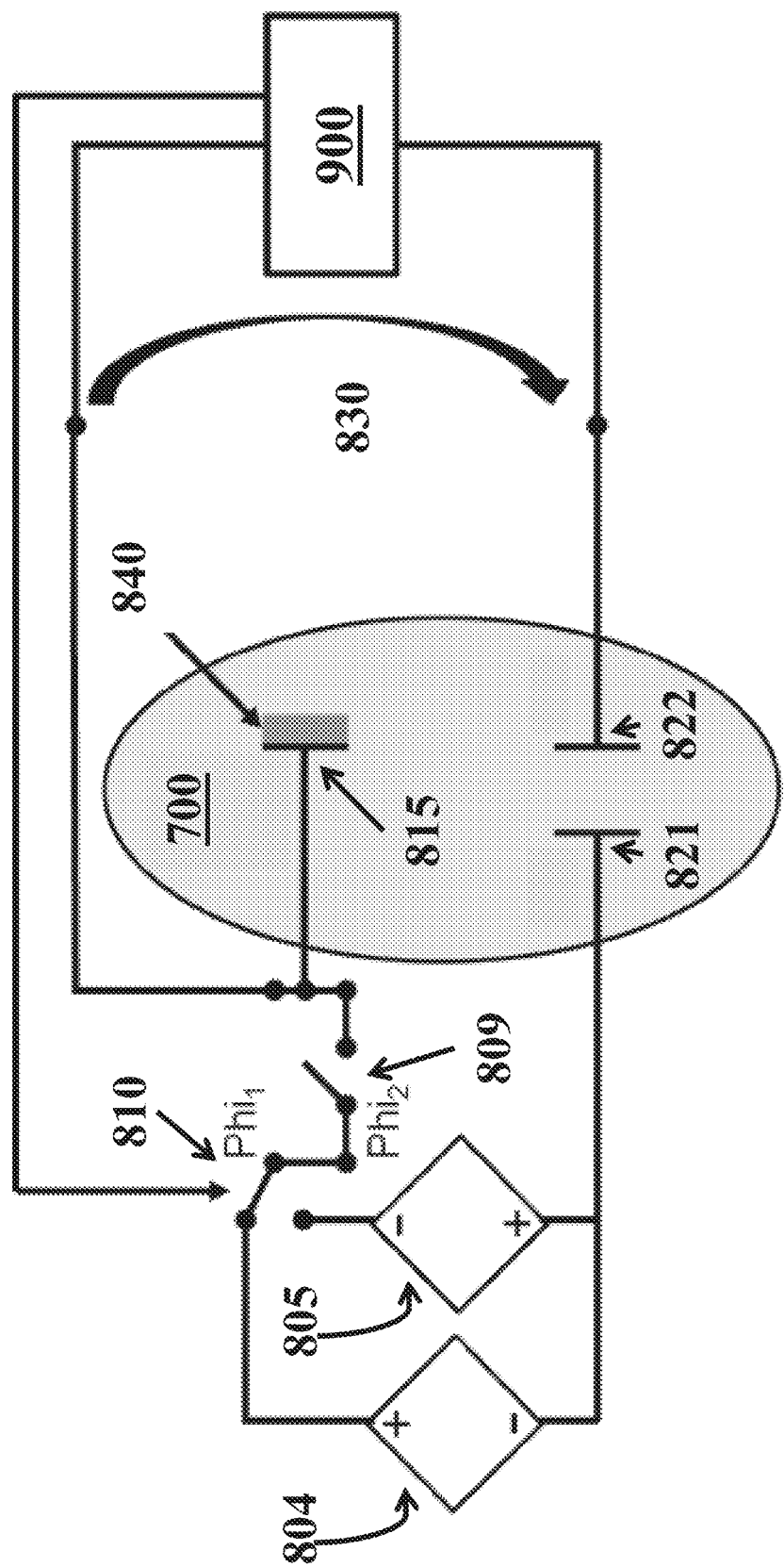
FIG. 54: illustrates a closed loop dual controlled potential source with a combined working and sense electrode with PANI coating, where feedback controlled Phi1 and Phi2 switches are for WE potential input and SE measurement output, according to an example embodiment of the present invention.

Various designs can be used in conjunction with the closed loop method. FIGS. 41, 43, 45, 47, 49, 51, and 53 show various designs for the closed loop method with a single controlled current source 800, and FIGS. 42, 44, 46, 48, 50, 52, and 54-56 show alternative designs using a dual controlled current source 800, 801. The closed loop method can also be implemented on designs with a PANI coated 840 sense electrode 817 (FIGS. 43, 44, 47-50, and 53-56). The WE and SE may also be combined into a single electrode 815 that is able to function as both the sense and working electrodes (FIGS. 45-48). Various switches 802-803, 806-810 are used to connect and disconnect the current 800-801 and voltage sources 804-805. FIGS. 41, 43, 45, and 47 shows a simple switch 802 for connecting and disconnecting the current source 800. FIG. 49 shows a similar switch 806 for connecting and disconnecting the voltage source 804. FIGS. 42, 44, 46, and 48 shows a changeover switch 803 for switching between the positive current source 800 and negative current source 801. FIG. 51 shows a similar changeover switch for switching between positive voltage source 804 and negative voltage source 805. In FIGS. 51-54, switches 808-810 operate in conjunction with clock phases Phi1 and Phi2. Switches 808 and 810 operate in conjunction with clock phase Phi1 and switch 809 in conjunction with Phi2. In each of the above examples the various switches which are controlled by the controller 900 based on feedback to allow for additional levels of control over the WE potential input and SE measurement output.

Figure 55:
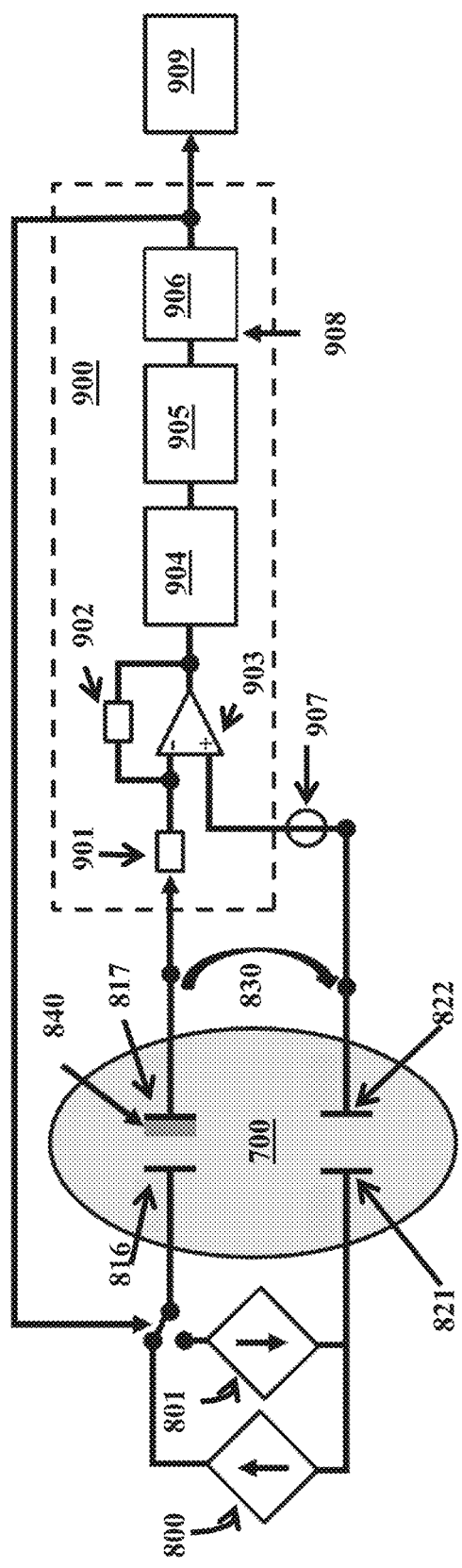
FIG. 55: illustrates a closed loop dual controlled current source with separate working and sense electrode with PANI coating and an analog controller architecture, according to an example embodiment of the present invention.

FIG. 55 schematically shows the system architecture with a closed loop controller. This system controls the pH with only one target value $V_{TARGET}$ 907. The same architecture can be applied to electrochemical cells with systems which use electric voltages instead of electric currents to modulate pH. In an example embodiment, the controller works as follows. The input voltage ($V_{in}$) 830 is sampled 901 and compared 902 to a target voltage $V_{TARGET}$ 907 and the difference is amplified 903 and processed by a loop filter 904. This could also be part of the loop filter and also be realized in different ways, e.g., as a switched capacitor amplifiers or a switched-capacitor loop filter. One example for a loop filter 904 is a PID-controller with a proportional part (P), an integrating part (I) and a differentiating part (D). The output signal of the loop filter 904 is compared with a fixed threshold by a comparator 905. The output of the comparator 905 can be positive or negative. This is equivalent to a digital representation. This digital signal is then stored in a clocked module 906 like a flip-flop or a latch. In an example embodiment, the frequency of the clock 908 is much higher than the frequency which is determined by the inverse of the diffusion time constant of H ions. The output signal of the flip-flop then determines if a positive or negative unity current is applied to the WE 816. This scheme can also be applied to a system with only one current source 800 or to a system with voltage sources 804, 805 instead of current sources 800, 801. The system works as an "electrochemical delta-sigma-modulator," where the quantization error of the unity current sources is "shaped" by the transfer functions of the electrochemical cell and the transfer function of the electronic loop filter 904 and is distributed over a wide frequency spectrum determined by the frequency of the clock CLK 908. The one-bit-output of the comparator can be filtered by a digital filter 909, as shown in FIG. 55. This results in a digital representation of what the system has to apply to electrochemical cell in order to keep the pH at the target value.

Figure 56:
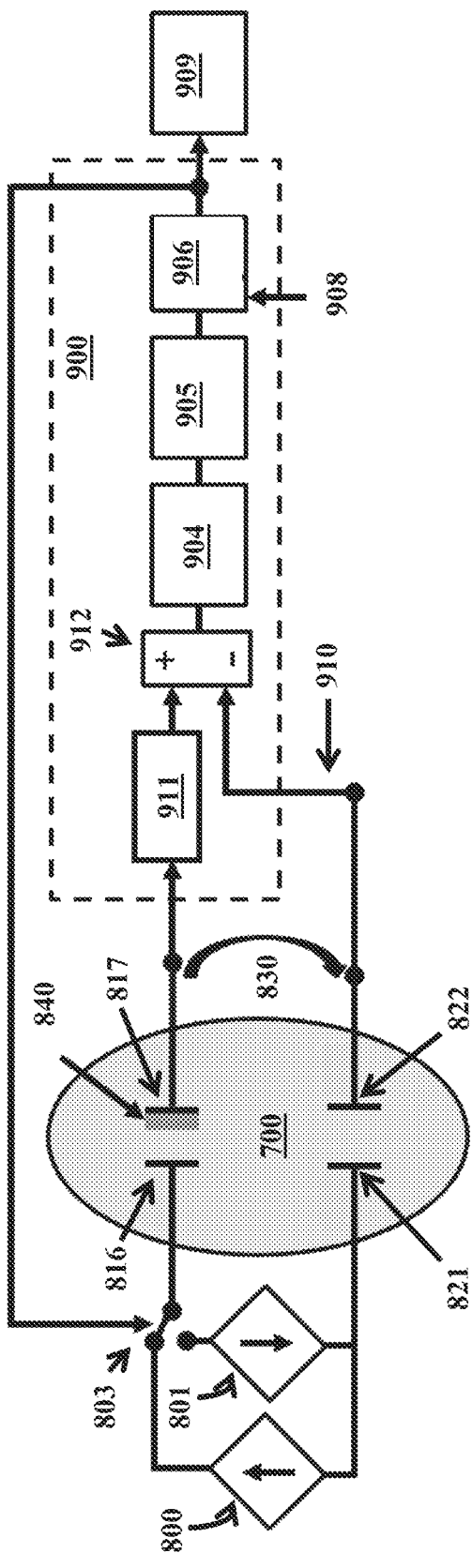
FIG. 56: illustrates a closed loop dual controlled current source with separate working and sense electrode with PANI coating and a digital controller architecture, according to an example embodiment of the present invention. Also shown is a controller architecture design with, in part A, analog signal processing for closed loop feedback control, and, in part B, digital signal processing for closed loop feedback control, the architecture being applicable to the controller schematics designated in FIGS. 41-54, according to an example embodiment of the present invention.

There is flexibility in the controller architecture design in that an analog controller, a digital controller, or a controller using both analog and digital signal processing can be used. FIG. 56 shows a second controller architecture where the main difference from that of FIG. 55 being the way how the target value for pH is set. In FIG. 55, the target pH is set by an analog voltage $V_{TARGET}$ 907. This $V_{TARGET}$ 907 could be generated by a digital-to-analog converter (DAC). In FIG. 56, the input voltage $V_{in}$ 830 is digitized by an analog-to-digital converter (ADC) 911 and then compared 912 with a digital target value 910. As noted above, the electronics is clocked at a frequency 908 much higher than the inverse of the diffusion time constant of the H ions.

The controllers in FIG. 56 can also be used to "measure" using the closed loop method the electric current or voltage that is needed to set a certain target pH. This information can be used to characterize the system and derive stimuli for an open loop system. One example where this might be very useful is an array-structure of many sites where one site is used to "measure" the correct values using the closed loop, and those values are then applied according to the open-loop to many other "mirrored" sites.

Figure 57:
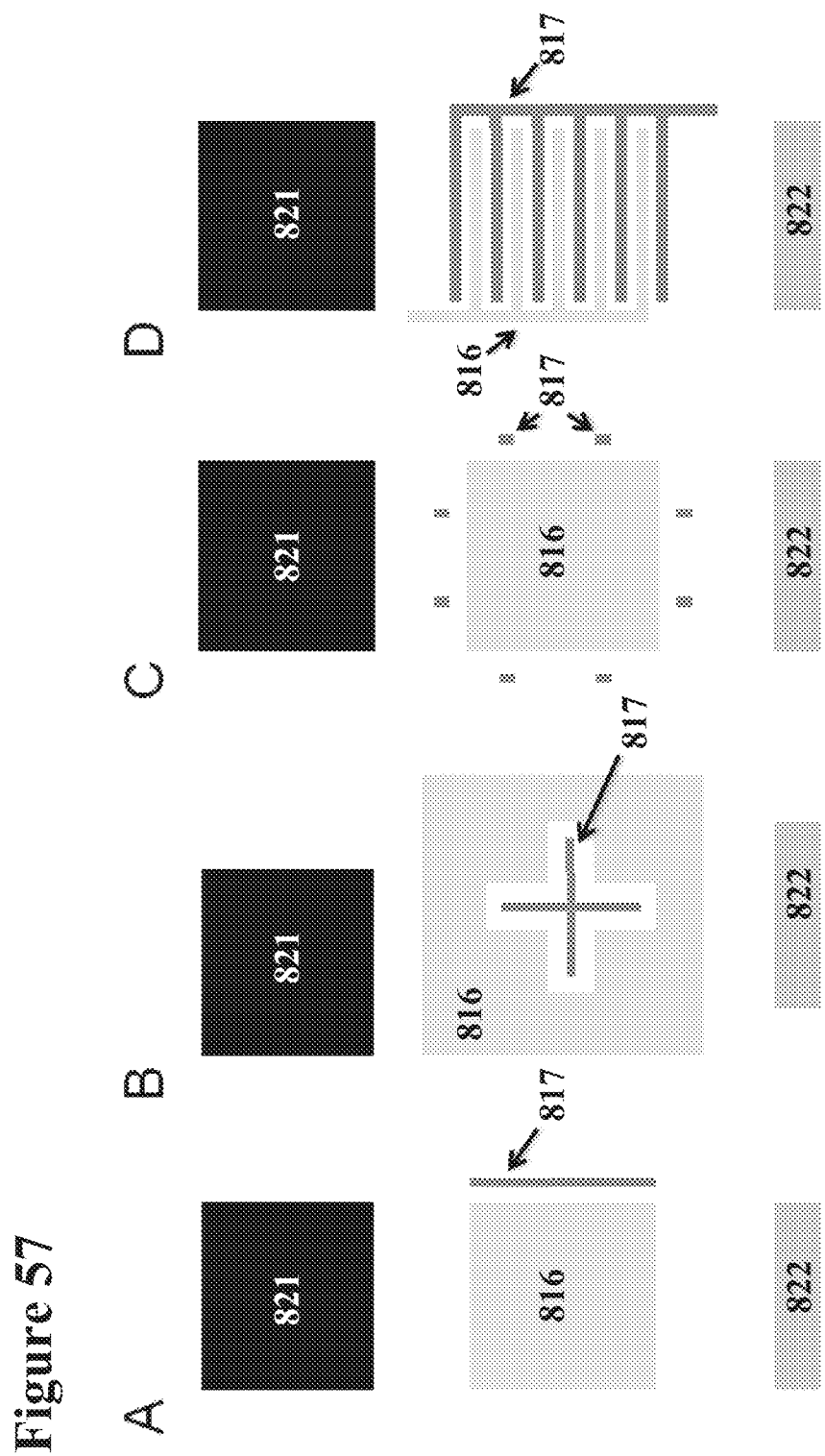
FIG. 57: illustrates potential electrode configurations (routing not shown) for pH sensing, according to example embodiments of the present invention.

FIG. 57 shows an illustration of example electrode configurations (routing not shown) for pH sensing. An illustration of the geometry of the working electrode and sense electrode includes: (A) sense electrode located adjacent to the working electrode, (B) sense electrodes located within the working electrode, (C) multiple sense electrodes for a single working electrode, and (D) interdigitated working and sense electrodes. The incorporation of the PANI surface is advantageous for improving the accuracy of closed loop pH control. There are many different methods to incorporate a sense electrode for monitoring pH. For example, in still another alternative, the working electrode and sense electrode can also be one and the same by switching between active and passive/measuring steps.

What is claimed is:

1. An apparatus comprising:
   an electrochemically active composition that includes a quinone derivative; and
   at least one electrode, wherein:
      a reactivity between a nucleophile and the quinone derivative is reduced compared to a reactivity between the nucleophile and an unsubstituted quinone from which the quinone derivative is derived;
      the apparatus is configured to control the at least one electrode to modulate a pH of at least a portion of the composition to predefined levels by the manipulation of the at least one electrode electrochemically reacting the quinone derivative in a targeted manner to thereby produce $H^+$ ions or $OH^-$ ions;
      the quinone derivative is defined by a chemical formula selected from the group consisting of:

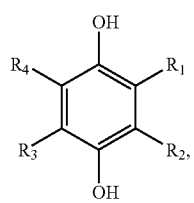

(I)

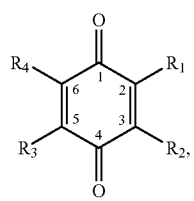

(II)

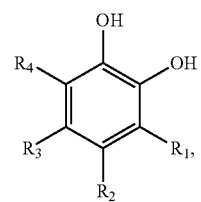

(III)

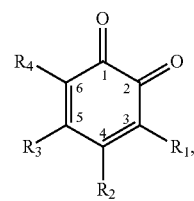

(IV)

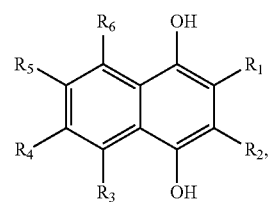

(V)

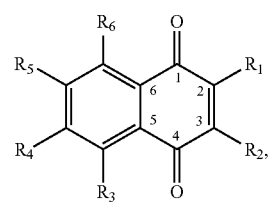

(VI)

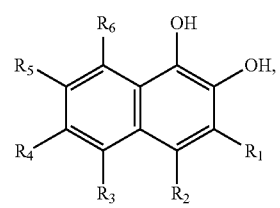

(VII)

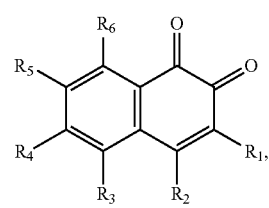

(VIII)

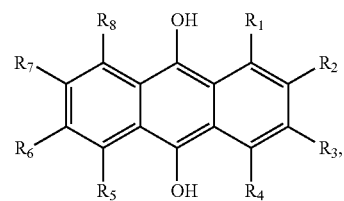

(IX)

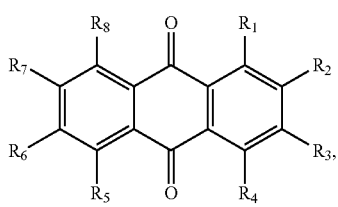

(X)

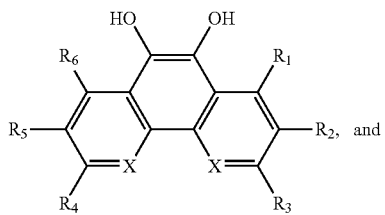

X = C or N (XI)

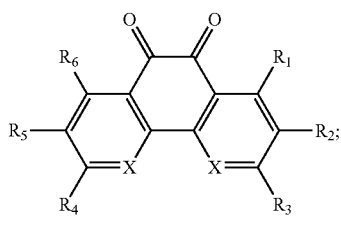

X = C or N (XII)

for chemical formulas I to XII, each R group is independently selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;

at least one of the R groups is not hydrogen;

M is any metal cation or $NH_4^+$;

n is an integer from 1 to $10^9$; and y is an integer from 1 to $10^9$.

2. The apparatus of claim 1, wherein all of the R groups of the quinone derivative are different from each other.

3. The apparatus of claim 1, wherein two or more of the R groups of the quinone derivative are the same.

4. The apparatus of claim 1, wherein the reactivity between the nucleophile and the quinone derivative is reduced compared to the reactivity between the nucleophile and the unsubstituted quinone from which the quinone derivative is derived due to:

(i) increased steric hindrance of a nucleophile binding site by one or more of the R groups;

(ii) elimination of the nucleophile binding site by covalent bonding between the nucleophile binding site and one of the R groups; or (iii) both (i) and (ii).

5. The apparatus of claim 1, wherein the quinone derivative has the chemical formula:

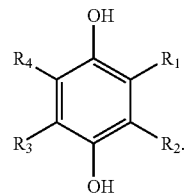

(I)

6. The apparatus of claim 1, wherein the quinone derivative has the chemical formula:

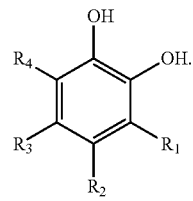

(III)

7. The apparatus of claim 1, wherein the quinone derivative has the chemical formula:

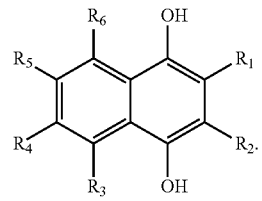

(V)

8. The apparatus of claim 1, wherein the quinone derivative has the chemical formula:

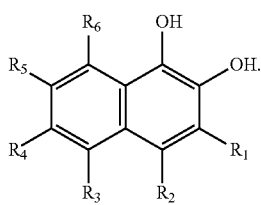
(VII)

9. The apparatus of claim 1, wherein the quinone derivative has the chemical formula:

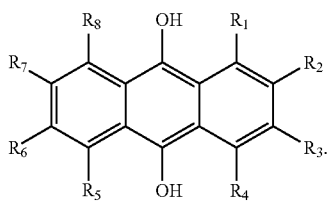
(IX)

10. The apparatus of claim 1, wherein the quinone derivative has the chemical formula:

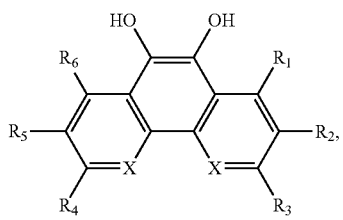
(XI)

wherein X is C or N.

11. The apparatus of claim 1, wherein the quinone derivative has the chemical formula:

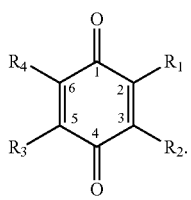
(II)

12. The apparatus of claim 1, wherein the quinone derivative has the chemical formula:

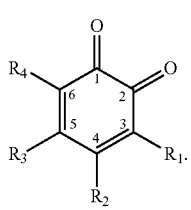
(IV)

13. The apparatus of claim 1, wherein the quinone derivative has the chemical formula:

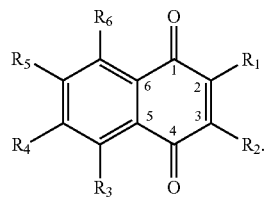
(VI)

14. The apparatus of claim 1, wherein the quinone derivative has the chemical formula:

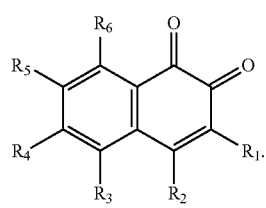
(VIII)

15. The apparatus of claim 1, wherein the quinone derivative has the chemical formula:

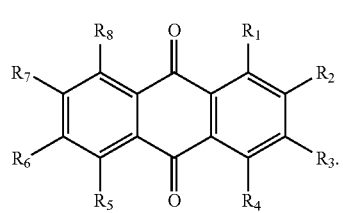
(X)

16. The apparatus of claim 1, wherein the quinone derivative has the chemical formula:

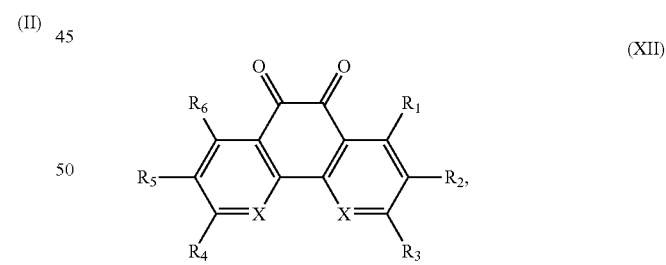
(XII)

wherein X is C or N.

17. An apparatus comprising:
  an electrochemically active composition that includes:
    a quinone derivative, wherein a reactivity between a nucleophile and the quinone derivative is reduced compared to a reactivity between the nucleophile and an unsubstituted quinone from which the quinone derivative is derived; and
    an additive selected from the group consisting of: an aqueous buffer, an organic solvent, an electrolyte, a buffer salt, a bioreagent, a biomolecule, a surfactant, a preservative, a cryoprotectant, and a combination of two or more thereof; and at least one electrode, which the apparatus is configured to control to modulate a pH of at least a portion of the composition to predefined levels by the control of the at least one electrode electrochemically reacting the quinone derivative in a targeted manner to thereby produce $H^+$ ions or $OH^-$ ions.

18. The apparatus of claim 17, wherein the composition is an aqueous solution.

19. An apparatus comprising:
an electrochemically active composition that includes a quinone derivative; and
at least one electrode, wherein:
a reactivity between (a) a nucleophile selected from the group consisting of: amines, thiols, amino acids, peptides, proteins, and a combination of two or more thereof, and (b) the quinone derivative is reduced compared to a reactivity between the nucleophile and an unsubstituted quinone from which the quinone derivative is derived; and
the apparatus is configured to control the at least one electrode to modulate a pH of at least a portion of the composition to predefined levels by the manipulation of the at least one electrode electrochemically reacting the quinone derivative in a targeted manner to thereby produce $H^+$ ions or $OH^-$ ions.

20. The apparatus of claim 19, wherein:
the quinone derivative is derivable from the unsubstituted quinone by substituting one or more R groups of the unsubstituted quinone with a substituent selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})$, $C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;
M is any metal cation or $NH_4^+$;
n is an integer from 1 to $10^9$; and
y is an integer from 1 to $10^9$.

21. The apparatus of claim 20, wherein the reactivity between the quinone derivative and the nucleophile is less than the reactivity between the quinone and the nucleophile due to at least one of:

(i) elimination of a nucleophile binding site in the quinone derivative by covalent bonding between the substituent and the nucleophile binding site;
(ii) steric hindrance of the nucleophile binding site by the substituent; or
(iii) both (i) and (ii).

22. The apparatus of claim 20, wherein the quinone derivative has a chemical formula:

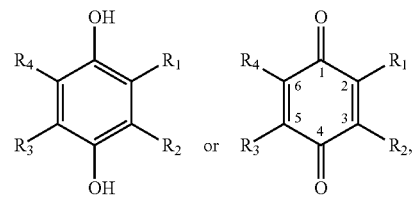

and at least one R group is not H.

23. The apparatus of claim 20, wherein the quinone derivative has a chemical formula:

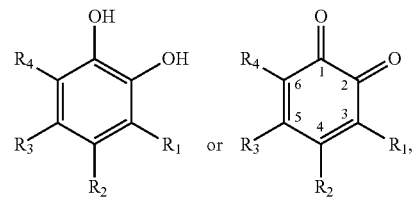

and at least one R group is not H.

24. The apparatus of claim 20, wherein the quinone derivative has a chemical formula:

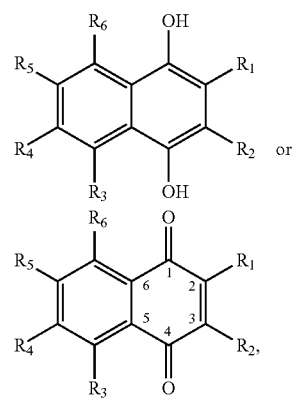

and at least one R group is not H.

25. The apparatus of claim 20, wherein the quinone derivative has a chemical formula:

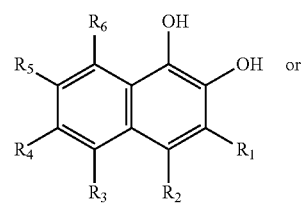

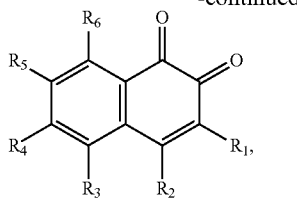

and at least one R group is not H.

26. The apparatus of claim 20, wherein the quinone derivative has a chemical formula:

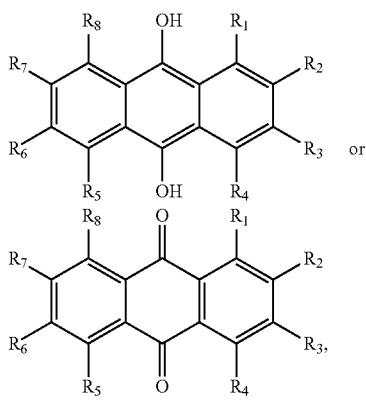

and at least one R group is not H.

27. The apparatus of claim 20, wherein the quinone derivative has a chemical formula:

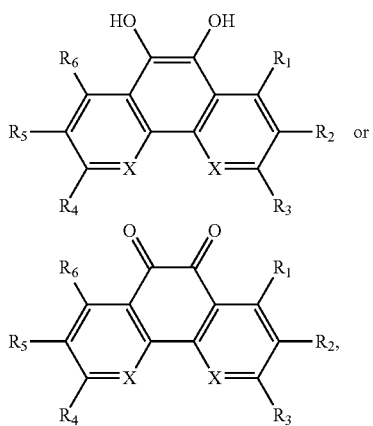

X is C or N, and at least one R group is not H.

28. The apparatus of claim 20, wherein the one or more R groups are substituted with a polar group.

29. The apparatus of claim 28, wherein the polar group has atoms containing lone pair electrons and/or is capable of forming hydrogen bonds with water.

30. The apparatus of claim 28, wherein the polar group contains at least one of oxygen, nitrogen, and sulfur atoms.

31. The apparatus of claim 28, wherein the polar group is selected from the group consisting of: $OH$, $CH_2OH$, $OCH_3$, $COOH$, $SO_3H$, $NH_2$, $NH_3Cl$, $ONa$, a sugar, an amino acid, and a peptide.

32. The apparatus of claim 19, wherein:
the quinone derivative is a substituted methyl quinone synthesizable by:
(i) a halide substitution step of reacting a starting material with a hydrogen halide in the presence of acetic acid and an aldehyde;
(ii) reacting a material produced by step (i) with a nucleophile of structure R—X;
(iii) reacting a material produced by step (ii) with an oxidizing agent; and
(iv) reacting a material produced by step (iii) with a reducing agent;

R is selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_y$ COOH, $S(C_nH_{2n}O)_yCOOM$, $OC_nH_{2n}SH$, $O(C_nH_{2n}O)_y$ SH, $O(C_nH_{2n}O)_ySC_nH_{2n+1}$, $C_nH_{2n}$, $C_nH_{2n}OC_nH_{2n}$, $C_nH_2SC_nH_{2n}$, $C_nH_{2n}NHC_nH_{2n}$, $C_nH_{2n}N(C_nH_{2n+1})$ $C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}$ COOM, $C_nH_{2n+1}COOC_nH_{2n+1}$, $C_nH_{2n+1}CONHC_n$ $H_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}$ $NHC_nH_{2n}NH_2$, $C_nH_{2n+1}N(C_nH_{2n}OH)_2$, $C_nH_{2n+1}N$ $(C_nH_{2n}NH_2)_2$, $C_nH_{2n+1}NHCOC_nH_{2n+1}$, $C_nH_{2n+1}$ $NC_nH_{2n+1}COC_nH_{2n}OH$, $C_nH_{2n+1}NC_nH_{2n+1}$ $COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n+1}O)_yOH$, $C_nH_{2n+1}S(C_nH_{2n}O)_y$ $C_nH_{2n+1}$, $C_nH_{2n+1}S(C_nH_{2n}O)_yCOOH$, $C_nH_{2n+1}S$ $(C_nH_{2n}O)_yCOOM$, sugars, peptides, and amino acids;
M is any metal cation or $NH_4^+$;
n is an integer from 1 to $10^9$;
y is an integer from 1 to $10^9$; and
X is either OH, $NH_2$, NHR, SH, $O^-$, or $S^-$.

33. The apparatus of claim 32, wherein the starting material is dialkoxybenzene.

34. The apparatus of claim 33, wherein the result of the halide substitution step is an ortho-quinon, para-quinone, or a combination thereof.

35. The apparatus of claim 33, wherein a number of halide groups per molecule of the ortho-quinone or para-quinone is 1, 2, 3, or 4.

36. The apparatus of claim 32, wherein the starting material is dialkoxynaphthalene.

37. The apparatus of claim 36, wherein the result of the halide substitution step is an ortho-naphthoquinone, para-naphthoquinone, or a combination thereof.

38. The apparatus of claim 36, wherein a number of halide groups per molecule of the ortho-naphthoquinone or para-naphthoquinone is 1 or 2.

39. The apparatus of claim 32, wherein the hydrogen halide is selected from the group consisting of: HCl, HBr, HI, and combinations thereof.

40. The apparatus of claim 32, wherein the oxidizing agent is selected from the group consisting of: cerium ammonium nitrate, iodine, hydrogen peroxide, hypervalent iodine, iodobenzene diacetate, bromine compounds, and combinations thereof.

41. The apparatus of claim 32, wherein the reducing agent is selected from the group consisting of: sodium borohydrate, potassium borohydrate, sodium hydrosulfite, trichlorosilane, and combinations thereof.

42. A method using an apparatus, the apparatus comprising (a) an electrochemically active composition that includes a quinone derivative and an additive selected from the group consisting of: an aqueous buffer, an organic solvent, an electrolyte, a buffer salt, a bioreagent, a biomolecule, a surfactant, a preservative, a cryoprotectant, and a combination of two or more thereof and (b) at least one electrode, which the apparatus is configured to control to modulate a pH of at least a portion of the composition to predefined levels by the control of the at least one electrode electrochemically reacting the quinone derivative in a targeted manner to thereby produce $H^+$ ions or $OH^-$ ions, the method comprising:

electrochemically reacting the quinone derivative using the one or more electrodes to produce an amount of $H^+$ ions and/or an amount of $OH^-$ ions, wherein the pH of the solution close to the one or more electrodes is controlled by the amount of $H^+$ ions and/or the amount of $OH^-$ ions produced; and collecting signals from the apparatus, wherein a reactivity between a nucleophile and the quinone derivative is reduced compared to a reactivity between the nucleophile and an unsubstituted quinone from which the quinone derivative is derived.

43. The method of claim 42, wherein:

the quinone derivative is defined by a chemical formula selected from the group consisting of:

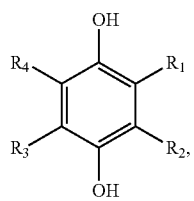

(I)

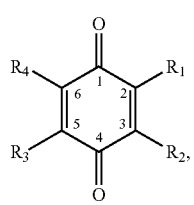

(II)

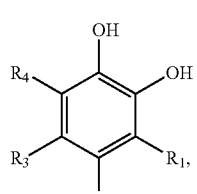

(III)

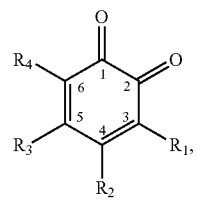

(IV)

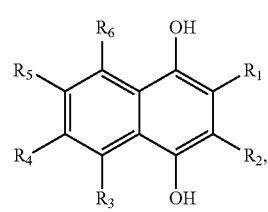

(V)

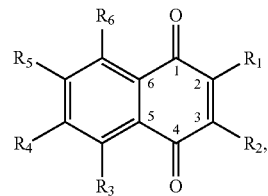

(VI)

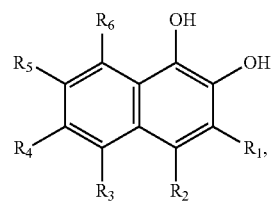

(VII)

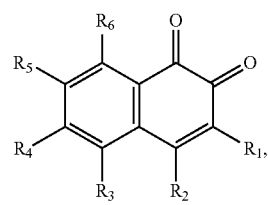

(VIII)

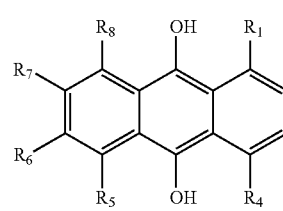

(IX)

(X)

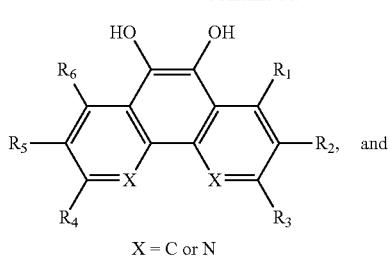

(XI)

X = C or N

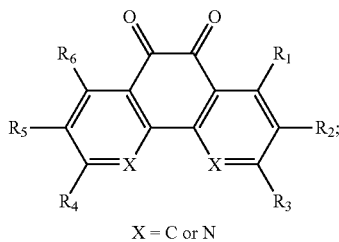

(XII)

X = C or N for formulas I to XII, each R group is independently selected from the group consisting of: H, $C_nH_{2n+1}$, Cl, F, I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$, $O(C_nH_{2n}O)_yCOOM$, COOH, COOM, $COOC_nH_{2n+1}$, $CONHC_nH_{2n+1}$, $CON(C_nH_{2n+1})_2$, $SO_3H$, $SO_3M$, $NH_2$, $NHC_nH_{2n+1}$, $N(C_nH_{2n+1})_2$, $NHC_nH_{2n}OH$, $NHC_nH_{2n}NH_2$, $N(C_nH_{2n}OH)_2$, $N(C_nH_{2n}NH)_2$, $NHCOC_nH_{2n+1}$, $NC_nH_{2n+1}COC_nH_{2n+1}$, $NC_nH_{2n+1}COC_nH_{2n}OH$, $NC_nH_{2n+1}COC_nH_{2n}NH_2$, $NC_nH_{2n+1}COC_nH_{2n}SH$, SH, $SC_nH_{2n}$, $SC_nH_{2n}OH$, $S(C_nH_{2n}O)_yOH$, $S(C_nH_{2n}O)_yOC_nH_{2n+1}$, $S(C_nH_{2n}O)_yCOOH$, $S(C_nH_{2n}O)_yCOOM$, $OC_nH_{2n}SH$, $O(C_nH_{2n}O)_ySH$, $O(C_nH_{2n}O)_ySC_nH_{2n+1}$, $C_nH_{2n}$, $C_nH_{2n}OC_nH_{2n}$, $C_nH_{2n}SC_nH_{2n}$, $C_nH_{2n}NHC_nH_{2n}$, $C_nH_{2n}N(C_nH_{2n+1})C_nH_{2n}$, $C_nH_{2n+1}$, $C_nH_{2n+1}OH$, $C_nH_{2n+1}OC_nH_{2n}$, $C_nH_{2n+1}OC_nH_{2n}OH$, $C_nH_{2n+1}O(C_nH_{2n}O)_yCOOH$, $C_nH_{2n+1}O(C_nH_{2n}O)_yCOOM$, $C_nH_{2n+1}COOH$, $C_nH_{2n+1}COOM$, $C_nH_{2n+1}COOC_nH_{2n+1}$, $C_nH_{2n+1}CONHC_nH_{2n+1}$, $C_nH_{2n+1}CONH(C_nH_{2n+1})_2$, $C_nH_{2n+1}SO_3H$, $C_nH_{2n+1}SO_3M$, $C_nH_{2n+1}NH_2$, $C_nH_{2n+1}NHC_nH_{2n+1}$, $C_nH_{2n+1}N(C_nH_{2n+1})_2$, $C_nH_{2n+1}NHC_nH_{2n}OH$, $C_nH_{2n+1}NHC_nH_{2n}NH_2$, $C_nH_{2n+1}N(C_nH_{2n}OH)_2$, $C_nH_{2n+1}N(C_nH_{2n}NH_2)_2$, $C_nH_{2n+1}NHCOC_nH_{2n+1}$, $C_nH_{2n+1}NC_nH_{2n+1}COC_nH_{2n}OH$, $C_nH_{2n+1}NC_nH_{2n+1}COC_nH_{2n}NH_2$, $C_nH_{2n+1}NC_nH_{2n+1}COC_nH_{2n}SH$, $C_nH_{2n+1}SH$, $C_nH_{2n+1}SC_nH_{2n}$, $C_nH_{2n+1}SC_nH_{2n}OH$, $C_nH_{2n+1}S(C_nH_{2n}O)_yOH$, $C_nH_{2n+1}S(C_nH_{2n}O)_yOC_nH_{2n+1}$, $C_nH_{2n+1}S(C_nH_{2n}O)_yCOOH$, $C_nH_{2n+1}S(C_nH_{2n}O)_yCOOM$, sugars, peptides, and amino acids;

at least one of the R groups is not hydrogen;

M is any metal cation or $NH_4^+$;

n is an integer from 1 to $10^9$; and y is an integer from 1 to $10^9$.

44. The method of claim 42, wherein the solution contains one or more nucleophiles.

45. The method of claim 44, wherein the one or more nucleophiles are selected from the group consisting of: amines, thiols, amino acids, peptides, proteins, and combinations thereof.

46. The method of claim 42, wherein the solution contains a reduced quinone derivative and electrochemically reacting the quinone derivative results in an electrochemical oxidation reaction of the reduced quinone derivative to make the pH of the solution more acidic.

47. The method of claim 46, wherein the concentration of the reduced quinone derivative is 0 to 1M.

48. The method of claim 42, wherein the solution contains an oxidized quinone derivative and electrochemically reacting the quinone derivative results in an electrochemical reduction reaction of the oxidized quinone derivative to make the pH of the solution more basic.

49. The method of claim 48, wherein the concentration of the oxidized quinone derivative is 0 to 1M.

50. The method of claim 42, wherein the solution contains one or more buffer components provided in a concentration that is 0 to 1M.

51. The method of claim 50, wherein the one or more buffer components are selected from the group consisting of: organic solvents, electrolytes, bioreagents, biomolecules, surfactants, and combinations thereof.

52. The method of claim 42, further comprising measuring the pH of the solution.

53. The method of claim 42, wherein the quinone derivative is electrochemically reacted by providing an amount of electric current.

54. The method of claim 53, further comprising measuring the pH before providing the amount of electric current.

55. The method of claim 54, wherein the amount of electric current is selected based on the measured pH.

* * * * *